(12) United States Patent
Letavic et al.

(10) Patent No.: US 10,150,766 B2
(45) Date of Patent: Dec. 11, 2018

(54) P2X7 MODULATORS

(71) Applicant: Jansssen Pharmaceutica NV, Beerse (BE)

(72) Inventors: Michael A. Letavic, San Diego, CA (US); Jason C. Rech, San Diego, CA (US); Jessica L. Wall, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/540,658

(22) PCT Filed: Aug. 25, 2015

(86) PCT No.: PCT/US2015/046710
§ 371 (c)(1),
(2) Date: Jun. 29, 2017

(87) PCT Pub. No.: WO2016/039977
PCT Pub. Date: Mar. 17, 2016

(65) Prior Publication Data
US 2017/0342066 A1      Nov. 30, 2017

Related U.S. Application Data

(60) Provisional application No. 62/049,687, filed on Sep. 12, 2014.

(51) Int. Cl.
| | | |
|---|---|---|
| *C07D 487/14* | (2006.01) | |
| *C07D 403/14* | (2006.01) | |
| *C07D 401/14* | (2006.01) | |
| *A61K 31/529* | (2006.01) | |
| *C07D 471/04* | (2006.01) | |
| *A61K 31/14* | (2006.01) | |
| *A61P 19/02* | (2006.01) | |

(52) U.S. Cl.
CPC ............ *C07D 471/04* (2013.01); *A61K 31/14* (2013.01); *C07D 401/14* (2013.01); *C07D 403/14* (2013.01); *C07D 487/14* (2013.01)

(58) Field of Classification Search
CPC .. C07D 487/14; C07D 403/14; C07D 401/14; A61K 31/529
USPC .......................................... 544/250; 514/267
See application file for complete search history.

(56) References Cited

U.S. PATENT DOCUMENTS

| | | | |
|---|---|---|---|
| 4,812,462 A | 3/1989 | Blankley et al. | |
| 4,816,463 A | 3/1989 | Blankley et al. | |
| 5,338,744 A | 8/1994 | Dudley et al. | |
| 8,431,704 B2 | 4/2013 | Love et al. | |
| 8,871,760 B2 | 10/2014 | Brotherton-Pleiss et al. | |
| 8,933,236 B2 | 1/2015 | Chowdhury et al. | |
| 8,987,249 B2 | 3/2015 | Anderskewitz et al. | |
| 9,040,534 B2 | 5/2015 | Ameriks et al. | |
| 9,056,874 B2 | 6/2015 | Adams et al. | |
| 9,066,946 B2 | 6/2015 | Alcazar Vaca et al. | |
| 9,156,824 B2 | 10/2015 | Dally et al. | |
| 9,181,271 B2 | 11/2015 | Li et al. | |
| 9,233,974 B2 | 1/2016 | Link et al. | |
| 9,242,969 B2 | 1/2016 | Barsanti et al. | |
| 9,273,047 B2 | 3/2016 | Hunt et al. | |
| 9,290,476 B2 | 3/2016 | Leonard et al. | |
| 9,375,418 B2 | 6/2016 | Schmidt et al. | |
| 9,434,715 B2 | 9/2016 | Conza et al. | |
| 9,447,045 B2 | 9/2016 | Chen et al. | |
| 9,464,084 B2 | 10/2016 | Alcazar Vaca et al. | |
| 9,532,992 B2 | 1/2017 | Kuntz et al. | |
| 9,540,388 B2 | 1/2017 | Letavic et al. | |
| 9,561,228 B2 | 2/2017 | Haq et al. | |
| 9,617,272 B2 | 4/2017 | Kumar et al. | |
| 9,637,456 B2 | 5/2017 | Amans et al. | |
| 2005/0096345 A1 | 5/2005 | Thompson et al. | |
| 2006/0217448 A1 | 9/2006 | Kelly et al. | |
| 2006/0293337 A1 | 12/2006 | Evans et al. | |
| 2008/0275052 A1 | 11/2008 | Dhar et al. | |
| 2010/0144758 A1 | 6/2010 | Dillon et al. | |

(Continued)

FOREIGN PATENT DOCUMENTS

| | | |
|---|---|---|
| CN | 101778850 A | 7/2010 |
| JP | 2013-505220 | 2/2013 |

(Continued)

OTHER PUBLICATIONS

Bartlett et al., Pharmacol Rev 66:638-675, Jul. 2014.*

(Continued)

*Primary Examiner* — Venkataraman Balasubramanian
(74) *Attorney, Agent, or Firm* — Thomas J. Dodd

(57) ABSTRACT

The present invention is directed to compounds of Formula (I), which includes enantiomer and diasteromers thereof:

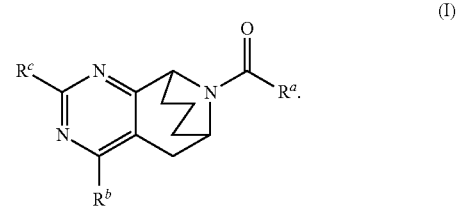

The invention also relates to pharmaceutical compositions comprising compounds of Formula (I). Methods of making and using the compounds of Formula (I) are also within the scope of the invention.

36 Claims, No Drawings

(56) References Cited

U.S. PATENT DOCUMENTS

| | | |
|---|---|---|
| 2011/0252717 A1 | 10/2011 | Graf Fernandez |
| 2011/0294790 A1 | 12/2011 | Mantegani et al. |
| 2012/0190680 A1 | 7/2012 | Bakthavatchalam et al. |
| 2014/0213554 A1 | 7/2014 | Wu et al. |
| 2014/0251902 A1 | 9/2014 | Solheim et al. |
| 2014/0275015 A1 | 9/2014 | Alcazar Vaca et al. |
| 2014/0275056 A1 | 9/2014 | Letavic et al. |
| 2014/0275096 A1 | 9/2014 | Ameriks et al. |
| 2014/0275120 A1 | 9/2014 | Alcazar Vaca et al. |
| 2015/0029190 A1 | 1/2015 | Ishida et al. |
| 2015/0290190 A1 | 10/2015 | Ameriks et al. |
| 2015/0322062 A1 | 11/2015 | Alcazar Vaca et al. |
| 2016/0016962 A1 | 1/2016 | Ameriks et al. |
| 2016/0024082 A1 | 1/2016 | Alcazar Vaca et al. |
| 2016/0039809 A1 | 2/2016 | Alcazar Vaca et al. |
| 2016/0039836 A1 | 2/2016 | Letavic et al. |
| 2016/0046596 A1 | 2/2016 | Banerjee et al. |
| 2017/0081342 A1 | 3/2017 | Cheung et al. |

FOREIGN PATENT DOCUMENTS

| | | |
|---|---|---|
| WO | 2004014374 A1 | 2/2004 |
| WO | 2006023750 A2 | 3/2006 |
| WO | 2006080884 A1 | 8/2006 |
| WO | 2006110516 A1 | 10/2006 |
| WO | 2009002423 A2 | 12/2008 |
| WO | 2009023623 A1 | 2/2009 |
| WO | 20100125101 A1 | 11/2010 |
| WO | 20100125102 A1 | 11/2010 |
| WO | 2011121137 A1 | 10/2011 |
| WO | 2012040048 A2 | 3/2012 |
| WO | 2014152589 A1 | 9/2014 |
| WO | 2014152621 A1 | 9/2014 |
| WO | 2014154897 A1 | 10/2014 |
| WO | 2016039977 A1 | 3/2016 |
| WO | 2016039983 A1 | 3/2016 |

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.*
PCT ISR dated Jul. 31, 2009 for International Application No. PCT/US2009/041249.
PCT ISR dated Oct. 15, 2015 for International Application No. PCT/US2015/046710.
PCT ISR dated Aug. 12, 2014 for International Application No. PCT/US2014/027450.
PCT ISR dated Jul. 1, 2014 for International Application No. PCT/US2014/027505.
PCR ISR dated Jul. 1, 2014 for International Application No. PCT/US2014/027522.
PCT ISR dated Jun. 17, 2014 for International Application No. PCT/US2014/027540.
Database CHEMCATS, 2-Naphtalenecarboxamide,6-Methoxy-N-[2-(4-morpholinyl)-2-(2-thienyl) ethyl], Enamine Screening Library, Jan. 17, 2008, pp. 1-1, 940789-91-3.
Database CHEMCATS, 2-Quinolinecarboxamide,N-[2-(5-methyl-2-furanyl)-2-(4-morpholinyl) ethyl], Ryan Scientific Screening Library, Jan. 25, 2008, pp. 1-1, 924250-65-7.
Database CHEMCATS, 2-Quinolinecarboxamide,N-[2-(5-methyl1-2-furanyl)-2-(4-morpholinyl) ethyl], Ambinter Stock Screening Collection, Feb. 13, 2008, pp. 1-1, 924250-65-7.
Database CHEMCATS, 3-Quinolinecarboxamide,1,2-dihydro N-[2-(4-morpholinyl)-2-(2-thienyl) ethyl]-2-oxo, Ambinter Stock Screening Collection, Feb. 13, 2008, pp. 1-1, 927548-55-8.
Database CHECATS, 3-Quinolinecarboxamide,2,6-dimethyl-N-[2-(1-Pyrrolidinyl)ethyl)-2-(2thienyl)ethyl], Ambinter Stock Screening Collection, Feb. 13, 2008, pp. 1-1, 1015943-03-9.
Database CHEMCATS, 3-Quinolinecarboxamide,6-chloro-2-methyl-N-[2-(4-morpholinyl)-2-(2-thienyl)ethyl], Ambinater Stock Screening Collection, Feb. 13, 2008, pp. 1-1, 940854-05-7.
Database CHEMCATS, 3-Quinolinecarboxamide,7-Methoxy-2-methyl-N-[2-{4-morpholinyl}-2-(2-thienyl)ethyl], Ukrorgsynthesis Screening Collection, Mar. 6, 2007, pp. 1, 927559-99-7.
Database CHEMCATS, 4-Quinolinecarboxamide,1,2-dihydro N-[2-(4-morpholinyl)-2-(2-thienyl) ethyl]-2-oxo, Ryan Scientific Screening Library, Jan. 25, 2008, pp. 1-1, 924223-35-8.
Database CHEMCATS, 4-Quinolinecarboxamide,2-cycloprppyl-N-[2-(2-furanyl)-2-(1-pyrrolidinyl) ethyl], Ryan Scientific Screening Library, Jan. 25, 2008, pp. 1-1, 930656-70-5.
Database CHEMCATS, 4-Quinolinecarboxamide,N-[2-(2- -furanyl)-2-(1-Pyrrolidinyl) ethyl]-1,2-dihydro-2-oxo, Ryan Scientific Screening Library, Jan. 25, 2008, pp. 1-1, 924218-44-0.
Database CHEMCATS, 4-Quinolinecarboxamide,N-[2-(2-furany)-2(1-Pyrrolidinyl)ethyl]-2(1-methylethyl, Aurora Screening Library, Sep. 6, 2007, pp. 1-1,924386-46-9.
Arbeloa, et al., P2X7 receptor blockade prevents ATP excitotoxicity in neurons and reduces brain damage after ischemia, Neurobiology of Disease, 2012, pp. 954-961, vol. 45.
Arulkumaran, et al., A potential therapeutic role for P2X7 receptor (P2X7R) antagonists in the treatment of inflammatory diseases, Expert Opin Investig, 2011, pp. 897-915, vol. 20 Issue 7.
Avignone, et al., Status Epilepticus Induces a Particular Microglial Activation State Characterized by Enhanced Purinergic Signaling, The Journal of Neuroscience, Sep. 10, 2008, pp. 9133-9144, vol. 28 Issue 37, Society for Neuroscience.
Basso, et al., Behavioral profile of P2X7 receptor knockout mice in animal models of depression and anxiety: Relevance for neuropsychiatric disorders, Behavioural Brain Research, Oct. 18, 2008, pp. 83-90, vol. 198, Elsevier B.V.
Bennet, et al. (Editor), "Part XIV Oncology", Cecil Textbook of Medicine,vol. 1, 20th Edition: pp. 1004-1010 (1996).
Berge, et al, Pharmaceutical Salts, Journal of Pharmaceutical Sciences, 1997, pp. 1-19, vol. 66 Issue 1.
Berge, et al., Pharmaceutical Salts, Journal of Pharmaceutical Sciences, Jan. 1, 1977, pp. 1-19—XP000562636, vol. 66 No. 1, WO.
Bertolini, et al., A New Rational Hypothesis for the Pharmacophore of the Active Metabolite of Leflunomide, a Potent Immunosuppressive Drug, Journal of Medicinal Chemistry, Jan. 17, 1997, pp. 2011-2016, vol. 40 Issue 13.
Bourzac, et al., Glucose Transporter 2 Expression Is Down Regulated Following P2X7 Activation in Enterocytes, Journal of Cellular Physiology, 2013, pp. 120-129, vol. 228.
Bundgaard., Bioreversible derivatives for various functional groups and chemical entities, Design of prodrugs, 1985, pp. 1-3, Chapter 1.
Capuron, et al., Immune system to brain signaling: Neuropsychopharmacological implications, Pharmacology & Therapeutics, 2011, pp. 226-238, vol. 130, Elsevier Inc.
Chessell, et al., Disruption of the P2X7 purinoceptor gene abolishes chronic inflammatory and neuropathic pain, Pain, Jan. 5, 2005, pp. 386-396, vol. 114, Elsevier B.V.
Chu, et al., Inhibition of P2X7 receptor ameliorates transient global cerebral ischemia/reperfusion injury via modulating inflammatory responses in the rat hippocampus, Journal of Neuroinflammation, 2012, pp. 1-10, vol. 9 Issue 69.
Delarasse, et al., The Purinergic Receptor P2X7 Triggers—Secretasedependent Processing of the Amyloid Precursor Protein, The Journal of Biological Chemistry, Nov. 16, 2010, pp. 2596-2606, vol. 286 Issue 4.
Derek Hudson; Methodological Implications of Simultaneous Solid-Phase peptide Synthesis, J.Org.Chem, 1988, pp. 617-624, vol. 53.
Donnelly-Roberts, et al., [3H]A-804598 ([3H]2-cyano-1-[(1S)-1-phenylethyl]-3-quinolin-5-ylguanidine) is a novel, potent, and selective antagonist radioligand for P2X7 receptors, Neuropharmacology, 2009, pp. 223-229, vol. 56.
Duan, et al., P2X7 Receptors: Properties and Relevance to CNS Function, GLIA, 738-746, vol. 54.

(56) References Cited

OTHER PUBLICATIONS

Dyatkin et al, Determination of the Absolute Configuration of a Key Tricyclic Component of a Novel Vasopressin Receptor Antagonist by Use of Vibrational Circular Dichroism, Chirality, 2002, pp. 215-219, vol. 14.
Engel, et al., Seizure suppression and neuroprotection by targeting the purinergic P2X7 receptor during status epilepticus in mice, The FASEB Journal, 2012, pp. 1616-1628, vol. 26.
Ferrari, et al., The P2X7 Receptor: A Key Player in IL-1 Processing and Release1, The Journal of Immunology,, 2006, pp. 3877-3883, vol. 176.
Fleisher, et al., Improved oral drug delivery: solubility limitations overcome by the use of prodrugs, Advanced Drug Delivery Reviews, 1996, pp. 115-130, vol. 19.
Friedle, et al., Recent Patents on Novel P2X7 Receptor Antagonists and their Potential for Reducing Central Nervous System Inflammation, Recent Patents on CNS Drug Discovery, 2010, pp. 35-45, vol. 5.
Furlan-Freguia, et al., P2X7 receptor signaling contributes to tissue factor—dependent thrombosis in mice, The Journal of Clinical Investigation, 2011, pp. 2932-2944, vol. 121 Issue 7.
Glenn D. Considine., Van Nostrand's Encyclopedia of Chemistry,, Encyclopedia of Chemistry, 2005, pp. 261, Chapter 5.
Grygorowicz, et al., Temporal expression of P2X7 purinergic receptor during the course of experimental autoimmune encephalomyelitis, Neurochemistry International, Sep. 9, 2010, pp. 823-829, vol. 57.
Guile, et al., Antagonists of the P2X7 Receptor. From Lead Identification to Drug Development, Journal of Medicinal Chemistry, May 28, 2009, pp. 3123-3141, vol. 52 Issue 10.
Gunosewoyo, et al., P2X purinergic receptor ligands recently patented compounds, Expert Opin. Ther Patents, 2010, pp. 625-646, vol. 20 Issue 5.
Hackam, et al, "Translation of Research Evidence From animals to Humans", JAMA, vol. 296 (14): pp. 1731-1732 (2006).
Hans Bundgaard, Design of Products, Design of Products, 1985, 1-3, 1.
Hernandeza, et al., In vivo P2X7 inhibition reduces amyloid plaques in Alzheimer's disease through GSK3 and secretases, Neurobiology of Aging, 2012, pp. 1816-1828, vol. 33.
Herna'Ndez, et al., Altered P2X7-receptor level and function in mouse models of Huntington's disease and therapeutic efficacy of antagonist administration, The FASEB Journal, 2009, pp. 1893-1906, vol. 23.
Ji, et al., P2X7 deficiency attenuates hypertension and renal injury in deoxycorticosterone acetate-salt hypertension, Am J Physiol Renal Physiol, 2012, pp. F1207-F1215, vol. 303.
Jordan, "Tamoxifen: A Most Unlikely Pioneering Medicine", Nature Reviews, vol. 2: pp. 205-213, (Mar. 2003).
Keating, et al., P2X7 Receptor-Dependent Intestinal Afferent Hypersensitivity in a Mouse Model of Postinfectious Irritable Bowel Syndrome, The Journal of Immunology, Jun. 22, 2011, pp. 1467-1474, vol. 187.
Kenneth D.Bagshawe., Antibody-Directed Enzyme prodrug Therapy : A Review, Drug Development Research, 1995, pp. 220-230, vol. 34.
Killeen, et al., Signaling through purinergic receptors for ATP induce human cutaneous innate and adaptive th17 responses:implications in the pathogenesis of psoriasis, The Journal of Immunology, 2013, pp. 4324-4336, vol. 190.
Kim, et al., Blockade of P2X receptor prevents astroglial death in the dentate gyrus following pilocarpine-induced status epilepticus, Neurological research, 2009, pp. 982-988, vol. 31.
Larsen, A text book of Drug Design and Development, ?, 1991, pp. 1-13, Page Number.
Marcellino, et al., On the role of P2X7 receptors in dopamine nerve cell degeneration in a rat model of Parkinson's disease: studies with the P2X7 receptor antagonist A-438079, J Neural Transm, Apr. 13, 2010, pp. 681-687, vol. 117.
Martins, et al., The role of P2X7 purinergic receptors in inflammatory and nociceptive changes accompanying cyclophosphamide-induced haemorrhagic cystitis in mice, British Journal of Pharmacology, 2012, pp. 183-196, vol. 165.
Muller, et al., Apotential role for P2X7r in allergic airway inflammation in mice and humans, American Journal of Respiratory Cell and molecular Biology, 2011, pp. 456-464; vol. 44.
Nicholas Bodor., Novel Approaches to the Design of Safer Drugs: Soft Drugs and Site-Specific Chemical Delivery Systems, Advances in Drug Research, 1984, pp. 256-331, vol. 13.
Oyanguren-Desez, et al., Gain-of-function of P2X7 receptor gene variants in multiple sclerosis, Cell Calcium, Sep. 8, 2011, pp. 468-472, vol. 50.
Parvathenani, et al., P2X7 Mediates Superoxide Production in Primary Microglia and Is Up-regulated in a Transgenic Mouse Model of Alzheimer's Disease, The Journal of Biological Chemistry, Jan. 27, 2003, pp. 13309-13317, vol. 278 Issue 15.
Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.
Robert Dantzer., Cytokine, Sickness Behavior, and Depression, Immunol Allergy Clin N Am, 2009, pp. 247-264, Volime 29.
Robinson, et al., Discovery of the Hemifumarate and (r-L-Alanyloxy)methyl Ether as Prodrugs of an Antirheumatic Oxindole: Prodrugs for the Enolic OH Group, Journal of Medicinal Chemistry, 1996, pp. 10-18, vol. 39 Issue 1.
Romagnoli, et al., The P2X 7 receptor as a therapeutic target, Expert Opin. Ther., 2008, pp. 647-661, vol. 15 Issue 5.
Rudolph, et al., Novel methyl substituted 1-(5,6-dihydro-[1,2,4]triazolo [4,3-a]pyrazin-7(8H)-yl)methanones are P2X7 antagonists, Bioorganic & Medicinal Chemistry Letters, Jun. 9, 2015, pp. 3157-3163, vol. 25.
Sanz, et al., Activation of Microglia by Amyloid Requires P2X7 Receptor Expression1, The Journal of Immunology, 2009, pp. 4378-4385, vol. 182.
Shan, et al., Prodrug Strategies Based on Intramolecular Cyclization Reactions, Journal of Pharmaceutical Sciences, Jul. 1977, pp. 765-767, vol. 86 issue 7.
Sharp, et al., P2x7 deficiency suppresses development of experimental autoimmune encephalomyelitis; Journal of Neuroinflammation, Aug. 8, 2008, pp. 1-13, vol. 5 Issue 33.
Skaper, et al., The P2X7 purinergic receptor: from physiology to neurological disorders, The FASEB Journal, 2010, pp. 337-345, vol. 24.
Solini, et al., Enhanced P2X7 Activity in Human Fibroblasts From Diabetic Patients a Possible Pathogenetic Mechanism for Vascular Damage in Diabetes, Arterioscler Thromb Vasc Biol., 2004, pp. 1240-1245, vol. 24.
Stahl, et al., Handbook of Pharmaceutical Salts, International Union of pure and Applied Chemistry, 2002, pp. 1-3, Page Number.
Surprenant, et al., Signaling at Purinergic P2X Receptors, Annu. Rev. Physiol, Oct. 13, 2008, pp. 333-359, vol. 71.
Thiboutot, et al., Inflammasome Activation by propionibacterium acnes: the Story of IL-1 in Acne continues to unfold, Journal of Investigative Dermatology, 2014, pp. 595-597, vol. 134.
V. Craig Jordan, "Tamoxifen: A Most Unlikely Pioneering Medicine", Nature Reviews Drug Discovery, 2003, pp. 205-213, vol. 2.
Vergani, et al., Effects of the purinergic Inhibitor Oxidized ATP in a model of Islet Allograft rejection, Diabetes, 2013, pp. 1665-1675, vol. 62.
Vergani, et al., Long term Heart Transplant Survival by targeting the Ionotropic Purinergic receptor P2X7, Circulation, 2013, pp. 463-475, vol. 127.

* cited by examiner

P2X7 MODULATORS

FIELD OF THE INVENTION

The present invention is related to compounds having P2X7 modulating properties, pharmaceutical compositions comprising these compounds, chemical processes for preparing these compounds, and their use in the treatment of diseases associated with P2X7 receptor activity in animals, in particular humans.

BACKGROUND OF THE INVENTION

The P2X7 receptor is a ligand-gated ion channel and is present on a variety of cell types, largely those known to be involved in the inflammatory and/or immune process, specifically, macrophages and monocytes in the periphery and predominantly in glial cells (microglia and astrocytes) of the CNS. (Duan and Neary, *Glia* 2006, 54, 738-746; Skaper et al., *FASEB J* 2009, 24, 337-345; Surprenant and North, *Annu. Rev. Physiol.* 2009, 71, 333-359). Activation of the P2X7 receptor by extracellular nucleotides, in particular adenosine triphosphate, leads to the release of proinflammatory cytokines IL-1β and IL-18 (Muller, et. Al. *Am. J. Respir. Cell Mol. Biol.* 2011, 44, 456-464), giant cell formation (macrophages/microglial cells), degranulation (mast cells) and L-selectin shedding (lymphocytes) (Ferrari et al., *J. Immunol.* 2006, 176, 3877-3883; Surprenant and North, *Annu. Rev. Physiol.* 2009, 71, 333-359). P2X7 receptors are also located on antigen-presenting cells (keratinocytes, salivary acinar cells (parotid cells)), hepatocytes, erythrocytes, erythroleukaemic cells, monocytes, fibroblasts, bone marrow cells, neurones, and renal mesangial cells.

The importance of P2X7 in the nervous system arises primarily from experiments using P2X7 knockout mice. These mice demonstrate the role of P2X7 in the development and maintenance of pain, as these mice are protected from the development of both adjuvant-induced inflammatory pain and partial nerve ligation-induced neuropathic pain (Chessell et al., *Pain* 2005, 114, 386-396). In addition, P2X7 knockout mice also exhibit an anti-depressant phenotype based on reduced immobility in forced swim and tail suspension tests (Basso et al., *Behav. Brain Res.* 2009, 198, 83-90.). Moreover, the P2X7 pathway is linked to the release of the pro-inflammatory cytokine, IL-1β, which has been linked to precipitation of mood disorders in humans (Dantzer, *Immunol. Allergy Clin. North Am.* 2009, 29, 247-264; Capuron and Miller, *Pharmacol. Ther.* 2011, 130, 226-238). In addition, in murine models of Alzheimer's disease, P2X7 was upregulated around amyloid plaques, indicating a role of this target in such pathology as well (Parvathenani et al., *J. Biol. Chem.* 2003, 278, 13309-13317).

Several reviews on small molecule inhibitors of P2X7 which have been published are: Guile, S. D., et al., J. Med. Chem, 2009, 52, 3123-3141; Gunosewoyo, H. and Kassiou, M., Exp Opin, 2010, 20, 625-646.

In view of the clinical importance of P2X7, the identification of compounds that modulate P2X7 receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

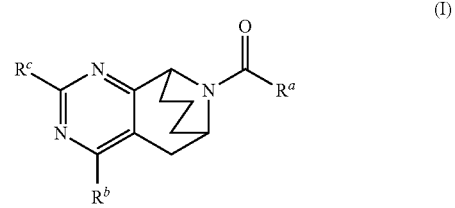

and enantiomers or diastereomers thereof;
and pharmaceutically acceptable salts thereof;
wherein:
$R^a$ is

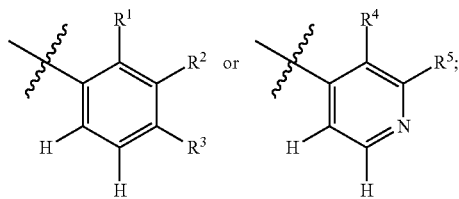

$R^1$, $R^2$, $R^3$, and $R^4$ are each independently selected from the group consisting of: H, halo, $C_1$-$C_3$alkyl and $C_1$-$C_3$perhaloalkyl;
$R^5$ is $C_1$-$C_3$perhaloalkyl or $C_1$-$C_3$alkyl;
$R^b$ is selected from the group consisting of:

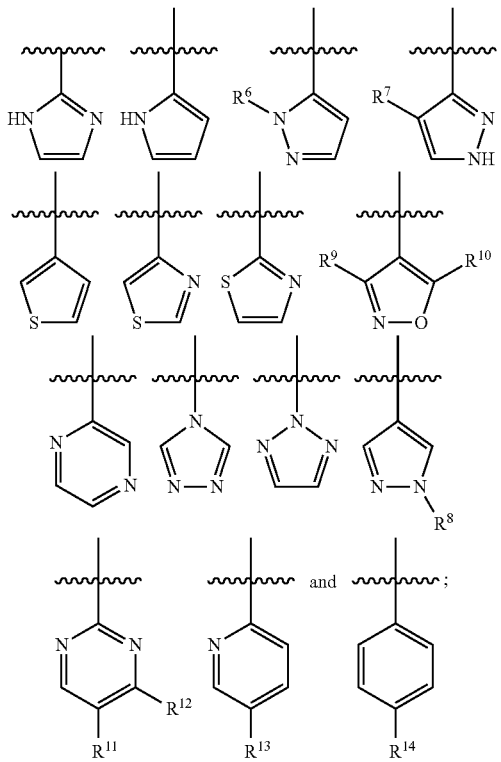

Wherein:
$R^6$, $R^8$, $R^9$, $R^{10}$, $R^{12}$, $R^{13}$ are independently H or $C_1$-$C_3$alkyl,
$R^7$ is H, halo or $C_1$-$C_3$perhaloalkyl,
$R^{11}$ is H, halo or OH;
$R^{14}$ is H or halo; and
$R^c$ is selected from the group consisting of: H, $NH_2$, $C_1$-$C_4$alkyl.

Further embodiments are provided by pharmaceutically acceptable salts of compounds of Formulas (I), pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula I, as well as the pharmaceutically acceptable salts.

In a further aspect, the invention relates to pharmaceutical compositions for treating a disease, disorder, or medical condition mediated by P2X7 receptor activity, comprising an effective amount of at least one compound selected from compounds of Formula (I), pharmaceutically acceptable salts of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as P2X7 receptor modulators. Thus, the invention is directed to a method for modulating P2X7 receptor activity, including when such receptor is in a subject, comprising exposing P2X7 receptor to an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by P2X7 receptor activity, comprising administering to the subject in need of such treatment an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

Additional embodiments of this invention include methods of making compounds of Formula (I), pharmaceutically acceptable salts of compounds of Formula (I), pharmaceutically acceptable prodrugs of compounds of Formula (I), and pharmaceutically active metabolites of Formula (I).

DETAILED DESCRIPTION OF THE INVENTION

A compound of Formula (I):

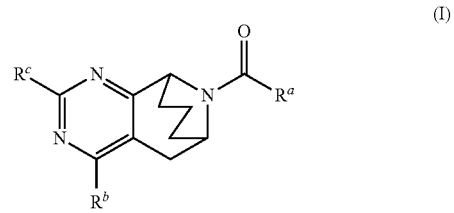

and enantiomers or diastereomers thereof;
and pharmaceutically acceptable salts thereof;
wherein:
$R^a$ is

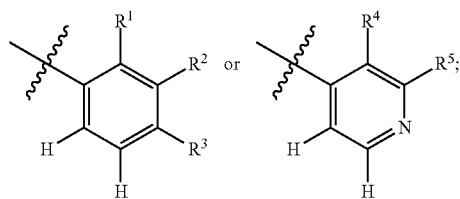

$R^1$, $R^2$, $R^3$, and $R^4$ are each independently selected from the group consisting of: H, halo, $C_1$-$C_3$alkyl and $C_1$-$C_3$perhaloalkyl;
$R^5$ is $C_1$-$C_3$perhaloalkyl or $C_1$-$C_3$alkyl;
$R^b$ is selected from the group consisting of:

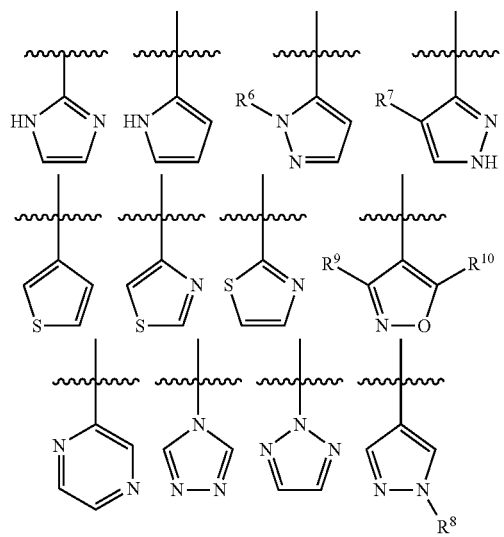

-continued

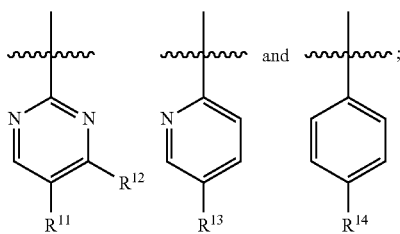

Wherein:
$R^6$, $R^8$, $R^9$, $R^{10}$, $R^{12}$, $R^{13}$ are independently H or $C_1$-$C_3$alkyl,
$R^7$ is H, halo or $C_1$-$C_3$perhaloalkyl,
$R^{11}$ is H, halo or OH;
$R^{14}$ is H or halo; and
$R^c$ is selected from the group consisting of: H, $NH_2$, $C_1$-$C_4$alkyl.

An additional embodiment of the invention is a compound of Formula (I) wherein $R^a$ is

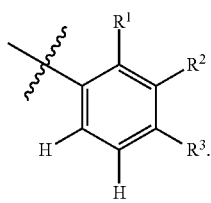

An additional embodiment of the invention is a compound of Formula (I) wherein $R^a$ is

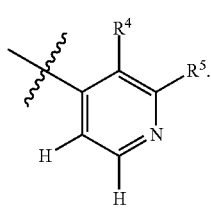

An additional embodiment of the invention is a compound of Formula (I) wherein is $R^a$ is

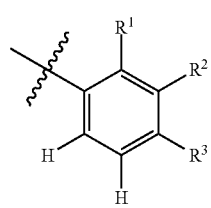

and $R^1$ is independently selected from the group consisting of: halo, $C_1$-$C_3$alkyl and $C_1$-$C_3$perhaloalkyl.

An additional embodiment of the invention is a compound of Formula (I) wherein is $R^a$ is

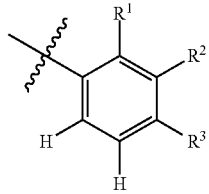

and $R^1$ is independently selected from the group consisting of: halo and $C_1$-$C_3$perhaloalkyl.

An additional embodiment of the invention is a compound of Formula (I) wherein is $R^a$ is

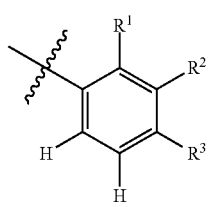

and $R^1$ is halo.

An additional embodiment of the invention is a compound of Formula (I) wherein is $R^a$ is

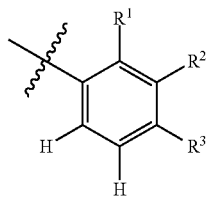

and $R^2$ is independently selected from the group consisting of: halo, $C_1$-$C_3$alkyl and $C_1$-$C_3$perhaloalkyl.

An additional embodiment of the invention is a compound of Formula (I) wherein is $R^a$ is

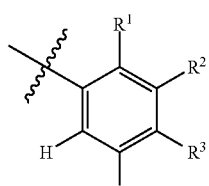

and $R^2$ is independently selected from the group consisting of: halo and $C_1$-$C_3$perhaloalkyl.

An additional embodiment of the invention is a compound of Formula (I) wherein is $R^a$ is

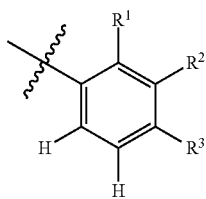

and $R^2$ is $C_1$-$C_3$perhaloalkyl.

An additional embodiment of the invention is a compound of Formula (I) wherein is $R^a$ is

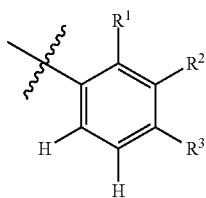

and $R^3$ is independently selected from the group consisting of: H, halo, and $C_1$-$C_3$perhaloalkyl.

An additional embodiment of the invention is a compound of Formula (I) wherein is $R^a$ is

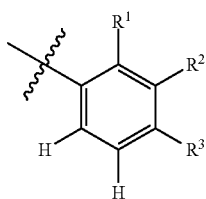

and $R^3$ is independently selected from the group consisting of: H and halo.

An additional embodiment of the invention is a compound of Formula (I) wherein is $R^a$ is

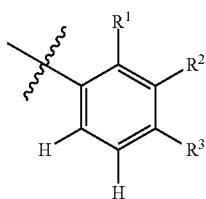

and $R^3$ is halo.

An additional embodiment of the invention is a compound of Formula (I) wherein is $R^a$ is

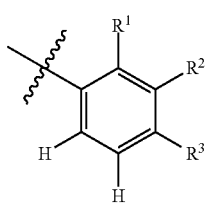

and $R^1$ is independently selected from the group consisting of: halo, $C_1$-$C_3$alkyl and $C_1$-$C_3$perhaloalkyl and $R^2$ is independently selected from the group consisting of: halo, $C_1$-$C_3$alkyl and $C_1$-$C_3$perhaloalkyl.

An additional embodiment of the invention is a compound of Formula (I) wherein is $R^a$ is

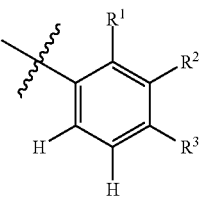

and $R^1$ is independently selected from the group consisting of: halo, $C_1$-$C_3$alkyl and $C_1$-$C_3$perhaloalkyl, $R^2$ is independently selected from the group consisting of: halo, $C_1$-$C_3$alkyl and $C_1$-$C_3$perhaloalkyl and $R^3$ is H or halo.

An additional embodiment of the invention is a compound of Formula (I) wherein is $R^a$ is

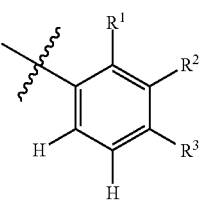

and $R^1$ is independently selected from the group consisting of: halo and $C_1$-$C_3$perhaloalkyl and $R^2$ is independently selected from the group consisting of: halo and $C_1$-$C_3$perhaloalkyl.

An additional embodiment of the invention is a compound of Formula (I) wherein is $R^a$ is

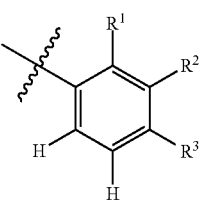

and $R^1$ is independently selected from the group consisting of: halo and $C_1$-$C_3$perhaloalkyl and $R^2$ is independently selected from the group consisting of: halo and $C_1$-$C_3$perhaloalkyl, and $R^3$ is H.

An additional embodiment of the invention is a compound of Formula (I) wherein is $R^a$ is

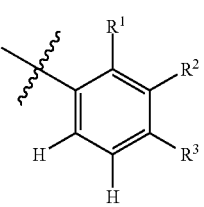

and $R^1$ is halo and $R^2$ is $C_1$-$C_3$perhaloalkyl.

An additional embodiment of the invention is a compound of Formula (I) wherein is $R^a$ is

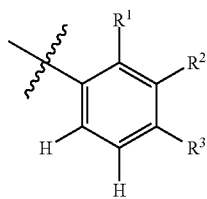

and $R^1$ is halo, $R^2$ is $C_1$-$C_3$perhaloalkyl and $R^3$ is H.

An additional embodiment of the invention is a compound of Formula (I) wherein is $R^a$ is

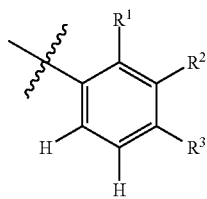

and $R^1$ and $R^2$ are halo.

An additional embodiment of the invention is a compound of Formula (I) wherein is $R^a$ is

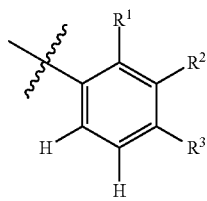

and $R^1$ and $R^2$ are halo and $R^3$ is H.

An additional embodiment of the invention is a compound of Formula (I) wherein is $R^a$ is

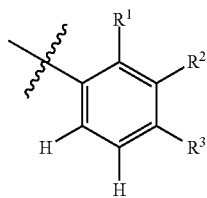

and $R^1$, $R^2$ and $R^3$ are halo.

An additional embodiment of the invention is a compound of Formula (I) wherein $R^a$ is

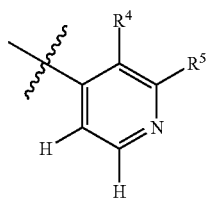

and $R^4$ is independently selected from the group consisting of: halo, $C_1$-$C_3$alkyl and $C_1$-$C_3$perhaloalkyl.

An additional embodiment of the invention is a compound of Formula (I) wherein $R^a$ is

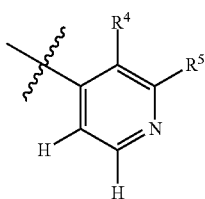

and $R^4$ is independently selected from the group consisting of: halo and $C_1$-$C_3$perhaloalkyl.

An additional embodiment of the invention is a compound of Formula (I) wherein $R^a$ is

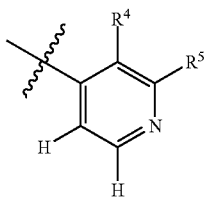

and $R^4$ is halo.

An additional embodiment of the invention is a compound of Formula (I) wherein $R^a$ is

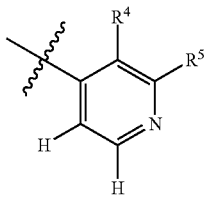

and $R^5$ is $C_1$-$C_3$alkyl or $C_1$-$C_3$perhaloalkyl.

An additional embodiment of the invention is a compound of Formula (I) wherein $R^a$ is

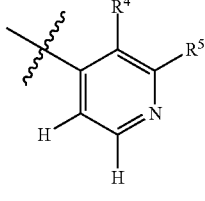

and $R^5$ is $C_1$-$C_3$perhaloalkyl.

An additional embodiment of the invention is a compound of Formula (I) wherein $R^a$ is

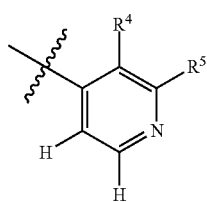

and R⁴ is independently selected from the group consisting of: halo, $C_1$-$C_3$alkyl and $C_1$-$C_3$perhaloalkyl and R⁵ is $C_1$-$C_3$alkyl or $C_1$-$C_3$perhaloalkyl.

An additional embodiment of the invention is a compound of Formula (I) wherein $R^a$ is

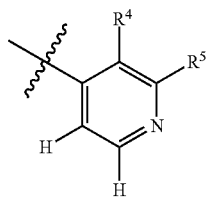

and R⁴ is independently selected from the group consisting of: halo and $C_1$-$C_3$perhaloalkyl and R⁵ is $C_1$-$C_3$perhaloalkyl.

An additional embodiment of the invention is a compound of Formula (I) wherein $R^a$ is

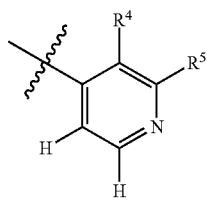

and R⁴ is halo and R⁵ is $C_1$-$C_3$perhaloalkyl.

An additional embodiment of the invention is a compound of Formula (I) wherein $R^b$ is selected from the group consisting of:

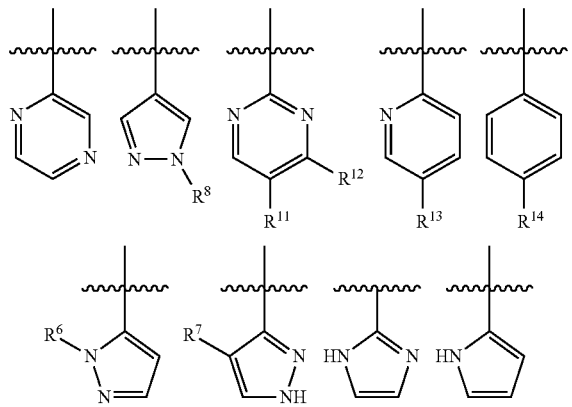

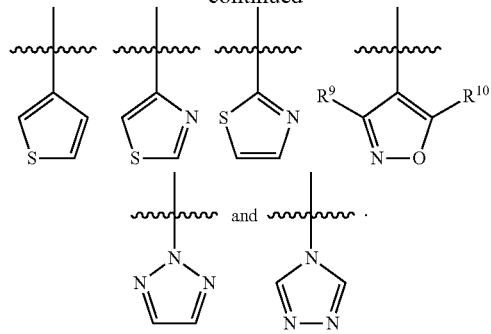

An additional embodiment of the invention is a compound of Formula (I) wherein $R^b$ is selected from the group consisting of:

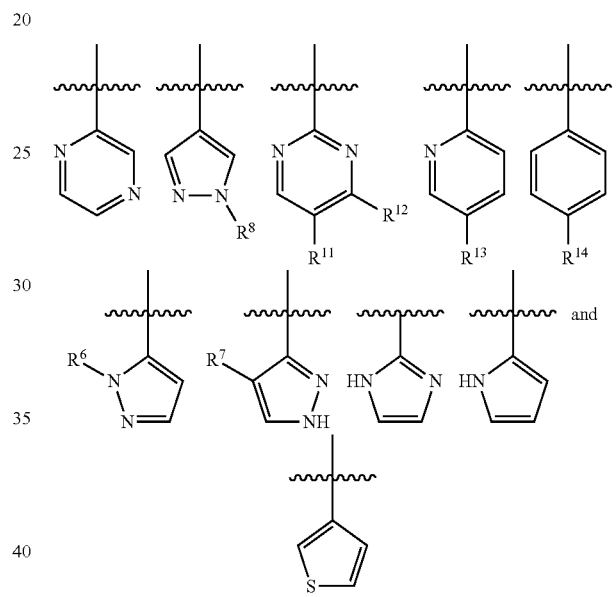

An additional embodiment of the invention is a compound of Formula (I) wherein $R^b$ is selected from the group consisting of:

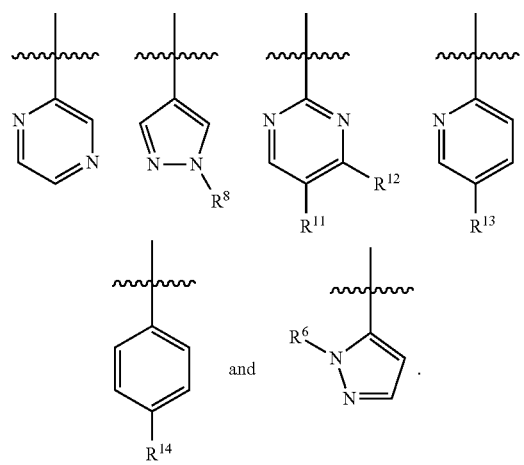

An additional embodiment of the invention is a compound of Formula (I) wherein $R^b$ is selected from the group consisting of:

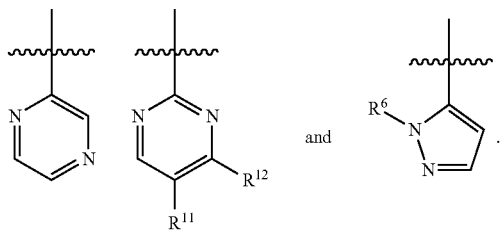

and

An additional embodiment of the invention is a compound of Formula (I) wherein $R^b$ is:

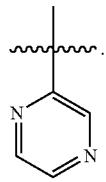

An additional embodiment of the invention is a compound of Formula (I) wherein $R^b$ is

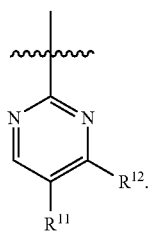

An additional embodiment of the invention is a compound of Formula (I) wherein $R^b$ is

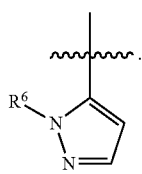

An additional embodiment of the invention is a compound of Formula (I) wherein $R^c$ is selected from the group consisting of: H, $NH_2$, and $C_1$-$C_4$alkyl;

An additional embodiment of the invention is a compound of Formula (I) wherein $R^c$ is H or $C_1$-$C_4$alkyl.

An additional embodiment of the invention is a compound of Formula (I) wherein $R^c$ is $C_1$-$C_4$alkyl.

An additional embodiment of the invention is a compound of Formula (I) wherein $R^a$ is

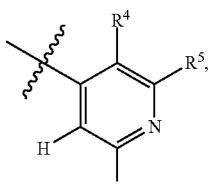

$R^4$ is halo, $R^5$ is $C_1$-$C_3$perhaloalkyl, $R^c$ is $C_1$-$C_4$alkyl, $R^6$ is H, $R^b$ is

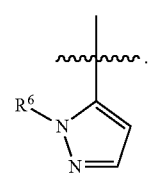

An additional embodiment of the invention is a compound of Formula (I) wherein $R^a$ is

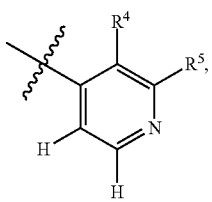

$R^4$ is halo, $R^5$ is $C_1$-$C_3$perhaloalkyl, $R^c$ is $C_1$-$C_4$alkyl, $R^6$ is $CH_3$, $R^b$ is

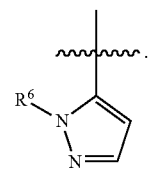

An additional embodiment of the invention is a compound of Formula (I) wherein is $R^a$ is

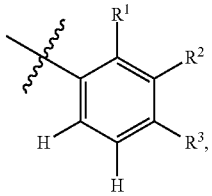

$R^1$ is halo, $R^2$ is $C_1$-$C_3$perhaloalkyl, $R^3$ is H, $R^c$ is $C_1$-$C_4$alkyl, $R^6$ is H, $R^b$ is

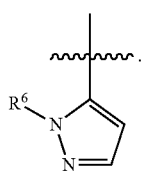

An additional embodiment of the invention is a compound of Formula (I) wherein is $R^a$ is

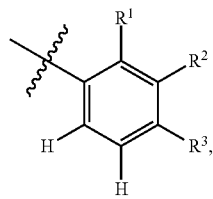

$R^1$ is halo, $R^2$ is $C_1$-$C_3$perhaloalkyl, $R^3$ is H, $R^c$ is $C_1$-$C_4$alkyl, $R^{11}$ and $R^{12}$ are H, $R^b$ is

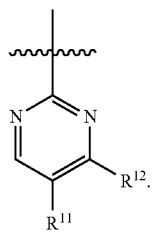

An additional embodiment of the invention is a compound of Formula (I) wherein is $R^a$ is

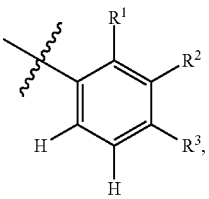

$R^1$ is halo, $R^2$ is $C_1$-$C_3$perhaloalkyl, $R^3$ is H, $R^c$ is $C_1$-$C_4$alkyl, and $R^b$ is

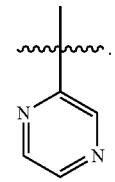

An additional embodiment of the invention is a compound listed in Table 1.

TABLE 1

(2,3-dichlorophenyl)(2-methyl-4-(1H-pyrazol-5-yl)-5,6,7,8,9,10-hexahydro-6,10-epiminocycloocta[d]pyrimidin-11-yl)methanone
(2-chloro-3-(trifluoromethyl)phenyl)(2-methyl-4-(1 H-pyrazol-5-yl)-5,6,7,8,9,10-hexahydro-6,10-epiminocycloocta[d]pyrimidin-11-yl)methanone
(2-chloro-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone
(2,3-dichloro-4-fluorophenyl)((6R,10S)-2-methyl-4-(1H-pyrazol-5-yl)-5,6,7,8,9,10-hexahydro-6,10-epiminocycloocta[d]pyrimidin-11-yl)methanone
(2,4-dichlorophenyl)((6R,10S)-2-methyl-4-(1H-pyrazol-5-yl)-5,6,7,8,9,10-hexahydro-6,10-epiminocycloocta[d]pyrimidin-11-yl)methanone
(2-methyl-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone
(3-chloro-2-(trifluoromethyl)pyridin-4-yl)((6R,10S)-2-methyl-4-(1H-pyrazol-5-yl)-5,6,7,8,9,10-hexahydro-6,10-epiminocycloocta[d]pyrimidin-11-yl)methanone
(2-fluoro-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone
(2-chloro-4-fluorophenyl)((6R,10S)-2-methyl-4-(1H-pyrazol-5-yl)-5,6,7,8,9,10-hexahydro-6,10-epiminocycloocta[d]pyrimidin-11-yl)methanone
(2,4-dichloro-3-fluorophenyl)((6R,10S)-2-methyl-4-(1H-pyrazol-5-yl)-5,6,7,8,9,10-hexahydro-6,10-epiminocycloocta[d]pyrimidin-11-yl)methanone
(2,3-dichlorophenyl)((6R,10S)-2-methyl-4-(1H-pyrazol-5-yl)-5,6,7,8,9,10-hexahydro-6,10-epiminocycloocta[d]pyrimidin-11-yl)methanone
(4-chloro-2-fluorophenyl)((6R,10S)-2-methyl-4-(1H-pyrazol-5-yl)-5,6,7,8,9,10-hexahydro-6,10-epiminocycloocta[d]pyrimidin-11-yl)methanone
(2-chloro-3-(trifluoromethyl)phenyl)((6R,10S)-4-(4-fluorophenyl)-2-methyl-5,6,7,8,9,10-hexahydro-6,10-epiminocycloocta[d]pyrimidin-11-yl)methanone
((6R,10S)-4-(4-fluorophenyl)-2-methyl-5,6,7,8,9,10-hexahydro-6,10-epiminocycloocta[d]pyrimidin-11-yl)(2-methyl-3-(trifluoromethyl)phenyl)methanone
(2,4-dichlorophenyl)((6R,10S)-4-(4-fluorophenyl)-2-methyl-5,6,7,8,9,10-hexahydro-6,10-epiminocycloocta[d]pyrimidin-11-yl)methanone
(2-chloro-4-fluorophenyl)((6R,10S)-4-(4-fluorophenyl)-2-methyl-5,6,7,8,9,10-hexahydro-6,10-epiminocycloocta[d]pyrimidin-11-yl)methanone TABLE 1-continued (2,3-dichloro-4-fluorophenyl)((6R,10S)-4-(4-fluorophenyl)-2-methyl-5,6,7,8,9,10-hexahydro-6,10-epiminocycloocta[d]pyrimidin-11-yl)methanone
(3-chloro-2-(trifluoromethyl)pyridin-4-yl)((6R,10S)-4-(4-fluorophenyl)-2-methyl-5,6,7,8,9,10-hexahydro-6,10-epiminocycloocta[d]pyrimidin-11-yl)methanone
(2-chloro-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone
(2,4-dichlorophenyl)((6S,10R)-2-methyl-4-(1H-pyrazol-5-yl)-5,6,7,8,9,10-hexahydro-6,10-epiminocycloocta[d]pyrimidin-11-yl)methanone
(2-methyl-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone
(2-chloro-4-fluorophenyl)((6S,10R)-2-methyl-4-(1H-pyrazol-5-yl)-5,6,7,8,9,10-hexahydro-6,10-epiminocycloocta[d]pyrimidin-11-yl)methanone
(2,4-dichloro-3-fluorophenyl)((6S,10R)-2-methyl-4-(1H-pyrazol-5-yl)-5,6,7,8,9,10-hexahydro-6,10-epiminocycloocta[d]pyrimidin-11-yl)methanone
(3-chloro-2-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone
(2,3-dichloro-4-fluorophenyl)((6S,10R)-2-methyl-4-(1H-pyrazol-5-yl)-5,6,7,8,9,10-hexahydro-6,10-epiminocycloocta[d]pyrimidin-11-yl)methanone
(2-fluoro-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone
(3-fluoro-2-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone
(4-chloro-2-fluorophenyl)((6S,10R)-2-methyl-4-(1H-pyrazol-5-yl)-5,6,7,8,9,10-hexahydro-6,10-epiminocycloocta[d]pyrimidin-11-yl)methanone
(2,3-dichlorophenyl)((6S,10R)-2-methyl-4-(1H-pyrazol-5-yl)-5,6,7,8,9,10-hexahydro-6,10-epiminocycloocta[d]pyrimidin-11-yl)methanone
(2-chloro-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(2,3-dichlorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(3-chloro-2-(trifluoromethyl)pyridin-4-yl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(2,3-dichloro-4-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(2-fluoro-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(2,4-dichloro-3-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(2-chloro-4-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(3-fluoro-2-(trifluoromethyl)pyridin-4-yl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(4-chloro-2-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(2-methyl-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(2,4-dichlorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone
(2-chloro-3-(trifluoromethyl)phenyl)((6S,10R)-2-methyl-4-(pyrimidin-2-yl)-5,6,7,8,9,10-hexahydro-6,10-epiminocycloocta[d]pyrimidin-11-yl)methanone
(3-chloro-2-(trifluoromethyl)pyridin-4-yl)((6S,10R)-2-methyl-4-(pyrimidin-2-yl)-5,6,7,8,9,10-hexahydro-6,10-epiminocycloocta[d]pyrimidin-11-yl)methanone
(2-methyl-3-(trifluoromethyl)phenyl)((6S,10R)-2-methyl-4-(pyrimidin-2-yl)-5,6,7,8,9,10-hexahydro-6,10-epiminocycloocta[d]pyrimidin-11-yl)methanone
(2,4-dichloro-3-fluorophenyl)((6S,10R)-2-methyl-4-(pyrimidin-2-yl)-5,6,7,8,9,10-hexahydro-6,10-epiminocycloocta[d]pyrimidin-11-yl)methanone
(2,3-dichlorophenyl)((6S,10R)-2-methyl-4-(pyrimidin-2-yl)-5,6,7,8,9,10-hexahydro-6,10-epiminocycloocta[d]pyrimidin-11-yl)methanone
(2-chloro-3-(trifluoromethyl)phenyl)((6S,10R)-2-methyl-4-(pyrazin-2-yl)-5,6,7,8,9,10-hexahydro-6,10-epiminocycloocta[d]pyrimidin-11-yl)methanone
(2,4-dichloro-3-fluorophenyl)((6S,10R)-2-methyl-4-(pyrazin-2-yl)-5,6,7,8,9,10-hexahydro-6,10-epiminocycloocta[d]pyrimidin-11-yl)methanone
(2,3-dichlorophenyl)((6S,10R)-2-methyl-4-(pyrazin-2-yl)-5,6,7,8,9,10-hexahydro-6,10-epiminocycloocta[d]pyrimidin-11-yl)methanone
(3-chloro-2-(trifluoromethyl)pyridin-4-yl)((6S,10R)-2-methyl-4-(pyrazin-2-yl)-5,6,7,8,9,10-hexahydro-6,10-epiminocycloocta[d]pyrimidin-11-yl)methanone
(2-methyl-3-(trifluoromethyl)phenyl)((6S,10R)-2-methyl-4-(pyrazin-2-yl)-5,6,7,8,9,10-hexahydro-6,10-epiminocycloocta[d]pyrimidin-11-yl)methanone
(2-chloro-3-(trifluoromethyl)phenyl)((6S,10R)-4-(4-fluorophenyl)-2-methyl-5,6,7,8,9,10-hexahydro-6,10-epiminocycloocta[d]pyrimidin-11-yl)methanone
(3-chloro-2-(trifluoromethyl)pyridin-4-yl)((6S,10R)-4-(4-fluorophenyl)-2-methyl-5,6,7,8,9,10-hexahydro-6,10-epiminocycloocta[d]pyrimidin-11-yl)methanone
((6S,10R)-4-(4-fluorophenyl)-2-methyl-5,6,7,8,9,10-hexahydro-6,10-epiminocycloocta[d]pyrimidin-11-yl)(2-methyl-3-(trifluoromethyl)phenyl)methanone TABLE 1-continued (2,4-dichloro-3-fluorophenyl)((6S,10R)-4-(4-fluorophenyl)-2-methyl-5,6,7,8,9,10-
hexahydro-6,10-epiminocycloocta[d]pyrimidin-11-yl)methanone
(2,3-dichlorophenyl)((6S,10R)-4-(4-fluorophenyl)-2-methyl-5,6,7,8,9,10-
hexahydro-6,10-epiminocycloocta[d]pyrimidin-11-yl)methanone
(2-chloro-3-(trifluoromethyl)phenyl)((6S,10R)-2-methyl-4-(1-methyl-1H-pyrazol-
5-yl)-5,6,7,8,9,10-hexahydro-6,10-epiminocycloocta[d]pyrimidin-11-
yl)methanone
(2-methyl-3-(trifluoromethyl)phenyl)((6S,10R)-2-methyl-4-(1-methyl-1H-pyrazol-
5-yl)-5,6,7,8,9,10-hexahydro-6,10-epiminocycloocta[d]pyrimidin-11-
yl)methanone
(2,4-dichloro-3-fluorophenyl)((6S,10R)-2-methyl-4-(1-methyl-1H-pyrazol-5-yl)-
5,6,7,8,9,10-hexahydro-6,10-epiminocycloocta[d]pyrimidin-11-yl)methanone
(2,3-dichlorophenyl)((6S,10R)-2-methyl-4-(1-methyl-1H-pyrazol-5-yl)-
5,6,7,8,9,10-hexahydro-6,10-epiminocycloocta[d]pyrimidin-11-yl)methanone
(3-chloro-2-(trifluoromethyl)pyridin-4-yl)((6S,10R)-2-methyl-4-(1-methyl-1H-
pyrazol-5-yl)-5,6,7,8,9,10-hexahydro-6,10-epiminocycloocta[d]pyrimidin-11-
yl)methanone
(3-chloro-2-(trifluoromethyl)pyridin-4-yl)((6S,10R)-2-methyl-4-(pyridin-2-yl)-
5,6,7,8,9,10-hexahydro-6,10-epiminocycloocta[d]pyrimidin-11-yl)methanone
(2-methyl-3-(trifluoromethyl)phenyl)((6S,10R)-2-methyl-4-(pyridin-2-yl)-
5,6,7,8,9,10-hexahydro-6,10-epiminocycloocta[d]pyrimidin-11-yl)methanone
(2-chloro-3-(trifluoromethyl)phenyl)((6S,10R)-2-methyl-4-(pyridin-2-yl)-
5,6,7,8,9,10-hexahydro-6,10-epiminocycloocta[d]pyrimidin-11-yl)methanone
(2,4-dichloro-3-fluorophenyl)((6S,10R)-2-methyl-4-(pyridin-2-yl)-5,6,7,8,9,10-
hexahydro-6,10-epiminocycloocta[d]pyrimidin-11-yl)methanone
(2,3-dichlorophenyl)((6S,10R)-2-methyl-4-(pyridin-2-yl)-5,6,7,8,9,10-hexahydro-
6,10-epiminocycloocta[d]pyrimidin-11-yl)methanone
(2-amino-4-(1H-pyrazol-3-yl)-5,6,7,8,9,10-hexahydro-6,10-
epiminocycloocta[d]pyrimidin-11-yl)(2-chloro-3-
(trifluoromethyl)phenyl)methanone
(4-(1H-pyrazol-3-yl)-5,6,7,8,9,10-hexahydro-6,10-epiminocycloocta[d]pyrimidin-
11-yl)(2-chloro-3-(trifluoromethyl)phenyl)methanone
(2-chloro-3-(trifluoromethyl)phenyl)(2-isopropyl-4-(1H-pyrazol-3-yl)-5,6,7,8,9,10-
hexahydro-6,10-epiminocycloocta[d]pyrimidin-11-yl)methanone
(2-chloro-3-(trifluoromethyl)phenyl)(2-ethyl-4-(1H-pyrazol-3-yl)-5,6,7,8,9,10-
hexahydro-6,10-epiminocycloocta[d]pyrimidin-11-yl)methanone
(2-chloro-3-(trifluoromethyl)phenyl)(2-methyl-4-(2H-1,2,3-triazol-2-yl)-
5,6,7,8,9,10-hexahydro-6,10-epiminocycloocta[d]pyrimidin-11-yl)methanone
(2-chloro-3-(trifluoromethyl)phenyl)(4-(4-fluoro-1H-pyrazol-3-yl)-2-methyl-
5,6,7,8,9,10-hexahydro-6,10-epiminocycloocta[d]pyrimidin-11-yl)methanone
(2-chloro-3-(trifluoromethyl)phenyl)(2-methyl-4-(4-(trifluoromethyl)-1H-pyrazol-3-
yl)-5,6,7,8,9,10-hexahydro-6,10-epiminocycloocta[d]pyrimidin-11-yl)methanone
(2-chloro-3-(trifluoromethyl)phenyl)(4-(3,5-dimethylisoxazol-4-yl)-2-methyl-
5,6,7,8,9,10-hexahydro-6,10-epiminocycloocta[d]pyrimidin-11-yl)methanone
(4-(1H-imidazol-2-yl)-2-methyl-5,6,7,8,9,10-hexahydro-6,10-
epiminocycloocta[d]pyrimidin-11-yl)(2-chloro-3-
(trifluoromethyl)phenyl)methanone
(2-chloro-3-(trifluoromethyl)phenyl)(2-methyl-4-(thiazol-2-yl)-5,6,7,8,9,10-
hexahydro-6,10-epiminocycloocta[d]pyrimidin-11-yl)methanone
(2-chloro-3-(trifluoromethyl)phenyl)(2-methyl-4-(1H-pyrrol-2-yl)-5,6,7,8,9,10-
hexahydro-6,10-epiminocycloocta[d]pyrimidin-11-yl)methanone
(2-chloro-3-(trifluoromethyl)phenyl)(2-methyl-4-(thiazol-4-yl)-5,6,7,8,9,10-
hexahydro-6,10-epiminocycloocta[d]pyrimidin-11-yl)methanone
(2-chloro-3-(trifluoromethyl)phenyl)(4-(isoxazol-4-yl)-2-methyl-5,6,7,8,9,10-
hexahydro-6,10-epiminocycloocta[d]pyrimidin-11-yl)methanone
(2-chloro-3-(trifluoromethyl)phenyl)(2-methyl-4-(thiophen-3-yl)-5,6,7,8,9,10-
hexahydro-6,10-epiminocycloocta[d]pyrimidin-11-yl)methanone
(2-chloro-3-(trifluoromethyl)phenyl)(2-methyl-4-(4H-1,2,4-triazol-4-yl)-
5,6,7,8,9,10-hexahydro-6,10-epiminocycloocta[d]pyrimidin-11-yl)methanone
(2-chloro-3-(trifluoromethyl)phenyl)(4-(5-hydroxypyrimidin-2-yl)-2-methyl-
5,6,7,8,9,10-hexahydro-6,10-epiminocycloocta[d]pyrimidin-11-yl)methanone
(2-chloro-3-(trifluoromethyl)phenyl)(4-(5-fluoropyrimidin-2-yl)-2-methyl-
5,6,7,8,9,10-hexahydro-6,10-epiminocycloocta[d]pyrimidin-11-yl)methanone
(2-chloro-3-(trifluoromethyl)phenyl)(2-methyl-4-(4-methylpyrimidin-2-yl)-
5,6,7,8,9,10-hexahydro-6,10-epiminocycloocta[d]pyrimidin-11-yl)methanone
(2-chloro-3-(trifluoromethyl)phenyl)(2-methyl-4-(5-methylpyridin-2-yl)-
5,6,7,8,9,10-hexahydro-6,10-epiminocycloocta[d]pyrimidin-11-yl)methanone
(2-chloro-3-(trifluoromethyl)phenyl)(2-methyl-4-phenyl-5,6,7,8,9,10-hexahydro-
6,10-epiminocycloocta[d]pyrimidin-11-yl)methanone
(2-chloro-3-methylphenyl)(2-methyl-4-(1H-pyrazol-5-yl)-5,6,7,8,9,10-hexahydro-
6,10-epiminocycloocta[d]pyrimidin-11-yl)methanone
(2-chloro-4-fluoro-3-(trifluoromethyl)phenyl)(2-methyl-4-(1H-pyrazol-5-yl)-
5,6,7,8,9,10-hexahydro-6,10-epiminocycloocta[d]pyrimidin-11-yl)methanone
(3-methyl-2-(trifluoromethyl)pyridin-4-yl)(2-methyl-4-(1H-pyrazol-5-yl)-
5,6,7,8,9,10-hexahydro-6,10-epiminocycloocta[d]pyrimidin-11-yl)methanone
(2,3-dimethylpyridin-4-yl)((6S,10R)-2-methyl-4-(1H-pyrazol-5-yl)-5,6,7,8,9,10-
hexahydro-6,10-epiminocycloocta[d]pyrimidin-11-yl)methanone
(2-methyl-3-(trifluoromethyl)pyridin-4-yl)((6S,10R)-2-methyl-4-(1H-pyrazol-5-yl)-
5,6,7,8,9,10-hexahydro-6,10-epiminocycloocta[d]pyrimidin-11-yl)methanone TABLE 1-continued (2,3-dimethylpyridin-4-yl)((6S,10R)-2-methyl-4-(1H-pyrazol-5-yl)-5,6,7,8,9,10-hexahydro-6,10-epiminocycloocta[d]pyrimidin-11-yl)methanone
(2-methyl-3-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone An additional embodiment of the invention is a compound selected from the list below:
- (2,3-dichlorophenyl)(2-methyl-4-(1H-pyrazol-5-yl)-5,6,7,8,9,10-hexahydro-6,10-epiminocycloocta[d]pyrimidin-11-yl)methanone;
- (2-chloro-3-(trifluoromethyl)phenyl)(2-methyl-4-(1H-pyrazol-5-yl)-5,6,7,8,9,10-hexahydro-6,10-epiminocycloocta[d]pyrimidin-11-yl)methanone;
- (2-chloro-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone;
- (2,3-dichloro-4-fluorophenyl)((6R,10S)-2-methyl-4-(1H-pyrazol-5-yl)-5,6,7,8,9,10-hexahydro-6,10-epiminocycloocta[d]pyrimidin-11-yl)methanone;
- (2,4-dichlorophenyl)((6R,10S)-2-methyl-4-(1H-pyrazol-5-yl)-5,6,7,8,9,10-hexahydro-6,10-epiminocycloocta[d]pyrimidin-11-yl)methanone;
- (2-methyl-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone;
- (3-chloro-2-(trifluoromethyl)pyridin-4-yl)((6R,10S)-2-methyl-4-(1H-pyrazol-5-yl)-5,6,7,8,9,10-hexahydro-6,10-epiminocycloocta[d]pyrimidin-11-yl)methanone;
- (2-fluoro-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone,
- (2-chloro-4-fluorophenyl)((6R,10S)-2-methyl-4-(1H-pyrazol-5-yl)-5,6,7,8,9,10-hexahydro-6,10-epiminocycloocta[d]pyrimidin-11-yl)methanone;
- (2,4-dichloro-3-fluorophenyl)((6R,10S)-2-methyl-4-(1H-pyrazol-5-yl)-5,6,7,8,9,10-hexahydro-6,10-epiminocycloocta[d]pyrimidin-11-yl)methanone;
- (2,3-dichlorophenyl)((6R,10S)-2-methyl-4-(1H-pyrazol-5-yl)-5,6,7,8,9,10-hexahydro-6,10-epiminocycloocta[d]pyrimidin-11-yl)methanone;
- (4-chloro-2-fluorophenyl)((6R,10S)-2-methyl-4-(1H-pyrazol-5-yl)-5,6,7,8,9,10-hexahydro-6,10-epiminocycloocta[d]pyrimidin-11-yl)methanone;
- (2-chloro-3-(trifluoromethyl)phenyl)((6R,10S)-4-(4-fluorophenyl)-2-methyl-5,6,7,8,9,10-hexahydro-6,10-epiminocycloocta[d]pyrimidin-11-yl)methanone;
- ((6R,10S)-4-(4-fluorophenyl)-2-methyl-5,6,7,8,9,10-hexahydro-6,10-epiminocycloocta[d]pyrimidin-11-yl)(2-methyl-3-(trifluoromethyl)phenyl)methanone;
- (2,4-dichlorophenyl)((6R,10S)-4-(4-fluorophenyl)-2-methyl-5,6,7,8,9,10-hexahydro-6,10-epiminocycloocta[d]pyrimidin-11-yl)methanone;
- (2-chloro-4-fluorophenyl)((6R,10S)-4-(4-fluorophenyl)-2-methyl-5,6,7,8,9,10-hexahydro-6,10-epiminocycloocta[d]pyrimidin-11-yl)methanone;
- (2,3-dichloro-4-fluorophenyl)((6R,10S)-4-(4-fluorophenyl)-2-methyl-5,6,7,8,9,10-hexahydro-6,10-epiminocycloocta[d]pyrimidin-11-yl)methanone;
- (3-chloro-2-(trifluoromethyl)pyridin-4-yl)((6R,10S)-4-(4-fluorophenyl)-2-methyl-5,6,7,8,9,10-hexahydro-6,10-epiminocycloocta[d]pyrimidin-11-yl)methanone;
- (2-chloro-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone;
- (2,4-dichlorophenyl)((6S,10R)-2-methyl-4-(1H-pyrazol-5-yl)-5,6,7,8,9,10-hexahydro-6,10-epiminocycloocta[d]pyrimidin-11-yl)methanone;
- (2-methyl-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone;
- (2-chloro-4-fluorophenyl)((6S,10R)-2-methyl-4-(1H-pyrazol-5-yl)-5,6,7,8,9,10-hexahydro-6,10-epiminocycloocta[d]pyrimidin-11-yl)methanone;
- (2,4-dichloro-3-fluorophenyl)((6S,10R)-2-methyl-4-(1H-pyrazol-5-yl)-5,6,7,8,9,10-hexahydro-6,10-epiminocycloocta[d]pyrimidin-11-yl)methanone;
- (3-chloro-2-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone;
- (2,3-dichloro-4-fluorophenyl)((6S,10R)-2-methyl-4-(1H-pyrazol-5-yl)-5,6,7,8,9,10-hexahydro-6,10-epiminocycloocta[d]pyrimidin-11-yl)methanone,
- (2-fluoro-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone;
- (3-fluoro-2-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone;
- (4-chloro-2-fluorophenyl)((6S,10R)-2-methyl-4-(1H-pyrazol-5-yl)-5,6,7,8,9,10-hexahydro-6,10-epiminocycloocta[d]pyrimidin-11-yl)methanone;
- (2,3-dichlorophenyl)((6S,10R)-2-methyl-4-(1H-pyrazol-5-yl)-5,6,7,8,9,10-hexahydro-6,10-epiminocycloocta[d]pyrimidin-11-yl)methanone;
- (2-chloro-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone;
- (2,3-dichlorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone;
- (3-chloro-2-(trifluoromethyl)pyridin-4-yl)((6S,10R)-2-methyl-4-(1-methyl-1H-pyrazol-4-yl)-5,6,7,8,9,10-hexahydro-6,10-epiminocycloocta[d]pyrimidin-11-yl)methanone;
- (2,3-dichloro-4-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone;
- (2-fluoro-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone;
- (2,4-dichloro-3-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone;
- (2-chloro-4-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone;
- (3-fluoro-2-(trifluoromethyl)pyridin-4-yl)((6S,10R)-2-methyl-4-(1-methyl-1H-pyrazol-4-yl)-5,6,7,8,9,10-hexahydro-6,10-epiminocycloocta[d]pyrimidin-11-yl)methanone;
- (4-chloro-2-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone;

(2-methyl-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone;

(2,4-dichlorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone;

(2-chloro-3-(trifluoromethyl)phenyl)((6S,10R)-2-methyl-4-(pyrimidin-2-yl)-5,6,7,8,9,10-hexahydro-6,10-epiminocycloocta[d]pyrimidin-11-yl)methanone;

(3-chloro-2-(trifluoromethyl)pyridin-4-yl)((6S,10R)-2-methyl-4-(pyrimidin-2-yl)-5,6,7,8,9,10-hexahydro-6,10-epiminocycloocta[d]pyrimidin-11-yl)methanone, (2-methyl-3-(trifluoromethyl)phenyl)((6S,10R)-2-methyl-4-(pyrimidin-2-yl)-5,6,7,8,9,10-hexahydro-6,10-epiminocycloocta[d]pyrimidin-11-yl)methanone;

(2,4-dichloro-3-fluorophenyl)((6S,10R)-2-methyl-4-(pyrimidin-2-yl)-5,6,7,8,9,10-hexahydro-6,10-epiminocycloocta[d]pyrimidin-11-yl)methanone;

(2,3-dichlorophenyl)((6S,10R)-2-methyl-4-(pyrimidin-2-yl)-5,6,7,8,9,10-hexahydro-6,10-epiminocycloocta[d]pyrimidin-11-yl)methanone;

(2-chloro-3-(trifluoromethyl)phenyl)((6S,10R)-2-methyl-4-(pyrazin-2-yl)-5,6,7,8,9,10-hexahydro-6,10-epiminocycloocta[d]pyrimidin-11-yl)methanone;

(2,4-dichloro-3-fluorophenyl)((6S,10R)-2-methyl-4-(pyrazin-2-yl)-5,6,7,8,9,10-hexahydro-6,10-epiminocycloocta[d]pyrimidin-11-yl)methanone;

(2,3-dichlorophenyl)((6S,10R)-2-methyl-4-(pyrazin-2-yl)-5,6,7,8,9,10-hexahydro-6,10-epiminocycloocta[d]pyrimidin-11-yl)methanone;

(3-chloro-2-(trifluoromethyl)pyridin-4-yl)((6S,10R)-2-methyl-4-(pyrazin-2-yl)-5,6,7,8,9,10-hexahydro-6,10-epiminocycloocta[d]pyrimidin-11-yl)methanone;

(2-methyl-3-(trifluoromethyl)phenyl)((6S,10R)-2-methyl-4-(pyrazin-2-yl)-5,6,7,8,9,10-hexahydro-6,10-epiminocycloocta[d]pyrimidin-11-yl)methanone;

(2-chloro-3-(trifluoromethyl)phenyl)((6S,10R)-4-(4-fluorophenyl)-2-methyl-5,6,7,8,9,10-hexahydro-6,10-epiminocycloocta[d]pyrimidin-11-yl)methanone;

(3-chloro-2-(trifluoromethyl)pyridin-4-yl)((6S,10R)-4-(4-fluorophenyl)-2-methyl-5,6,7,8,9,10-hexahydro-6,10-epiminocycloocta[d]pyrimidin-11-yl)methanone;

((6S,10R)-4-(4-fluorophenyl)-2-methyl-5,6,7,8,9,10-hexahydro-6,10-epiminocycloocta[d]pyrimidin-11-yl)(2-methyl-3-(trifluoromethyl)phenyl)methanone;

(2,4-dichloro-3-fluorophenyl)((6S,10R)-4-(4-fluorophenyl)-2-methyl-5,6,7,8,9,10-hexahydro-6,10-epiminocycloocta[d]pyrimidin-11-yl)methanone;

(2,3-dichlorophenyl)((6S,10R)-4-(4-fluorophenyl)-2-methyl-5,6,7,8,9,10-hexahydro-6,10-epiminocycloocta[d]pyrimidin-11-yl)methanone;

(2-chloro-3-(trifluoromethyl)phenyl)((6S,10R)-2-methyl-4-(1-methyl-1H-pyrazol-5-yl)-5,6,7,8,9,10-hexahydro-6,10-epiminocycloocta[d]pyrimidin-11-yl)methanone;

(2-methyl-3-(trifluoromethyl)phenyl)((6S,10R)-2-methyl-4-(1-methyl-1H-pyrazol-5-yl)-5,6,7,8,9,10-hexahydro-6,10-epiminocycloocta[d]pyrimidin-11-yl)methanone;

(2,4-dichloro-3-fluorophenyl)((6S,10R)-2-methyl-4-(1-methyl-1H-pyrazol-5-yl)-5,6,7,8,9,10-hexahydro-6,10-epiminocycloocta[d]pyrimidin-11-yl)methanone;

(2,3-dichlorophenyl)((6S,10R)-2-methyl-4-(1-methyl-1H-pyrazol-5-yl)-5,6,7,8,9,10-hexahydro-6,10-epiminocycloocta[d]pyrimidin-11-yl)methanone, (3-chloro-2-(trifluoromethyl)pyridin-4-yl)((6S,10R)-2-methyl-4-(1-methyl-1H-pyrazol-5-yl)-5,6,7,8,9,10-hexahydro-6,10-epiminocycloocta[d]pyrimidin-11-yl)methanone;

(3-chloro-2-(trifluoromethyl)pyridin-4-yl)((6S,10R)-2-methyl-4-(pyridin-2-yl)-5,6,7,8,9,10-hexahydro-6,10-epiminocycloocta[d]pyrimidin-11-yl)methanone;

(2-methyl-3-(trifluoromethyl)phenyl)((6S,10R)-2-methyl-4-(pyridin-2-yl)-5,6,7,8,9,10-hexahydro-6,10-epiminocycloocta[d]pyrimidin-11-yl)methanone;

(2-chloro-3-(trifluoromethyl)phenyl)((6S,10R)-2-methyl-4-(pyridin-2-yl)-5,6,7,8,9,10-hexahydro-6,10-epiminocycloocta[d]pyrimidin-11-yl)methanone;

(2,4-dichloro-3-fluorophenyl)((6S,10R)-2-methyl-4-(pyridin-2-yl)-5,6,7,8,9,10-hexahydro-6,10-epiminocycloocta[d]pyrimidin-11-yl)methanone, and (2,3-dichlorophenyl)((6S,10R)-2-methyl-4-(pyridin-2-yl)-5,6,7,8,9,10-hexahydro-6,10-epiminocycloocta[d]pyrimidin-11-yl)methanone.

An additional embodiment of the invention is a compound selected from the list below:

(2-amino-4-(1H-pyrazol-3-yl)-5,6,7,8,9,10-hexahydro-6,10-epiminocycloocta[d]pyrimidin-11-yl)(2-chloro-3-(trifluoromethyl)phenyl)methanone;

(4-(1H-pyrazol-3-yl)-5,6,7,8,9,10-hexahydro-6,10-epiminocycloocta[d]pyrimidin-11-yl)(2-chloro-3-(trifluoromethyl)phenyl)methanone;

(2-chloro-3-(trifluoromethyl)phenyl)(2-isopropyl-4-(1H-pyrazol-3-yl)-5,6,7,8,9,10-hexahydro-6,10-epiminocycloocta[d]pyrimidin-11-yl)methanone;

(2-chloro-3-(trifluoromethyl)phenyl)(2-ethyl-4-(1H-pyrazol-3-yl)-5,6,7,8,9,10-hexahydro-6,10-epiminocycloocta[d]pyrimidin-11-yl)methanone;

(2-chloro-3-(trifluoromethyl)phenyl)(2-methyl-4-(2H-1,2,3-triazol-2-yl)-5,6,7,8,9,10-hexahydro-6,10-epiminocycloocta[d]pyrimidin-11-yl)methanone;

(2-chloro-3-(trifluoromethyl)phenyl)(4-(4-fluoro-1H-pyrazol-3-yl)-2-methyl-5,6,7,8,9,10-hexahydro-6,10-epiminocycloocta[d]pyrimidin-11-yl)methanone;

(2-chloro-3-(trifluoromethyl)phenyl)(2-methyl-4-(4-(trifluoromethyl)-1H-pyrazol-3-yl)-5,6,7,8,9,10-hexahydro-6,10-epiminocycloocta[d]pyrimidin-11-yl)methanone;

(2-chloro-3-(trifluoromethyl)phenyl)(4-(3,5-dimethylisoxazol-4-yl)-2-methyl-5,6,7,8,9,10-hexahydro-6,10-epiminocycloocta[d]pyrimidin-11-yl)methanone;

(4-(1H-imidazol-2-yl)-2-methyl-5,6,7,8,9,10-hexahydro-6,10-epiminocycloocta[d]pyrimidin-11-yl)(2-chloro-3-(trifluoromethyl)phenyl)methanone, (2-chloro-3-(trifluoromethyl)phenyl)(2-methyl-4-(thiazol-2-yl)-5,6,7,8,9,10-hexahydro-6,10-epiminocycloocta[d]pyrimidin-11-yl)methanone;

(2-chloro-3-(trifluoromethyl)phenyl)(2-methyl-4-(1H-pyrrol-2-yl)-5,6,7,8,9,10-hexahydro-6,10-epiminocycloocta[d]pyrimidin-11-yl)methanone;

(2-chloro-3-(trifluoromethyl)phenyl)(2-methyl-4-(thiazol-4-yl)-5,6,7,8,9,10-hexahydro-6,10-epiminocycloocta[d]pyrimidin-11-yl)methanone;

(2-chloro-3-(trifluoromethyl)phenyl)(4-(isoxazol-4-yl)-2-methyl-5,6,7,8,9,10-hexahydro-6,10-epiminocycloocta[d]pyrimidin-11-yl)methanone;

(2-chloro-3-(trifluoromethyl)phenyl)(2-methyl-4-(thiophen-3-yl)-5,6,7,8,9,10-hexahydro-6,10-epiminocycloocta[d]pyrimidin-11-yl)methanone;

(2-chloro-3-(trifluoromethyl)phenyl)(2-methyl-4-(4H-1,2,4-triazol-4-yl)-5,6,7,8,9,10-hexahydro-6,10-epiminocycloocta[d]pyrimidin-11-yl)methanone;

(2-chloro-3-(trifluoromethyl)phenyl)(4-(5-hydroxypyrimidin-2-yl)-2-methyl-5,6,7,8,9,10-hexahydro-6,10-epiminocycloocta[d]pyrimidin-11-yl)methanone;

(2-chloro-3-(trifluoromethyl)phenyl)(4-(5-fluoropyrimidin-2-yl)-2-methyl-5,6,7,8,9,10-hexahydro-6,10-epiminocycloocta[d]pyrimidin-11-yl)methanone;
(2-chloro-3-(trifluoromethyl)phenyl)(2-methyl-4-(4-methylpyrimidin-2-yl)-5,6,7,8,9,10-hexahydro-6,10-epiminocycloocta[d]pyrimidin-11-yl)methanone;
(2-chloro-3-(trifluoromethyl)phenyl)(2-methyl-4-(5-methylpyridin-2-yl)-5,6,7,8,9,10-hexahydro-6,10-epiminocycloocta[d]pyrimidin-11-yl)methanone;
(2-chloro-3-(trifluoromethyl)phenyl)(2-methyl-4-phenyl-5,6,7,8,9,10-hexahydro-6,10-epiminocycloocta[d]pyrimidin-11-yl)methanone;
(2-chloro-3-methylphenyl)(2-methyl-4-(1H-pyrazol-5-yl)-5,6,7,8,9,10-hexahydro-6,10-epiminocycloocta[d]pyrimidin-11-yl)methanone;
(2-chloro-4-fluoro-3-(trifluoromethyl)phenyl)(2-methyl-4-(1H-pyrazol-5-yl)-5,6,7,8,9,10-hexahydro-6,10-epiminocycloocta[d]pyrimidin-11-yl)methanone;
(3-methyl-2-(trifluoromethyl)pyridin-4-yl)(2-methyl-4-(1H-pyrazol-5-yl)-5,6,7,8,9,10-hexahydro-6,10-epiminocycloocta[d]pyrimidin-11-yl)methanone;
(2,3-dimethylpyridin-4-yl)((6S,10R)-2-methyl-4-(1H-pyrazol-5-yl)-5,6,7,8,9,10-hexahydro-6,10-epiminocycloocta[d]pyrimidin-11-yl)methanone;
(2-methyl-3-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone;
(2,3-dimethylpyridin-4-yl)((6S,10R)-2-methyl-4-(1H-pyrazol-5-yl)-5,6,7,8,9,10-hexahydro-6,10-epiminocycloocta[d]pyrimidin-11-yl)methanone, and
(2-methyl-3-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone.

Also within the scope of the invention are enantiomers and diastereomers of the compounds of Formula I. Also within the scope of the invention are the pharmaceutically acceptable salts of the compounds of Formula I, as well as the pharmaceutically acceptable salts of the enantiomers and diastereomers of the compounds of Formula I. Also within the scope of the invention are isotopic variations of compounds of Formula I, such as, e.g., deuterated compounds of Formula I.

An additional embodiment of the invention is a pharmaceutical composition comprising an effective amount of at least one compound in Table 1 and at least one pharmaceutically acceptable excipient.

An additional embodiment of the invention is a method of treating a subject suffering from or diagnosed with a disease, disorder, or medical condition mediated by P2X7 receptor activity, comprising administering to a subject in need of such treatment an effective amount of at least one compound selected from compounds of Formula (I):

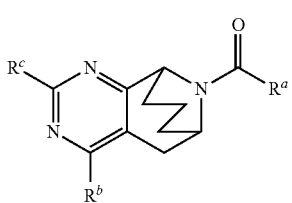

and enantiomers or diastereomers thereof;
and pharmaceutically acceptable salts thereof;

wherein:
$R^a$ is

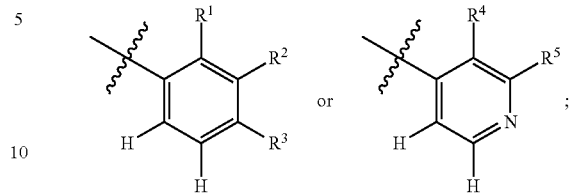

$R^1$, $R^2$, $R^3$, and $R^4$ are each independently selected from the group consisting of: H, halo, $C_1$-$C_3$alkyl and $C_1$-$C_3$perhaloalkyl;
$R^5$ is $C_1$-$C_3$perhaloalkyl or $C_1$-$C_3$alkyl;
$R^b$ is selected from the group consisting of:

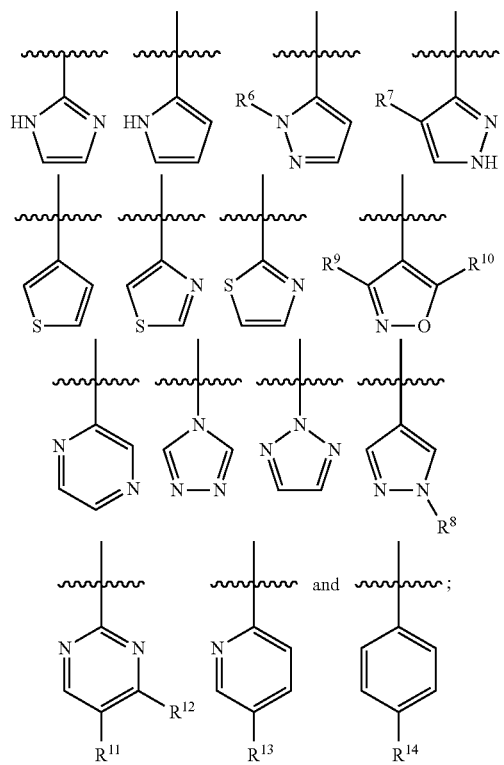

Wherein:
$R^6$, $R^8$, $R^9$, $R^{10}$, $R^{12}$, $R^{13}$ are independently H or $C_1$-$C_3$alkyl,
$R^7$ is H, halo or $C_1$-$C_3$perhaloalkyl,
$R^{11}$ is H, halo or OH;
$R^{14}$ is H or halo; and
$R^c$ is selected from the group consisting of: H, $NH_2$, $C_1$-$C_4$alkyl.

In preferred embodiments of the inventive method, the disease, disorder, or medical condition is selected from: diseases of the autoimmune and inflammatory system (Arulkumaran, N. et al. *Expert Opin. Invetig Drugs*, 2011, July; 20(7):897-915) [examples of diseases of the autoimmune and inflammatory system include rheumatoid arthritis, osteoarthritis, interstitial cystitis (Martins J P, et. al., *Br J Pharmacol.* 2012 January; 165(1):183-96), psoriasis (Killeen, M. E., et al., J Immunol. 2013 Apr. 15; 190(8): 4324-36), septic shock, sepsis, allergic dermatitis, asthma (examples of asthma include allergic asthma, mild to severe asthma, and steroid resistant asthma), idiopathic pulmonary fibrosis, allergic rhinitis, chronic obstructive pulmonary disease and airway hyper-responsiveness]; diseases of the nervous and neuro-immune system [examples of diseases of the nervous and neuro-immune system include acute and chronic pain (examples of acute and chronic pain include neuropathic pain, inflammatory pain, migraine, spontaneous pain (examples of spontaneous pain include opioid induced pain, diabetic neuropathy, postherpetic neuralgia, low back pain, chemotherapy-induced neuropathic pain, fibromyalgia) (Romagnoli, R, et. al., *Expert Opin. Ther. Targets*, 2008, 12(5), 647-661)], and diseases involved with, and without, neuroinflammation of the Central Nervous System (CNS) [examples of diseases involved with, and without, neuroinflammation of the Central Nervous System (CNS) include mood disorders (examples of mood disorders include major depression, major depressive disorder, treatment resistant depression, bipolar disorder, anxious depression, anxiety) (Friedle, S A, et. al., *Recent Patents on CNS Drug Discovery*, 2010, 5, 35-45, Romagnoli, R, et. al., 2008), cognition, sleep disorders, multiple sclerosis (Sharp A J, et. al., J Neuroinflammation. 2008 Aug. 8; 5:33, Oyanguren-Desez O, et. al., *Cell Calcium.* 2011 November; 50(5):468-72, Grygorowicz T, et. al., *Neurochem Int.* 2010 December; 57(7):823-9), epileptic seizures (Engel T, et. al., *FASEB J.* 2012 April; 26(4):1616-28, Kim J E, et. al. *Neurol Res.* 2009 November; 31(9):982-8, Avignone E, et. al., *J Neurosci.* 2008 Sep. 10; 28(37):9133-44), Parkinson's disease (Marcellino D, et. al., *J Neural Transm.* 2010 June; 117(6):681-7), schizophrenia, Alzheimer's disease (Diaz-Hernandez J I, et. al., *Neurobiol Aging.* 2012 August; 33(8):1816-28, Delarasse C, *J Biol Chem.* 2011 Jan. 28; 286(4):2596-606, Sanz J M, et. al., *J Immunol.* 2009 Apr. 1; 182(7):4378-85), Huntington's disease (Díaz-Hernández M, et. Al., *FASEB J.* 2009 June; 23(6):1893-906), Amyotrophic Lateral Sclerosis, autism, spinal cord injury, cerebral ischemia/traumatic brain injury (Chu K, et. al., *J Neuroinflammation.* 2012 Apr. 18; 9:69, Arbeloa J, et. al, *Neurobiol Dis.* 2012 March; 45(3):954-61) and stress-related disorders].

In addition, P2X7 intervention may be beneficial in diseases of the cardiovascular, metabolic, gastrointestinal and urogenital systems [examples of diseases of the cardiovascular, metabolic, gastrointestinal and urogenital systems include diabetes (*Arterioscler Thromb Vasc Biol.* 2004 July; 24(7):1240-5, *J Cell Physiol.* 2013 January; 228(1):120-9), diabetes mellitus, thrombosis (Furlan-Freguia C, et. al., *J Clin Invest.* 2011 July; 121(7):2932-44, Vergani, A. et al., *Diabetes*, 2013, 62, 1665-1675), irritable bowel disease, irritable bowel syndrome, (*J Immunol.* 2011 Aug. 1; 187(3): 1467-74. Epub 2011 Jun. 22), Crohn's disease, cardiovascular diseases (examples of cardiovascular disease include hypertension (Ji X, et. al., *Am J Physiol Renal Physiol.* 2012 October; 303(8):F1207-15), myocardial infarction, ischemic heart disease, ischemia) ureteric obstruction, lower urinary tract syndrome (*Br J Pharmacol.* 2012 January; 165(1):183-96), lower urinary tract dysfunction such as incontinence, and disease after cardiac transplant (Vergani, A. et al., *Circulation.* 2013; 127:463-475)].

P2X7 antagonism may also present a novel therapeutic strategy for skeletal disorders, (examples of skeletal disorders include osteoporosis/osteopetrosis) and may also modulate secretory function of exocrine glands.

It is also hypothesized that modulation of the P2X7 receptor may also be beneficial in conditions such as: glaucoma, Glomerulonephritis, Chaga's Disease, *chlamydia*, neuroblastoma, Tuberculosis, Polycystic Kidney Disease, cancer, and acne (Thiboutot, D. M. *J Investigative Dermatology*, 2014, 134, 595-597).

An additional embodiment of the invention is a method of treating a subject suffering from or diagnosed with a disease, disorder, or medical condition mediated by P2X7 receptor activity, wherein the disease, disorder, or medical condition is selected from the group consisting of: diseases of the autoimmune and inflammatory system [examples of diseases of the autoimmune and inflammatory system include rheumatoid arthritis, osteoarthritis, interstitial cystitis, psoriasis, septic shock, sepsis, allergic dermatitis, asthma (examples of asthma include allergic asthma, mild to severe asthma, and steroid resistant asthma), idiopathic pulmonary fibrosis, allergic rhinitis, chronic obstructive pulmonary disease and airway hyper-responsivenes]; diseases of the nervous and neuro-immune system [examples of diseases of the nervous and neuro-immune system include acute and chronic pain (examples of acute and chronic pain include neuropathic pain, inflammatory pain, migraine, spontaneous pain (examples of spontaneous pain include opioid induced pain, diabetic neuropathy, postherpetic neuralgia, low back pain, chemotherapy-induced neuropathic pain, fibromyalgia)]; diseases involved with, and without, neuroinflammation of the Central Nervous System (CNS) [examples of diseases involved with, and without, neuroinflammation of the Central Nervous System (CNS) include mood disorders (examples of mood disorders include major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, Amyotrophic Lateral Sclerosis, autism, spinal cord injury and cerebral ischemia/traumatic brain injury, and stress-related disorders]; diseases of the cardiovascular, metabolic, gastrointestinal and urogenital systems [examples of diseases of the cardiovascular, metabolic, gastrointestinal and urogenital systems include diabetes, diabetes mellitus, thrombosis, irritable bowel disease, irritable bowel syndrome, Crohn's disease, cardiovascular diseases (examples of cardiovascular disease include hypertension, myocardial infarction, ischemic heart disease, ischemia) ureteric obstruction, lower urinary tract syndrome, lower urinary tract dysfunction such as incontinence, and disease after cardiac transplantation]; skeletal disorders, (examples of skeletal disorders include osteoporosis/osteopetrosis) and diseases involving the secretory function of exocrine glands and diseases such as glaucoma, Glomerulonephritis, Chaga's Disease, *chlamydia*, neuroblastoma, Tuberculosis, Polycystic Kidney Disease, cancer, and acne.

An additional embodiment of the invention is a method of treating a subject suffering from or diagnosed with a disease, disorder, or medical condition mediated by P2X7 receptor activity wherein the disease, disorder or medical condition is a disease involved with, and without, neuroinflammation of the Central Nervous System (CNS).

An additional embodiment of the invention is a method of treating a subject suffering from or diagnosed with a disease involved with, and without, neuroinflammation of the Central Nervous System (CNS) wherein the disease, disorder or medical condition is a mood disorder.

An additional embodiment of the invention is a method of treating a subject suffering from a mood disorder wherein the mood disorder is treatment resistant depression.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_1$-$C_3$ alkyl as used here refers to a straight- or branched-chain alkyl group having from 1 to 3 carbon atoms in the chain. The term $C_1$-$C_4$ alkyl as used here refers to a straight- or branched-chain alkyl group having from 1 to 4 carbon atoms in the chain.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "alkalkoxy" refers to the group alkyl-O-alkyl, where alkyl is defined above. Such groups include methylenemethoxy (—CH$_2$OCH$_3$) and ethylenemethoxy (—CH$_2$CH$_2$OCH$_3$).

The terms "hydroxyl" and "hydroxy" refer to an —OH group.

The term "cycloalkyl" refers to a saturated carbocycle having from 3 to 6 ring atoms per carbocycle. Illustrative examples of cycloalkyl groups include the following entities, in the form of properly bonded moieties:

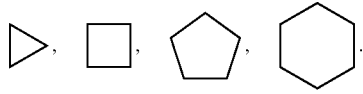

The term "$C_3$-$C_4$ cycloalkyl" as used here refers to a saturated carbocycle having from 3 to 4 ring atoms.

A "heterocycloalkyl" refers to a monocyclic ring structure that is saturated and has from 4 to 6 ring atoms per ring structure selected from carbon atoms and one nitrogen atom. Illustrative entities, in the form of properly bonded moieties, include:

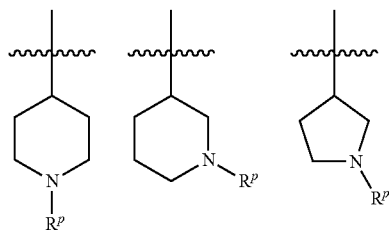

The term "aryl" refers to a monocyclic, aromatic carbocycle (ring structure having ring atoms that are all carbon) having 6 atoms per ring. (Carbon atoms in the aryl groups are sp$^2$ hybridized.)

The term "phenyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

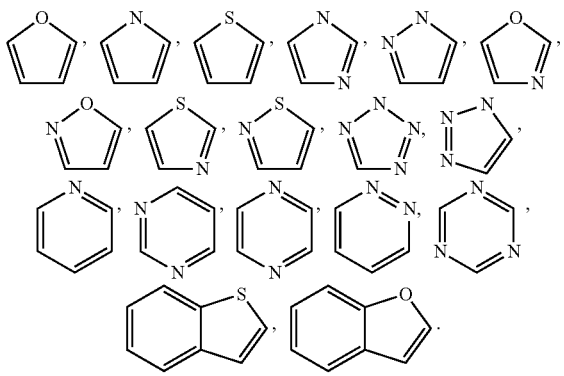

Those skilled in the art will recognize that the species of heteroaryl, cycloalkyl, aryl and heterocycloalkyl groups listed or illustrated above are not exhaustive, and that additional species within the scope of these defined terms may also be selected.

The term "cyano" refers to the group —CN.

The term "halo" represents chloro, fluoro, bromo or iodo.

The term "perhaloalkyl" refers to a straight- or branched-chain alkyl group having from 1 to 4 carbon atoms in the chain optionally substituting hydrogens with halogens. Examples of perhaloalkyl groups include trifluoromethyl (CF$_3$), difluoromethyl (CF$_2$H), monofluoromethyl (CH$_2$F), pentafluoroethyl (CF$_2$CF$_3$), tetrafluoroethyl (CHFCF$_3$), monofluoroethyl (CH$_2$CH$_2$F), trifluoroethyl (CH$_2$CF$_3$), tetrafluorotrifluoromethylethyl (—CF(CF$_3$)$_2$), and groups that in light of the ordinary skill in the art and the teachings provided herein would be considered equivalent to any one of the foregoing examples.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

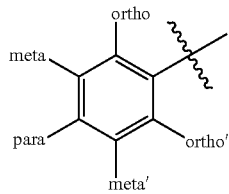

When referring to substituents on a pyridyl group, the terms "para", "meta", and "ortho" refer to the placement of a substituent relative to the point of attachment of the pyridyl ring. For example the structure below is described as 4-pyridyl with the X substituent in the ortho position and the Y substituent in the meta position:

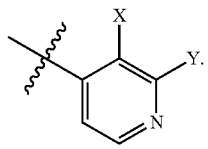

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding MgSO$_4$ and NaHCO$_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting in a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound of pharmaceutically acceptable salts thereof in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols ▬ and ▬ are used as meaning the same spatial arrangement in chemical structures shown herein. Analogously, the symbols ⦀⦀⦀⦀ and ⦀⦀⦀⦀ are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) or pharmaceutically acceptable salts of compounds of Formula (I) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) or pharmaceutically acceptable salts of compounds of Formula (I) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The invention includes also pharmaceutically acceptable salts of the compounds of Formula (I), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmcopoeia or other generally recognized pharmacopoeia for use in animals, and more particularly, in humans.

A "pharmaceutically acceptable salt" is intended to mean a salt of a free acid or base of compounds represented by Formula (I) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I, IIa or IIb)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I, IIa or IIb). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I, IIa or IIb) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of the P2X7 receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the P2X7 receptor expression or activity, and "activators" are compounds that increase, activate, facilitate, sensitize, or up-regulate P2X7 receptor expression or activity.

The term "treat", "treatment" or "treating", as used herein, is intended to refer to administration of an active agent or composition of the invention to a subject for the purpose of affecting a therapeutic or prophylactic benefit through modulation of P2X7 receptor activity. Treating includes reversing, ameliorating, alleviating, inhibiting the progress of, lessening the severity of, or preventing a disease, disorder, or condition, or one or more symptoms of such disease, disorder or condition mediated through modulation of P2X7 receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by P2X7 receptor activity, such as: diseases of the autoimmune and inflammatory system [examples of diseases of the autoimmune and inflammatory system include rheumatoid arthritis, osteoarthritis, interstitial cystitis, psoriasis, septic shock, sepsis, allergic dermatitis, asthma (examples of asthma include allergic asthma, mild to severe asthma, and steroid resistant asthma), idiopathic pulmonary fibrosis, allergic rhinitis, chronic obstructive pulmonary disease and airway hyper-responsivenes]; diseases of the nervous and neuro-immune system [examples of diseases of the nervous and neuro-immune system include acute and chronic pain (examples of acute and chronic pain include neuropathic pain, inflammatory pain, migraine, spontaneous pain (examples of spontaneous pain include opioid induced pain, diabetic neuropathy, postherpetic neuralgia, low back pain, chemotherapy-induced neuropathic pain, fibromyalgia)]; diseases involved with, and without, neuroinflammation of the Central Nervous System (CNS) [examples of diseases involved with, and without, neuroinflammation of the Central Nervous System (CNS) include mood disorders (examples of mood disorders include major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, Amyotrophic Lateral Sclerosis, autism, spinal cord injury and cerebral ischemia/traumatic brain injury, and stress-related disorders]; diseases of the cardiovascular, metabolic, gastrointestinal and urogenital systems [examples of diseases of the cardiovascular, metabolic, gastrointestinal and urogenital systems include diabetes, diabetes mellitus, thrombosis, irritable bowel disease, irritable bowel syndrome, Crohn's disease, cardiovascular diseases (examples of cardiovascular disease include hypertension, myocardial infarction, ischemic heart disease, ischemia) ureteric obstruction, lower urinary tract syndrome, lower urinary tract dysfunction such as incontinence, and disease after cardiac transplantation]; skeletal disorders, (examples of skeletal disorders include osteoporosis/osteopetrosis) and diseases involving the secretory function of exocrine glands and diseases such as glaucoma, Glomerulonephritis, Chaga's Disease, *chlamydia*, neuroblastoma, Tuberculosis, Polycystic Kidney Disease, cancer, and acne.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of compounds of Table 1 or included with such an agent in a pharmaceutical composition according to the invention. In an exemplary embodiment, additional active ingredients are those that are known or discovered to be effective in the treatment of conditions, disorders, or diseases mediated by P2X7 activity, such as another P2X7 modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Schemes

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

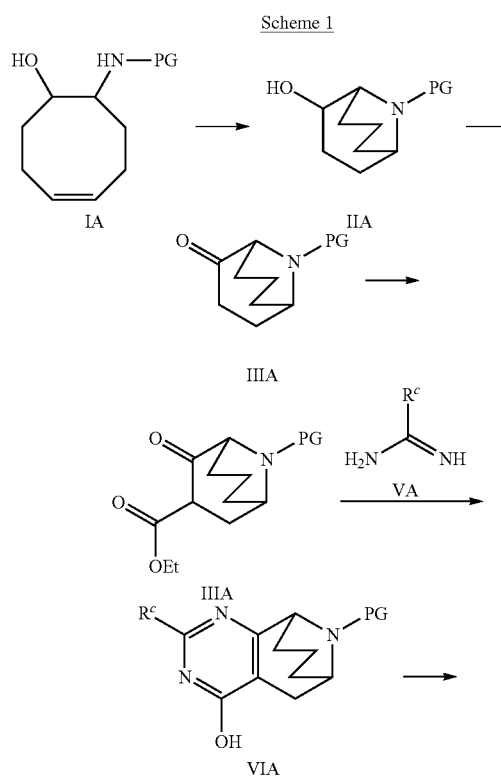

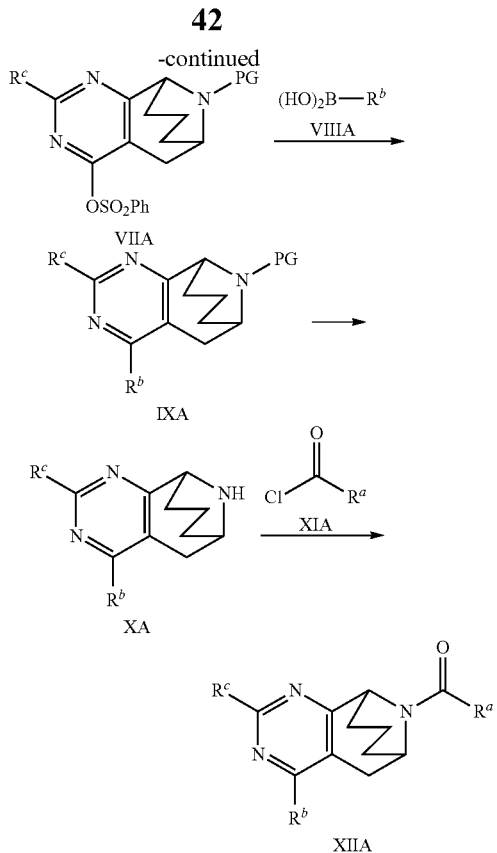

The group PG represents a protecting group. One skilled in the art will select the appropriate protecting group compatible with the desired reactions. The protecting groups may be removed at a convenient subsequent stage using methods known from the art. Alternatively, it may be necessary to employ, in place of the ultimately desired substituent, a suitable group that may be carried through the reaction scheme and replaced as appropriate with the desired substituent. Such compounds, precursors, or prodrugs are also within the scope of the invention. Examples of preferred protecting groups (PG) include; carbamates, benzyl and substituted benzyl groups. Especially preferred protecting groups are; tert-butyloxycarbonyl, benzyl and (R)-methylbenzyl. The general synthesis of embodiments of the invention are shown in Scheme 1 and the examples which follow.

Compound IA is converted to heterocycle IIA though treatment with mercury(II) chloride in a solvent such as a mixture of THF and water at room temperature overnight followed by treatment at 0° C. with 3 M sodium hydroxide and sodium borohydride. If a chiral PG, such as (R)-methylbenzyl, is employed diastereomers may be separated.

Compound IIA is converted to compound IIIA under oxidative conditions such as treatment with DMSO, oxalyl chloride and triethylamine in a solvent such as DCM. The reaction is run initially at −78° C. and then warmed to room temperature and stirred overnight.

Compound IIIA is converted to compound IVA by treatment with a strong base such as LHMDS in a solvent such as THF at −78° C. for 30 minutes followed by treatment with ethyl cyanoformate at −78° C. for 2 hours.

Compound IVA is converted to VIA through treatment with VA and 0.5 N sodium ethoxide in a solvent such as ethanol. The reaction mixture is heated to reflux for 12 hours.

Compound VIA is converted to VIIA through treatment with p-toluenesulfonyl chloride in the presence of triethylamine and a catalytic amount of DMAP in a solvent such as DCM. The reaction mixture was generated at 0° C. and allowed to warm to room temperature and stir overnight.

Compound VIIA is converted to compound IXA through a metal mediated cross coupling such as a Suzuki reaction, with a coupling piece such as compound VIIIA, or other suitable boronic acid equivalent, in the presence of a catalyst such as tetrakis(triphenylphosphine)palladium and a base such as sodium carbonate, potassium carbonate, potassium phosphate, potassium t-butoxide or cesium carbonate in a solvent such as a mixture of dioxane and water, a mixture of n-butanol and water, DMF or ethanol. The reaction mixture may be heated to a temperature between room temperature and 100° C. Alternatively the conversion of compound VIIA to compound IXA can be accomplished through a Stille Coupling.

Compound IXA is converted to compound XA though implementation of conditions appropriate to remove the chosen PG. One skilled in the art will easily be able to identify conditions necessary for PG removal. Depending on the chosen conditions XA may or may not be a halide salt.

Compound XA is converted to compound XIIA through treatment with of compound XA with compound XIA in a solvent such as DCM, THF, benzene or DCE in the presence of a base such as triethylamine, diisoprolyethylamine or pyridine. The reaction may initially be run at a temperature between −78° C. and 0° C. The reaction may then be allowed to warm to room temperature over a time period between 4-18 hours. Reagent XIA can be generated from the corresponding acid by procedures commonly found in the literature and familiar to one skilled in the art.

Dependent on the identity of $R^a$, $R^b$ and $R^c$ additional protecting group manipulation may be required and one skilled in the art would easily identify and choose appropriate conditions to accomplish said manipulations.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature under a nitrogen atmosphere. Where solutions were "dried", they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM Corporation Discover instrument. Hydrogenations on the H-cube hydrogenation apparatus were run by passing solvent containing reactant through a catalyst cartridge on an H-Cube hydrogenation apparatus at a pressure of 15 to 100 bar and a flow rate of 1 to 30 ml/min.

Normal-phase silica gel column chromatography (sgc) was performed on silica gel ($SiO_2$) using prepackaged cartridges, eluting with 2 M $NH_3$/MeOH in $CH_2Cl_2$ unless otherwise indicated.

Preparative reverse-phase high performance liquid chromatography (HPLC) was performed on a Agilent HPLC with an Xterra Prep $RP_{18}$ (5 μm, 30×100 mm, or 50×150 mm) column, and a gradient of 10 to 99% acetonitrile/water (20 mM $NH_4OH$) over 12 to 18 min, and a flow rate of 30 or 80 mL/min, unless otherwise indicated.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

A notation of (±) or R/S indicates that the product is a racemic mixture of enantiomers and/or diastereomers. A notation of, for example, (2S,3R) indicates that product stereochemistry depicted is based on the known stereochemistry of similar compounds and/or reactions. A notation of, for example, (2S*, 3R*) indicates that the product is a pure and single diastereomer but the absolute stereochemistry is not established and relative stereochemistry is shown.

Chemical names were generated using ChemDraw Ultra 6.0.2 (CambridgeSoft Corp., Cambridge, Mass.).

Abbreviations and acronyms used herein include the following:

| Term | Acronym/Abbreviation |
|---|---|
| High-pressure liquid chromatography | HPLC |
| Tetrahydrofuran | THF |
| tert-Butylcarbamoyl | Boc, BOC |
| Dichloromethane | DCM |
| Trifluoroacetic acid | TFA |
| N,N-Dimethylformamide | DMF |
| Methanol | MeOH |
| Ethanol | EtOH |
| Acetonitrile | ACN, MeCN |
| Ethyl Acetate | EtOAc, or EA |
| Triethylamine | TEA |
| Benzotriazol-1-yloxytris(dimethylamino)-phosphonium hexafluorophosphate | BOP |
| Dimethyl sulfoxide | DMSO |
| Flash colum chromatography | FCC |
| Lithium bis(trimethylsilyl)amide | LHMDS |
| Dimethylaminopyridine | DMAP |
| Retention time | $R_t$ |

Intermediate 1:
9-benzyl-9-azabicyclo[3.3.1]nonan-2-ol

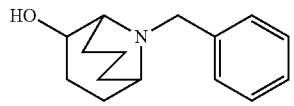 [SMILES: OC1CCC2CCCC1N2Cc1ccccc1]

To a solution of mercury(II) chloride (0.59 g, 2.16 mmol) in THF (3 mL) and water (3 mL) was added (Z)-8-(benzylamino)cyclooct-4-enol (0.50 g, 2.16 mmol) and the reaction mixture was stirred at room temperature overnight. The reaction mixture was cooled to 0° C. and 3 M NaOH (3 mL) was added followed by the addition of $NaBH_4$ (0.09 mg, 2.38 mmol) in 3 M NaOH (2.1 mL) and the reaction mixture was allowed to warm to room temperature and stir for 3 hours. Brine (10 mL) was added and the reaction mixture was extracted with EtOAc (3×10 mL). The organic layers were combined, dried with $Na_2SO_4$, concentrated and purified by flash column chromatography (40-100% EtOAc in hexanes) to provide 9-benzyl-9-azabicyclo[3.3.1]nonan-2-ol (0.35 g). $^1$H NMR (400 MHz, DMSO) δ 7.38-7.24 (m, 4H), 7.25-7.16 (m, 1H), 4.56 (d, J=4.7 Hz, 1H), 3.85 (d, J=3.9 Hz, 2H), 2.66-2.60 (m, 1H), 2.57 (d, J=4.2 Hz, 1H), 2.04-1.61 (m, 7H), 1.61-1.49 (m, 3H), 1.34-1.24 (m, 1H).

Intermediate 2: 9-benzyl-9-azabicyclo[3.3.1]nonan-2-one

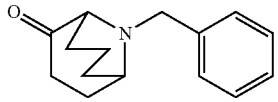

To a solution of oxalyl chloride (0.11 mL, 1.30 mmol) in DCM (30 mL) at −78° C. was added DMSO (0.19 mL, 2.59 mmol) and the reaction mixture was stirred for 10 minutes. 9-benzyl-9-azabicyclo[3.3.1]nonan-2-ol (0.20 g, 0.87 mmol) was added dropwise in DCM and the reaction mixture was stirred for 30 minutes at −78° C. Triethylamine (0.72 mL, 5.19 mmol) was added and the reaction mixture was allowed to warm to room temperature and stir overnight. Water (30 mL) was added and the reaction mixture was extracted with DCM (3×30 mL). The organic layers were combined, washed with saturated aqueous NaHCO₃, dried with Na₂SO₄, concentrated and purified by flash column chromatography (0-100% EtOAc in hexanes) to provide 9-benzyl-9-azabicyclo[3.3.1]nonan-2-one (0.20 mg). ¹H NMR (600 MHz, DMSO) δ 7.31 (d, J=4.4 Hz, 4H), 7.26-7.21 (m, 1H), 3.86-3.80 (m, 1H), 3.78-3.73 (m, 1H), 3.03-2.95 (m, 2H), 2.64-2.56 (m, 1H), 2.45-2.34 (m, 2H), 1.97-1.88 (m, 1H), 1.87-1.78 (m, 1H), 1.78-1.69 (m, 1H), 1.61-1.53 (m, 2H), 1.51-1.41 (m, 2H).

Intermediate 3: Ethyl 9-benzyl-2-oxo-9-azabicyclo[3.3.1]nonane-3-carboxylate

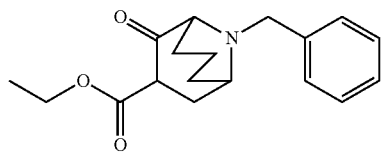 [SMILES: CCOC(=O)C1CC2CCCC(C1=O)N2Cc1ccccc1]

To a solution of 9-benzyl-9-azabicyclo[3.3.1]nonan-2-one (1.80 g, 7.85 mmol) in THF (50 mL) at −78° C. was added 1.06 M LHMDS (8.89 mL, 9.42 mmol) and the reaction mixture was stirred for 30 minutes. Ethyl cyanoformate (1.00 mL, 10.20 mmol) in THF (5 mL) was added dropwise and the reaction mixture was stirred for 2 hours at −78° C. A saturated aqueous NH₄Cl solution (20 mL) was added, the reaction mixture was warmed to room temperature and extracted with EtOAc (3×20 mL). The organic layers were combined, washed with brine, dried with Na₂SO₄, concentrated and purified by flash column chromatography (0-100% EtOAc in hexanes) to provide ethyl 9-benzyl-2-oxo-9-azabicyclo[3.3.1]nonane-3-carboxylate (2.03 g).

Intermediate 4: 11-benzyl-2-methyl-5,6,7,8,9,10-hexahydro-6,10-epiminocycloocta[d]pyrimidin-4-ol

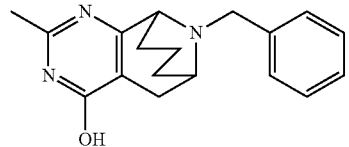 [SMILES: Cc1nc(O)c2c(n1)C1CCCC(C2)N1Cc1ccccc1]

To a solution of 9-benzyl-2-oxo-9-azabicyclo[3.3.1]nonane-3-carboxylate (2.00 g, 6.64 mmol) in ethanol (7 mL) was added acetamide hydrochloride (2.07 g, 21.67 mmol) followed by the addition of 0.5 M sodium ethoxide (10.34 mL, 5.17 mmol). The reaction mixture was heated to reflux for 12 hours. The reaction mixture was cooled to room temperature, concentrated and the resulting residue was dissolved in DCM (10 mL) and water (10 mL). The pH of the aqueous layer was adjusted to pH 6 and extracted with 5% butanol in DCM (4×10 mL). The organic layers were combined, dried with Na₂SO₄, concentrated and purified by flash column chromatography (0-15% MeOH in DCM) to provide 11-benzyl-2-methyl-5,6,7,8,9,10-hexahydro-6,10-epiminocycloocta[d]pyrimidin-4-ol (0.35 g). 1H NMR (500 MHz, DMSO) δ 12.40-12.13 (s, 1H), 7.42-7.16 (m, 5H), 3.62-3.53 (m, 1H), 3.54-3.46 (m, 1H), 3.40-3.35 (s, 1H), 3.17-3.05 (s, 1H), 2.72-2.60 (m, 1H), 2.28-2.19 (s, 3H), 2.13-2.02 (d, J=18.5 Hz, 1H), 1.85-1.72 (m, 3H), 1.60-1.47 (m, 2H), 1.46-1.36 (d, J=13.6 Hz, 1H).

Intermediate 5: 11-benzyl-2-methyl-5,6,7,8,9,10-hexahydro-6,10-epiminocycloocta[d]pyrimidin-4-yl 4-methylbenzenesulfonate

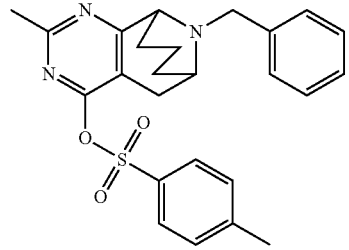 [SMILES: Cc1ccc(S(=O)(=O)Oc2nc(C)nc3c2CC2CCCC3N2Cc2ccccc2)cc1]

To a solution of 11-benzyl-2-methyl-5,6,7,8,9,10-hexahydro-6,10-epiminocycloocta[d]pyrimidin-4-ol (0.24 g, 0.81 mmol) in DCM (10 mL) at 0° C. was added p-toluenesulfonyl chloride (0.17 g, 0.89 mmol) followed by triethylamine (0.34 mL, 2.44 mmol) and DMAP (0.99 mg, 0.01 mmol). The reaction mixture was allowed to warm to room temperature and stir overnight. The reaction mixture was concentrated and purified by flash column chromatography (0-100% EtOAc in hexanes) to provide 11-benzyl-2-methyl-5,6,7,8,9,10-hexahydro-6,10-epiminocycloocta[d]pyrimidin-4-yl 4-methylbenzenesulfonate (0.21 g). ¹H NMR (600 MHz, DMSO) δ 8.02-7.96 (m, 2H), 7.55-7.50 (m, 2H), 7.34-7.19 (m, 5H), 3.71-3.61 (m, 1H), 3.60-3.54 (m, 1H), 3.52-3.45 (m, 1H), 3.19 (m, 1H), 2.96-2.88 (m, 1H), 2.45 (d, J=8.6 Hz, 6H), 2.30 (d, J=18.3 Hz, 1H), 1.96-1.86 (m, 1H), 1.86-1.76 (m, 1H), 1.59-1.46 (m, 2H), 1.43-1.35 (m, 1H), 1.02-0.83 (m, 1H).

Intermediate 6: 11-benzyl-2-methyl-4-(1-(tetrahydro-2H-pyran-2-yl)-1H-pyrazol-5-yl)-5,6,7,8,9,10-hexahydro-6,10-epiminocycloocta[d]pyrimidine

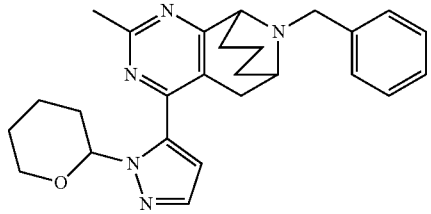 [SMILES: Cc1nc(-c2ccnn2C2CCCCO2)c2c(n1)C1CCCC(C2)N1Cc1ccccc1]

To a solution of 11-benzyl-2-methyl-5,6,7,8,9,10-hexahydro-6,10-epiminocycloocta[d]pyrimidin-4-yl 4-methylbenzenesulfonate (0.21 g, 0.46 mmol) in dioxane (5 mL) and water (1 mL) was added 1-(2-tetrahydropyranyl)-1H-pyrazole-5-boronic acid pinacol ester (0.30, 1.07 mmol), tetrakis(triphenylphosphine)palladium (0.06 g, 0.05 mmol), and sodium carbonate (0.17 g, 1.60 mmol). A gentle stream of nitrogen was bubbled through the reaction mixture for 30 minutes. The reaction vessel was sealed and the reaction mixture was heated to 100° C. for 17 hours. The reaction was cooled to room temperature, diluted with EtOAc (30 mL) and washed with water (30 mL). The organic layer was dried with $Na_2SO_4$, concentrated and purified by flash column chromatography (0-100% EtOAc in hexanes) to provide 11-benzyl-2-methyl-4-(1-(tetrahydro-2H-pyran-2-yl)-1H-pyrazol-5-yl)-5,6,7,8,9,10-hexahydro-6,10-epiminocycloocta[d]pyrimidine (0.19 g). $^1$H NMR (400 MHz, DMSO) δ 7.67-7.61 (m, 1H), 7.37-7.20 (m, 5H), 6.80-6.73 (m, 1H), 5.64-5.49 (m, 1H), 3.78-3.44 (m, 3H), 3.42-3.34 (m, 1H), 3.31-3.22 (m, 1H), 3.21-3.07 (m, 2H), 2.96-2.84 (m, 1H), 2.60 (d, J=2.1 Hz, 3H), 2.45-2.15 (m, 2H), 2.03-1.76 (m, 4H), 1.69-1.52 (m, 2H), 1.52-1.35 (m, 4H).

Intermediate 7: 2-methyl-4-(1-(tetrahydro-2H-pyran-2-yl)-1H-pyrazol-5-yl)-5,6,7,8,9,10-hexahydro-6,10-epiminocycloocta[d]pyrimidine

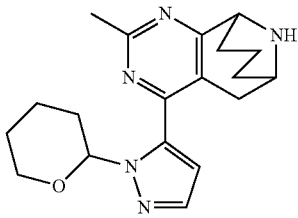 [SMILES: Cc1nc(-c2ccnn2C2CCCCO2)c2c(n1)C1CCCC(C2)N1]

To a solution of 11-benzyl-2-methyl-4-(1-(tetrahydro-2H-pyran-2-yl)-1H-pyrazol-5-yl)-5,6,7,8,9,10-hexahydro-6,10-epiminocycloocta[d]pyrimidine (185 mg, 0.43 mmol) in methanol (5 mL) was added 10% Palladium on Carbon (Pd/C, 9 mg) and the reaction mixture was stirred at room temperature under an atmosphere of hydrogen for 12 hours. The reaction mixture was filtered through a pad of celite, concentrated and used without further purification.

Intermediate 8: (2-chloro-3-(trifluoromethyl)phenyl)(2-methyl-4-(1-(tetrahydro-2H-pyran-2-yl)-1H-pyrazol-5-yl)-5,6,7,8,9,10-hexahydro-6,10-epiminocycloocta[d]pyrimidin-11-yl)methanone

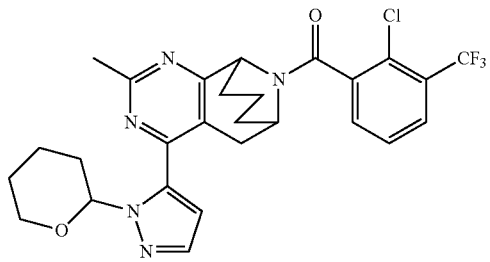 [SMILES: Cc1nc(-c2ccnn2C2CCCCO2)c2c(n1)C1CCCC(C2)N1C(=O)c1cccc(C(F)(F)F)c1Cl]

To a solution of 2-methyl-4-(1-(tetrahydro-2H-pyran-2-yl)-1H-pyrazol-5-yl)-5,6,7,8,9,10-hexahydro-6,10-epiminocycloocta[d]pyrimidine (75 mg, 0.22 mmol) in DCM at 0° C. was added 2-chloro-3-(trifluoromethyl)-benzoyl chloride (64 mg, 0.27 mmol) followed by the addition of triethylamine (0.09 mL, 0.66 mmol). The resulting reaction mixture was warmed to room temperature and stirred overnight. The reaction mixture was concentrated onto silica gel and purified by flash column chromatography (0-100% EtOAc in hexanes) to provide (2-chloro-3-(trifluoromethyl)phenyl)(2-methyl-4-(1-(tetrahydro-2H-pyran-2-yl)-1H-pyrazol-5-yl)-5,6,7,8,9,10-hexahydro-6,10-epiminocycloocta[d]pyrimidin-11-yl)methanone. MS (ESI): mass calcd. for $C_{27}H_{27}ClF_3N_5O_2$, 545.18; m/z found, 546.2 [M+H]$^+$.

Intermediate 9: (2,3-dichlorophenyl)(2-methyl-4-(1-(tetrahydro-2H-pyran-2-yl)-1H-pyrazol-5-yl)-5,6,7,8,9,10-hexahydro-6,10-epiminocycloocta[d]pyrimidin-11-yl)methanone

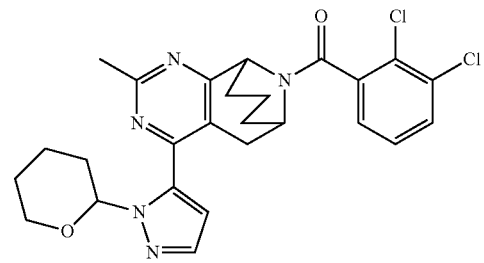 [SMILES: Cc1nc(-c2ccnn2C2CCCCO2)c2c(n1)C1CCCC(C2)N1C(=O)c1cccc(Cl)c1Cl]

Intermediate 9 was prepared in analogous fashion to intermediate 8 employing 2,3-dicholorobenzoyl chloride in place of 2-chloro-3-(trifluoromethyl)-benzoyl chloride. MS (ESI): mass calcd. for $C_{26}H_{27}Cl_2N_5O_2$, 511.15; m/z found, 512.2 [M+H]$^+$.

Intermediate 10: (1R,2S,5S)-9-((R)-1-phenylethyl)-9-azabicyclo[3.3.1]nonan-2-ol

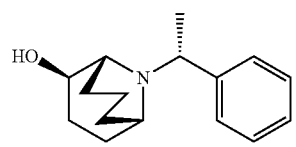 [SMILES: C[C@H](c1ccccc1)N1[C@H]2CCC[C@@H]1[C@H](O)CC2]

Intermediate 10 was prepared in analogous fashion to intermediate 1 employing (1S,8S,Z)-8-(((R)-1-phenylethyl)amino)cyclooct-4-enol in place of (Z)-8-(benzylamino)cyclooct-4-enol. $^1$H NMR (400 MHz, DMSO) δ 7.38-7.24 (m, 4H), 7.23-7.14 (m, 1H), 4.46 (d, J=4.6 Hz, 1H), 4.17-4.08 (m, 1H), 3.73-3.63 (m, 1H), 2.94 (s, 1H), 2.58-2.51 (m, 1H), 1.97-1.47 (m, 10H), 1.21-1.12 (m, 3H).

Intermediate 11: (1R,2S,5S)-9-((R)-1-phenylethyl)-9-azabicyclo[3.3.1]nonan-2-ol

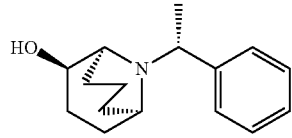 [SMILES: C[C@H](c1ccccc1)N1[C@@H]2CCC[C@H]1[C@H](O)CC2]

Intermediate 11 was prepared in analogous fashion to intermediate 1 employing (1R,8R,Z)-8-(((R)-1-phenylethyl)amino)cyclooct-4-enol in place of (Z)-8-(benzylamino)cyclooct-4-enol. $^1$H NMR (400 MHz, DMSO) δ 7.38-7.24 (m, 4H), 7.23-7.14 (m, 1H), 4.46 (d, J=4.6 Hz, 1H), 4.17-4.08 (m, 1H), 3.73-3.63 (m, 1H), 2.94 (s, 1H), 2.58-2.51 (m, 1H), 1.97-1.47 (m, 10H), 1.21-1.12 (m, 3H).

Intermediate 12: (1R,2S,5S)-tert-butyl 2-hydroxy-9-azabicyclo[3.3.1]nonane-9-carboxylate

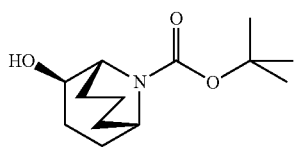 [SMILES: CC(C)(C)OC(=O)N1[C@H]2CCC[C@@H]1[C@H](O)CC2]

To a solution of (1R,2S,5S)-9-((R)-1-phenylethyl)-9-azabicyclo[3.3.1]nonan-2-ol (5.36 g, 21.55 mmol) in methanol (300 mL) was added 10% Pd/C (2.3 g) and the reaction mixture was placed under a hydrogen atmosphere and stirred at room temperature for 12 hours. To the reaction mixture was added BOC-anhydride (5.61 mL, 26.21 mmol) and the reaction mixture was stirred for 5 hours. The reaction mixture was filtered through a pad of celite, concentrated and purified by flash column chromatography (0-30% EtOAc in hexanes) to provide (1R,2S,5S)-tert-butyl 2-hydroxy-9-azabicyclo[3.3.1]nonane-9-carboxylate (4.1 g). $^1$H NMR (400 MHz, DMSO) δ 4.99-4.89 (m, 1H), 4.06-3.87 (m, 2H), 3.67-3.53 (m, 1H), 1.99-1.41 (m, 10H), 1.39 (d, J=1.0 Hz, 9H).

Intermediate 13: (1S,2R,5R)-tert-butyl 2-hydroxy-9-azabicyclo[3.3.1]nonane-9-carboxylate

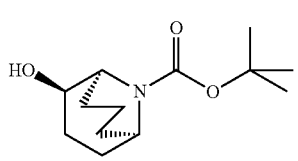 [SMILES: CC(C)(C)OC(=O)N1[C@@H]2CCC[C@H]1[C@H](O)CC2]

Intermediate 13 was prepared in analogous fashion to intermediate 12 employing (1S,2R,5R)-9-((R)-1-phenylethyl)-9-azabicyclo[3.3.1]nonan-2-ol in place of (1R,2S,5S)-9-((R)-1-phenylethyl)-9-azabicyclo[3.3.1]nonan-2-ol.). $^1$H NMR (400 MHz, DMSO) δ 4.99-4.89 (m, 1H), 4.06-3.87 (m, 2H), 3.67-3.53 (m, 1H), 1.99-1.41 (m, 10H), 1.39 (d, J=1.0 Hz, 9H).

Intermediate 14: (1R,5S)-tert-butyl 2-oxo-9-azabicyclo[3.3.1]nonane-9-carboxylate

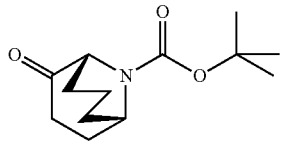 [SMILES: CC(C)(C)OC(=O)N1[C@H]2CCC[C@@H]1C(=O)CC2]

To a solution of oxalyl chloride (2.31 mL, 26.91 mmol) in DCM (180 mL) at −78° C. was added DMSO (3.85 mL, 53.83 mmol) and the reaction mixture was stirred for minutes. (1R,2S,5S)-tert-butyl 2-hydroxy-9-azabicyclo[3.3.1]nonane-9-carboxylate (4.33, 17.94 mmol) was added dropwise in DCM (10 mL) and the reaction mixture was stirred for 30 minutes at −78° C. Triethylamine (14.96 mL, 107.65 mmol) was added and the reaction mixture was allowed to warm to room temperature and stir overnight. Water (50 mL) was added and the reaction mixture was extracted with DCM (3×50 mL). The organic layers were combined, washed with saturated aqueous NaHCO$_3$, dried with Na$_2$SO$_4$, concentrated, and purified by flash column chromatography (0-100% EtOAc in hexanes) to provide (1R,5S)-tert-butyl 2-oxo-9-azabicyclo[3.3.1]nonane-9-carboxylate (4.50 g). $^1$H NMR (500 MHz, DMSO) δ 4.42 (d, J=17.9 Hz, 1H), 4.29 (d, J=22.7 Hz, 1H), 2.42-2.23 (m, 3H), 1.79 (d, J=10.9 Hz, 1H), 1.73-1.20 (m, 15H).

Intermediate 15: (1R,5S)-tert-butyl 2-oxo-9-azabicyclo[3.3.1]nonane-9-carboxylate

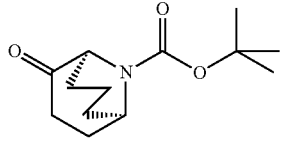 [SMILES: CC(C)(C)OC(=O)N1[C@@H]2CCC[C@H]1C(=O)CC2]

Intermediate 15 was prepared in analogous fashion to intermediate 14 employing (1S,2R,5R)-9-((R)-1-phenylethyl)-9-azabicyclo[3.3.1]nonan-2-ol in place of (1R,2S,5S)-9-((R)-1-phenylethyl)-9-azabicyclo[3.3.1]nonan-2-ol.). $^1$H NMR (500 MHz, DMSO) δ 4.42 (d, J=17.9 Hz, 1H), 4.29 (d, J=22.7 Hz, 1H), 2.42-2.23 (m, 3H), 1.79 (d, J=10.9 Hz, 1H), 1.73-1.20 (m, 15H).

Intermediate 16: (1R,5S)-9-tert-butyl 3-ethyl 2-oxo-9-azabicyclo[3.3.1]nonane-3,9-dicarboxylate

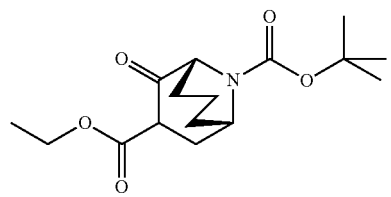 [SMILES: CCOC(=O)C1C[C@@H]2CCC[C@H](C1=O)N2C(=O)OC(C)(C)C]

To a solution of (1R,5S)-tert-butyl 2-oxo-9-azabicyclo[3.3.1]nonane-9-carboxylate (4.10 g, 17.13 mmol) in THF (200 mL) at −78° C. was added 1.06M LHMDS in THF (19.40 mL, 20.56 mmol) and the reaction mixture was stirred at −78° C. for 30 minutes. Ethyl cyanoformate (2.18 mL, 22.27 mmol) in THF (10 mL) was added dropwise and the reaction mixture was stirred at −78° C. for 5 hours. Saturated aqueous NH₄Cl (20 mL) was added and the reaction mixture was extracted with EtOAc (3×50 mL). The organic layers were combined, washed with brine, dried, concentrated and purified by flash column chromatography (0-100% EtOAc in hexanes) to provide (1R,5S)-9-tert-butyl 3-ethyl 2-oxo-9-azabicyclo[3.3.1]nonane-3,9-dicarboxylate (3.8 g).

Intermediate 17: (1S,5R)-9-tert-butyl 3-ethyl 2-oxo-9-azabicyclo[3.3.1]nonane-3,9-dicarboxylate

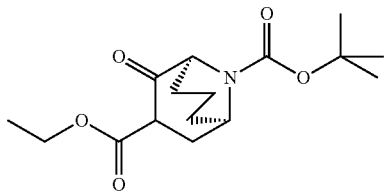 [SMILES: CCOC(=O)C1C[C@H]2CCC[C@@H](C1=O)N2C(=O)OC(C)(C)C]

Intermediate 17 was generated in a fashion analogous to intermediate 16 employing (1S,5R)-tert-butyl 2-oxo-9-azabicyclo[3.3.1]nonane-9-carboxylate in place of (1R,5S)-tert-butyl 2-oxo-9-azabicyclo[3.3.1]nonane-9-carboxylate.

Intermediate 18: (6S,10R)-tert-butyl 4-hydroxy-2-methyl-5,6,7,8,9,10-hexahydro-6,10-epiminocycloocta[d]pyrimidine-11-carboxylate

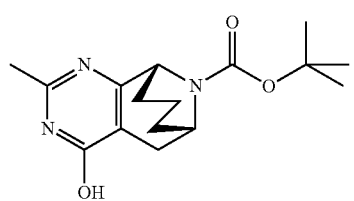 [SMILES: Cc1nc(O)c2c(n1)[C@H]1CCC[C@@H](C2)N1C(=O)OC(C)(C)C]

To a solution of (1R,5S)-9-tert-butyl 3-ethyl 2-oxo-9-azabicyclo[3.3.1]nonane-3,9-dicarboxylate (2.75 g, 8.83 mmol) in ethanol (13 mL) was added acetamide hydrochloride (2.53 g, 26.50 mmol) followed by 21% sodium ethoxide (9.89 mL) and the reaction mixture was heated to reflux for 12 hours. The reaction mixture was cooled to room temperature and concentrated under reduced pressure. The resulting residue was dissolved in DCM (100 mL) and water (100 mL) and the pH of the aqueous layer was adjusted to pH 6. The organic layer was collected and the aqueous layer was extracted with DCM (5×30 mL). The organic layers were collected, dried, concentrated and purified by flash column chromatography (30-100% EtOAc in hexanes) to provide (6S,10R)-tert-butyl 4-hydroxy-2-methyl-5,6,7,8,9,10-hexahydro-6,10-epiminocycloocta[d]pyrimidine-11-carboxylate (2.16 g). ¹H NMR (400 MHz, DMSO) δ 12.35 (s, 1H), 4.68 (d, J=17.0 Hz, 1H), 4.44 (d, J=16.5 Hz, 1H), 2.64 (d, J=17.4 Hz, 2H), 2.25 (s, 3H), 1.95-1.02 (m, 15H).

Intermediate 19: (6R,10S)-tert-butyl 4-hydroxy-2-methyl-5,6,7,8,9,10-hexahydro-6,10-epiminocycloocta[d]pyrimidine-11-carboxylate

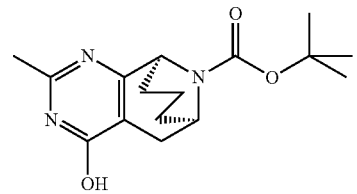 [SMILES: Cc1nc(O)c2c(n1)[C@@H]1CCC[C@H](C2)N1C(=O)OC(C)(C)C]

Intermediate 19 was generated in analogous fashion to intermediate 18 by employing (1S,5R)-9-tert-butyl 3-ethyl 2-oxo-9-azabicyclo[3.3.1]nonane-3,9-dicarboxylate in place of (1R,5S)-9-tert-butyl 3-ethyl 2-oxo-9-azabicyclo[3.3.1]nonane-3,9-dicarboxylate. ¹H NMR (400 MHz, DMSO) δ 12.35 (s, 1H), 4.68 (d, J=17.0 Hz, 1H), 4.44 (d, J=16.5 Hz, 1H), 2.64 (d, J=17.4 Hz, 2H), 2.25 (s, 3H), 1.97-1.06 (m, 15H).

Intermediate 20: (6S,10R)-tert-butyl 2-methyl-4-(tosyloxy)-5,6,7,8,9,10-hexahydro-6,10-epiminocycloocta[d]pyrimidine-11-carboxylate

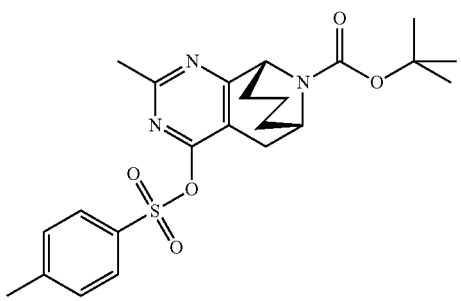 [SMILES: Cc1ccc(S(=O)(=O)Oc2nc(C)nc3c2C[C@@H]2CCC[C@H]3N2C(=O)OC(C)(C)C)cc1]

To a solution of (6S,10R)-tert-butyl 4-hydroxy-2-methyl-5,6,7,8,9,10-hexahydro-6,10-epiminocycloocta[d]pyrimidine-11-carboxylate (2.70 g, 8.84 mmol) in DCM (30 mL) at 0° C. was added p-toluenesulfonyl chloride (1.85 g, 9.73 mmol), triethylamine (3.69 mL, 26.53 mmol) and DMAP (10 mg). The reaction mixture was allowed to warm to room temperature and stir overnight. The reaction mixture was concentrated and purified by flash column chromatography (0-100% EtOAc in hexanes) to provide (6S,10R)-tert-butyl 2-methyl-4-(tosyloxy)-5,6,7,8,9,10-hexahydro-6,10-epiminocycloocta[d]pyrimidine-11-carboxylate (3.8 g). ¹H NMR (400 MHz, DMSO) δ 7.99 (d, J=8.4 Hz, 1H), 7.52 (d, J=8.1 Hz, 2H), 4.97 (d, J=10.3 Hz, 1H), 4.52 (s, 1H), 3.00-2.85 (m, 1H), 2.57-2.36 (m, 10H), 1.82-1.57 (m, 4H), 1.38 (s, 8H), 1.14-0.89 (m, 1H).

Intermediate 21: (6R,10S)-tert-butyl 2-methyl-4-(tosyloxy)-5,6,7,8,9,10-hexahydro-6,10-epiminocycloocta[d]pyrimidine-11-carboxylate

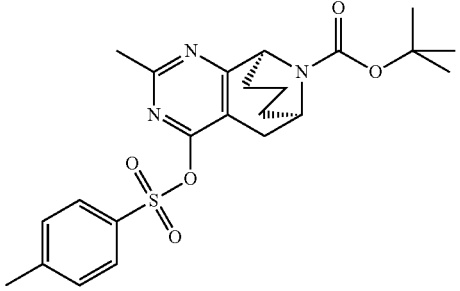 [SMILES: Cc1ccc(S(=O)(=O)Oc2nc(C)nc3c2C[C@H]2CCC[C@@H]3N2C(=O)OC(C)(C)C)cc1]

Intermediate 21 was generated in a manner analogous to the described for intermediate 20 employing (6R,10S)-tert-butyl 4-hydroxy-2-methyl-5,6,7,8,9,10-hexahydro-6,10-epiminocycloocta[d]pyrimidine-11-carboxylate in place of (6S,10R)-tert-butyl 4-hydroxy-2-methyl-5,6,7,8,9,10-hexahydro-6,10-epiminocycloocta[d]pyrimidine-11-carboxylate. $^1$H NMR (400 MHz, DMSO) δ 7.99 (d, J=8.4 Hz, 1H), 7.52 (d, J=8.1 Hz, 2H), 4.97 (d, J=10.3 Hz, 1H), 4.52 (s, 1H), 3.00-2.85 (m, 1H), 2.57-2.36 (m, 10H), 1.82-1.57 (m, 4H), 1.38 (s, 8H), 1.14-0.89 (m, 1H).

Intermediate 22: (6S,10R)-tert-butyl 2-methyl-4-(1-(tetrahydro-2H-pyran-2-yl)-1H-pyrazol-3-yl)-5,6,7,8,9,10-hexahydro-6,10-epiminocycloocta[d]pyrimidine-11-carboxylate

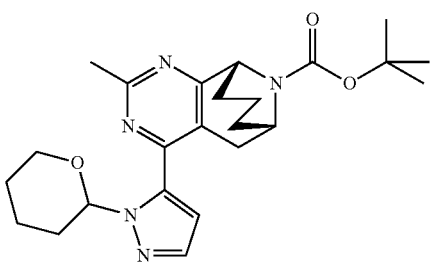 [SMILES: Cc1nc(-c2ccnn2C2CCCCO2)c2c(n1)[C@H]1CCC[C@@H](C2)N1C(=O)OC(C)(C)C]

To a solution of (6S,10R)-tert-butyl 2-methyl-4-(tosyloxy)-5,6,7,8,9,10-hexahydro-6,10-epiminocycloocta[d]pyrimidine-11-carboxylate (1.00 g, 2.18 mmol) in dioxane (15 mL) and water (4 mL) was added 1-(2-tetrahydropyranyl)-1H-pyrazole-5-boronic acid pinacol ester (1.41, 5.07 mmol), tetrakis(triphenylphosphine)palladium(0) (0.50 g, 0.44 mmol), and sodium carbonate (0.80 g, 7.60 mmol). A gentle stream of nitrogen was bubbled through the reaction mixture for 30 minutes. The reaction vessel was sealed and the reaction mixture was heated to 100° C. for 17 hours. The reaction was cooled to room temperature, diluted with EtOAc (60 mL) and washed with water (30 mL). The organic layer was dried with Na$_2$SO$_4$, concentrated and purified by flash column chromatography (0-100% EtOAc in hexanes) to provide (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate (0.90 g). MS (ESI): mass calculated for C$_{24}$H$_{33}$N$_5$O$_3$, 439.6; m/z found 440.3 [M+H]$^+$.

Intermediate 23: (6R,10S)-tert-butyl 2-methyl-4-(1-(tetrahydro-2H-pyran-2-yl)-1H-pyrazol-3-yl)-5,6,7,8,9,10-hexahydro-6,10-epiminocycloocta[d]pyrimidine-11-carboxylate

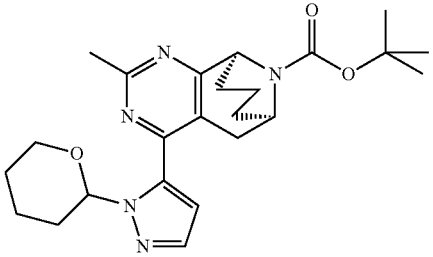 [SMILES: Cc1nc(-c2ccnn2C2CCCCO2)c2c(n1)[C@@H]1CCC[C@H](C2)N1C(=O)OC(C)(C)C]

Example 23 was generated in analogous fashion to example 22 wherein (6R,10S)-tert-butyl 2-methyl-4-(tosyloxy)-5,6,7,8,9,10-hexahydro-6,10-epiminocycloocta[d]pyrimidine-11-carboxylate was used in place of (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate. MS (ESI): mass calculated for C$_{24}$H$_{33}$N$_5$O$_3$, 439.6; m/z found 440.3 [M+H]$^+$.

Intermediate 24: (6S,10R)-2-methyl-4-(1H-pyrazol-5-yl)-5,6,7,8,9,10-hexahydro-6,10-epiminocycloocta[d]pyrimidine

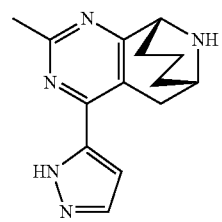 [SMILES: Cc1nc(-c2ccn[nH]2)c2c(n1)[C@H]1CCC[C@@H](C2)N1]

To a solution of (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate (1.50 g, 3.41 mmol) in methanol (54 mL) was added 4M HCl in dioxane (4.27 mL, 17.06 mmol) and the reaction mixture was stirred at room temperature for 1 hour. The reaction mixture was concentrated to provide (6S,10R)-2-methyl-4-(1H-pyrazol-5-yl)-5,6,7,8,9,10-hexahydro-6,10-epiminocycloocta[d]pyrimidine which was used without further purification. MS (ESI): mass calculated for C$_{14}$H$_{17}$N$_5$, 255.3; m/z found 256.2 [M+H]$^+$.

Intermediate 25: (6R,10S)-2-methyl-4-(1H-pyrazol-5-yl)-5,6,7,8,9,10-hexahydro-6,10-epiminocycloocta[d]pyrimidine

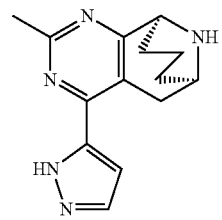 [SMILES: Cc1nc(-c2ccn[nH]2)c2c(n1)[C@@H]1CCC[C@H](C2)N1]

Intermediate 25 was generated in analogous fashion to intermediate 24 wherein (6R,10S)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate was used in place of (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate. MS (ESI): mass calculated for $C_{14}H_{17}N_5$, 255.3; m/z found 256.1 [M+H]$^+$.

Intermediate 26: (6R,10S)-tert-butyl 4-(4-fluorophenyl)-2-methyl-5,6,7,8,9,10-hexahydro-6,10-epiminocycloocta[d]pyrimidine-11-carboxylate

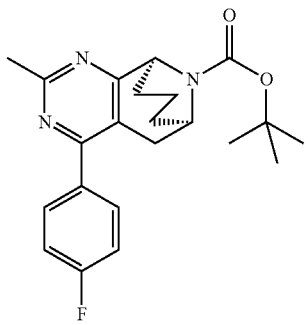 [SMILES: Cc1nc(-c2ccc(F)cc2)c2c(n1)[C@@H]1CCC[C@H](C2)N1C(=O)OC(C)(C)C]

Intermediate 26 was generated in analogous fashion to intermediate 22 where in 4-fluorophenylboronic acid was used in place of 1-(2-tetrahydropyranyl)-1H-pyrazole-5-boronic acid pinacol ester. MS (ESI): mass calculated for $C_{22}H_{26}FN_3O_2$, 383.5; m/z found 384.2 [M+H]$^+$.

Intermediate 27: (6R,10S)-4-(4-fluorophenyl)-2-methyl-5,6,7,8,9,10-hexahydro-6,10-epiminocycloocta[d]pyrimidine

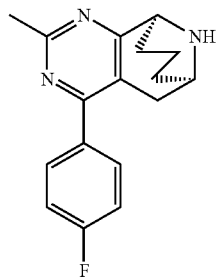 [SMILES: Cc1nc(-c2ccc(F)cc2)c2c(n1)[C@@H]1CCC[C@H](C2)N1]

To a solution of (6R,10S)-tert-butyl 4-(4-fluorophenyl)-2-methyl-5,6,7,8,9,10-hexahydro-6,10-epiminocycloocta[d]pyrimidine-11-carboxylate (0.42 g, 10.9 mmol) in methanol (9.6 mL) was added 4 M HCl in dioxane (5.4 mL, 21.75 mmol) and the reaction mixture was stirred at room temperature for 1 hour. The reaction was concentrated to provide (6R,10S)-4-(4-fluorophenyl)-2-methyl-5,6,7,8,9,10-hexahydro-6,10-epiminocycloocta[d]pyrimidine (0.31 g). MS (ESI): mass calculated for $C_{17}H_{18}FN_3$, 283.5; m/z found 284.2 [M+H]$^+$.

Intermediate 28: (6S,10R)-tert-butyl 2-methyl-4-(1-methyl-1H-pyrazol-4-yl)-5,6,7,8,9,10-hexahydro-6,10-epiminocycloocta[d]pyrimidine-11-carboxylate

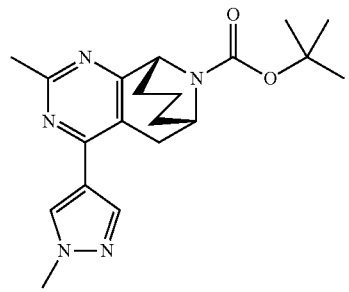 [SMILES: Cc1nc(-c2cnn(C)c2)c2c(n1)[C@H]1CCC[C@@H](C2)N1C(=O)OC(C)(C)C]

Intermediate 28 was synthesized in analogous fashion to intermediate 22 where in 1-methyl-4-(4,4,5,5-tetramethyl-1,2,3-dioxaborolan-2-yl)-1H-pyrazole was used in place of 1-(2-tetrahydropyranyl)-1H-pyrazole-5-boronic acid pinacol ester. MS (ESI): mass calculated for $C_{20}H_{27}N_5O_2$, 369.5; m/z found 370.2 [M+H]$^+$.

Intermediate 29: (6S,10R)-2-methyl-4-(1-methyl-1H-pyrazol-4-yl)-5,6,7,8,9,10-hexahydro-6,10-epiminocycloocta[d]pyrimidine

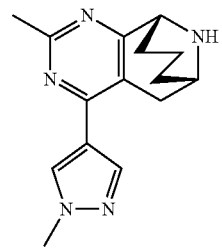 [SMILES: Cc1nc(-c2cnn(C)c2)c2c(n1)[C@H]1CCC[C@@H](C2)N1]

Intermediate 29 was generated in analogous fashion to intermediate 24 wherein (6S,10R)-tert-butyl 2-methyl-4-(1-methyl-1H-pyrazol-4-yl)-5,6,7,8,9,10-hexahydro-6,10-epiminocycloocta[d]pyrimidine-11-carboxylate was used in place of (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate.

Intermediate 30: (6S,10R)-tert-butyl 2-methyl-4-(pyrimidin-2-yl)-5,6,7,8,9,10-hexahydro-6,10-epiminocycloocta[d]pyrimidine-11-carboxylate

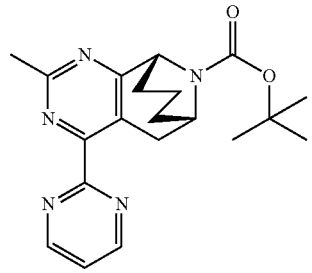 [SMILES: Cc1nc(-c2ncccn2)c2c(n1)[C@H]1CCC[C@@H](C2)N1C(=O)OC(C)(C)C]

To a solution of (6S,10R)-tert-butyl 2-methyl-4-(tosyloxy)-5,6,7,8,9,10-hexahydro-6,10-epiminocycloocta[d]pyrimidine-11-carboxylate (64 mg, 0.06 mmol) in dimethoxyethane (7.4 mL) was added copper iodide (10.6 mg, 0.06 mmol) and 2-(tributylstannyl)pyrimidine (0.45 mL, 1.33 mmol) and nitrogen was bubbled through the reaction mixture for 30 minutes. The reaction vessel was sealed and heated to 115° C. overnight. The reaction mixture was cooled to room temperature, diluted with EtOAc (20 mL) and water (20 mL) and potassium fluoride (50% wt. % on celite) was added. The resulting mixture was stirred for 1 hour, filtered through a pad of celite and extracted with EtOAc (2×30 mL). The organic layers were combined, dried with Na$_2$SO$_4$, filtered, concentrated, and purified by flash column chromatography (0-20% MeOH in EtOAc) to provide (6S,10R)-tert-butyl 2-methyl-4-(pyrimidin-2-yl)-5,6,7,8,9,10-hexahydro-6,10-epiminocycloocta[d]pyrimidine-11-carboxylate (333 mg). MS (ESI): mass calculated for C$_{20}$H$_{25}$N$_5$O$_2$, 367.5; m/z found 368.2 [M+H]$^+$.

Intermediate 31: (6S,10R)-2-methyl-4-(pyrimidin-2-yl)-5,6,7,8,9,10-hexahydro-6,10-epiminocycloocta[d]pyrimidine

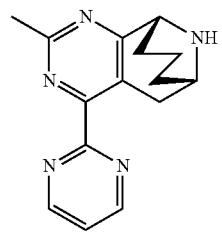 [SMILES: Cc1nc(-c2ncccn2)c2c(n1)[C@H]1CCC[C@@H](C2)N1]

Intermediate 31 was generated in a manner analogous to that described for intermediate 24 wherein (6S,10R)-tert-butyl 2-methyl-4-(pyrimidin-2-yl)-5,6,7,8,9,10-hexahydro-6,10-epiminocycloocta[d]pyrimidine-11-carboxylate was used in place of (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate.

Intermediate 32: (6S,10R)-tert-butyl 2-methyl-4-(pyrazin-2-yl)-5,6,7,8,9,10-hexahydro-6,10-epiminocycloocta[d]pyrimidine-11-carboxylate

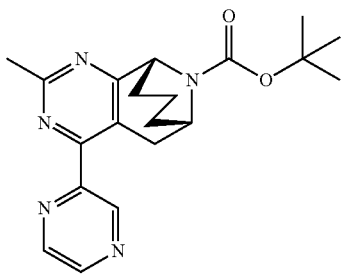 [SMILES: Cc1nc(-c2cnccn2)c2c(n1)[C@H]1CCC[C@@H](C2)N1C(=O)OC(C)(C)C]

Intermediate 32 was generated in a manner analogous to that described for intermediate 30 wherein 2-(tributylstannyl)pyrazine was used in place of 2-(tributylstannyl)pyridine. MS (ESI): mass calculated for C$_{20}$H$_{25}$N$_5$O$_2$, 367.5; m/z found 368.0 [M+H]$^+$.

Intermediate 32: (6S,10R)-2-methyl-4-(pyrazin-2-yl)-5,6,7,8,9,10-hexahydro-6,10-epiminocycloocta[d]pyrimidine

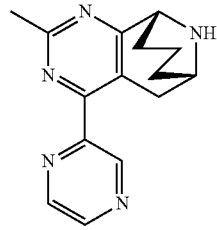 [SMILES: Cc1nc(-c2cnccn2)c2c(n1)[C@H]1CCC[C@@H](C2)N1]

Intermediate 32 was generated in a manner analogous to that described for intermediate 24 where in (6S,10R)-tert-butyl 2-methyl-4-(pyrazin-2-yl)-5,6,7,8,9,10-hexahydro-6,10-epiminocycloocta[d]pyrimidine-11-carboxylate was used in place of (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate.

Intermediate 33: (6S,10R)-tert-butyl 4-(4-fluorophenyl)-2-methyl-5,6,7,8,9,10-hexahydro-6,10-epiminocycloocta[d]pyrimidine-11-carboxylate

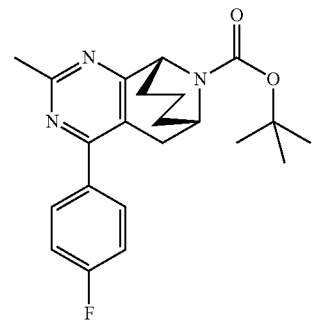 [SMILES: Cc1nc(-c2ccc(F)cc2)c2c(n1)[C@H]1CCC[C@@H](C2)N1C(=O)OC(C)(C)C]

Intermediate 33 was generated in a manner analogous to that described for intermediate 22 wherein 4-fluorophenylboronic acid was used in place of 1-(2-tetrahydropyranyl)-1H-pyrazole-5-boronic acid pinacol ester MS (ESI): mass calculated for C$_{20}$H$_{25}$N$_5$O$_2$, 367.5; m/z found 368.0 [M+H]$^+$.

Intermediate 34: (6S,10R)-4-(4-fluorophenyl)-2-methyl-5,6,7,8,9,10-hexahydro-6,10-epiminocycloocta[d]pyrimidine

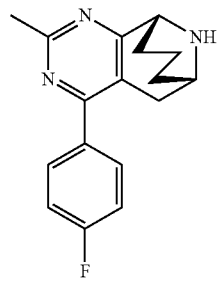 [SMILES: Cc1nc(-c2ccc(F)cc2)c2c(n1)[C@H]1CCC[C@@H](C2)N1]

Intermediate 34 was generated in an analogous fashion to that described for intermediate 24 where in (6S,10R)-tert-butyl 4-(4-fluorophenyl)-2-methyl-5,6,7,8,9,10-hexahydro-6,10-epiminocycloocta[d]pyrimidine-11-carboxylate was used in place of (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate.

Intermediate 35: (6S,10R)-tert-butyl 2-methyl-4-(1-methyl-1H-pyrazol-5-yl)-5,6,7,8,9,10-hexahydro-6,10-epiminocycloocta[d]pyrimidine-11-carboxylate

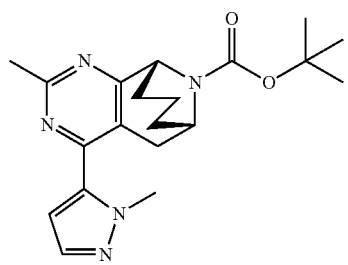 [SMILES: Cc1nc(-c2ccnn2C)c2c(n1)[C@H]1CCC[C@@H](C2)N1C(=O)OC(C)(C)C]

Intermediate 35 was generated in a manner analogous to that described for intermediate 22 wherein 1-methyl-1H-pyrazole-5-boronic acid pinacol ester was used in place of 1-(2-tetrahydropyranyl)-1H-pyrazole-5-boronic acid pinacol ester MS (ESI): mass calculated for $C_{20}H_{27}N_5O_2$, 369.5; m/z found 370.0 [M+H]$^+$.

Intermediate 36: (6S,10R)-2-methyl-4-(1-methyl-1H-pyrazol-5-yl)-5,6,7,8,9,10-hexahydro-6,10-epiminocycloocta[d]pyrimidine

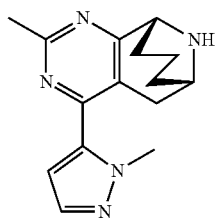 [SMILES: Cc1nc(-c2ccnn2C)c2c(n1)[C@H]1CCC[C@@H](C2)N1]

Intermediate 36 was generated in an analogous fashion to that described for intermediate 24 where in (6S,10R)-tert-butyl 2-methyl-4-(1-methyl-1H-pyrazol-5-yl)-5,6,7,8,9,10-hexahydro-6,10-epiminocycloocta[d]pyrimidine-11-carboxylate was used in place of (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate.

Intermediate 37: (6S,10R)-tert-butyl 2-methyl-4-(pyridin-2-yl)-5,6,7,8,9,10-hexahydro-6,10-epiminocycloocta[d]pyrimidine-11-carboxylate

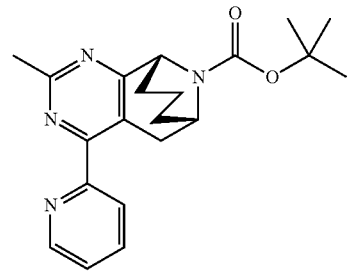 [SMILES: Cc1nc(-c2ccccn2)c2c(n1)[C@H]1CCC[C@@H](C2)N1C(=O)OC(C)(C)C]

Intermediate 37 was generated in a manner analogous to that described for intermediate 30 wherein 2-(tributylstannyl)pyridine was used in place of 2-(tributylstannyl)pyrimidine. MS (ESI): mass calculated for $C_{21}H_{26}N_4O_2$, 366.5; m/z found 367.0 [M+H]$^+$.

Intermediate 38: (6S,10R)-2-methyl-4-(pyridin-2-yl)-5,6,7,8,9,10-hexahydro-6,10-epiminocycloocta[d]pyrimidin

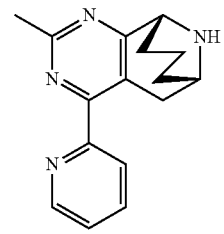

Intermediate 38 was generated in a manner analogous to that described for intermediate 24 wherein (6S,10R)-tert-butyl 2-methyl-4-(pyridin-2-yl)-5,6,7,8,9,10-hexahydro-6,10-epiminocycloocta[d]pyrimidine-11-carboxylate was used in place of (6S,10R)-tert-butyl 2-methyl-4-(1-(tetrahydro-2H-pyran-2-yl)-1H-pyrazol-5-yl)-5,6,7,8,9,10-hexahydro-6,10-epiminocycloocta[d]pyrimidine-11-carboxylate.

Example 1. (2,3-dichlorophenyl)(2-methyl-4-(1H-pyrazol-5-yl)-5,6,7,8,9,10-hexahydro-6,10-epiminocycloocta[d]pyrimidin-11-yl)methanone

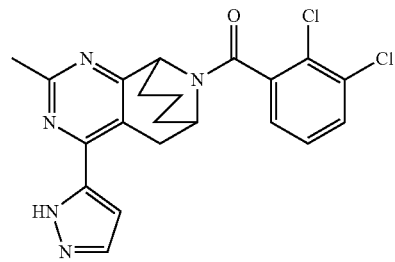 [SMILES: Cc1nc(-c2ccn[nH]2)c2c(n1)C1CCCC(C2)N1C(=O)c1cccc(Cl)c1Cl]

To a solution of (2,3-dichlorophenyl)(2-methyl-4-(1-(tetrahydro-2H-pyran-2-yl)-1H-pyrazol-5-yl)-5,6,7,8,9,10- hexahydro-6,10-epiminocycloocta[d]pyrimidin-11-yl) methanone (96.7 mg, 0.189 mmol) in DCM (5 mL) was added triethylsilane (0.09 mL, 0.57 mmol) and trifluoroacetic acid (0.07 mL), 0.94 mmol) and the reaction mixture was stirred for 1 hour at room temperature. The reaction mixture was diluted with DCM (20 mL) and washed with saturated aqueous NaHCO$_3$ (10 mL). The organic layer was dried, concentrated and purified by FCC (0-100% EtOAc in hexanes) to provide (2,3-dichlorophenyl)((6S,10R)-2-methyl-4-(1H-pyrazol-5-yl)-5,6,7,8,9,10-hexahydro-6,10-epiminocycloocta[d]pyrimidin-11-yl)methanone (55 mg, 81%). MS (ESI): mass calculated for C$_{21}$H$_{19}$Cl$_2$ON$_5$, 428.3; m/z found 428.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.159 min at 254 nm.

Example 2. (2-chloro-3-(trifluoromethyl)phenyl)(2-methyl-4-(1H-pyrazol-5-yl)-5,6,7,8,9,10-hexahydro-6,10-epiminocycloocta[d]pyrimidin-11-yl)methanone

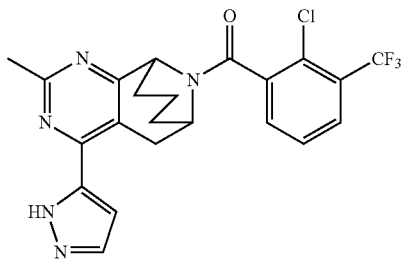 [SMILES: Cc1nc(-c2ccn[nH]2)c2c(n1)C1CCCC(C2)N1C(=O)c1cccc(C(F)(F)F)c1Cl]

Example 2 was generated in analogous fashion to example 1 wherein (2-chloro-3-(trifluoromethyl)phenyl)(2-methyl-4-(1-(tetrahydro-2H-pyran-2-yl)-1H-pyrazol-5-yl)-5,6,7,8,9,10-hexahydro-6,10-epiminocycloocta[d]pyrimidin-11-yl)methanone was used in place of (2,3-dichlorophenyl)(2-methyl-4-(1-(tetrahydro-2H-pyran-2-yl)-1H-pyrazol-5-yl)-5,6,7,8,9,10-hexahydro-6,10-epiminocycloocta[d]pyrimidin-11-yl)methanone (73 mg, 76%). MS (ESI): mass calculated for C$_{22}$H$_{19}$ClF$_3$ON$_5$, 461.9; m/z found 462.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.202 min at 254 nm.

Example 3. (2-chloro-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone

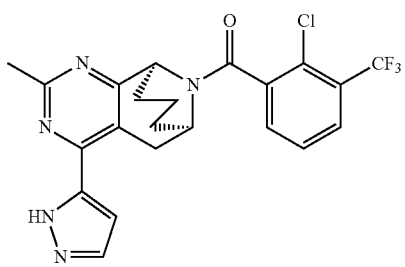 [SMILES: Cc1nc(-c2ccn[nH]2)c2c(n1)[C@@H]1CCC[C@H](C2)N1C(=O)c1cccc(C(F)(F)F)c1Cl]

To a suspension of (6R,10S)-2-methyl-4-(1H-pyrazol-5-yl)-5,6,7,8,9,10-hexahydro-6,10-epiminocycloocta[d]pyrimidine (84.2 mg, 0.33 mmol) in DCM (5 mL) was added BOP (175.1 mg, 0.40 mmol), 2-chloro-3-trifluoromethylbenzoic acid (74.1 mg, 0.33 mmol) followed by triethylamine (0.37 mL, 2.64 mmol) and the reaction mixture was stirred at room temperature overnight. The reaction mixture was directly purified by flash column chromatography (0-100% EtOAc in hexanes) to provide (2-chloro-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone (106 mg, 69%). MS (ESI): mass calculated for C$_{22}$H$_{19}$ClF$_3$ON$_5$, 461.8; m/z found 462.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.185 min at 254 nm.

Example 4. (2,3-dichloro-4-fluorophenyl)((6R,10S)-2-methyl-4-(1H-pyrazol-5-yl)-5,6,7,8,9,10-hexahydro-6,10-epiminocycloocta[d]pyrimidin-11-yl)methanone

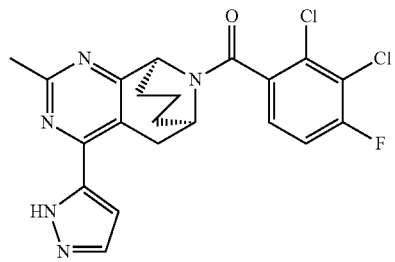 [SMILES: Cc1nc(-c2ccn[nH]2)c2c(n1)[C@@H]1CCC[C@H](C2)N1C(=O)c1ccc(F)c(Cl)c1Cl]

Example 4 was made in a manner analogous to Example 3 substituting 2,3-dichloro-4-fluorobenzoic acid for 2-chloro-3-(trifluoromethyl)benzoic acid (61 mg, 55%). MS (ESI): mass calculated for C$_{21}$H$_{18}$Cl$_2$FON$_5$, 446.3; m/z found 446.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.171 min at 254 nm.

Example 5. (2,4-dichlorophenyl)((6R,10S)-2-methyl-4-(1H-pyrazol-5-yl)-5,6,7,8,9,10-hexahydro-6,10-epiminocycloocta[d]pyrimidin-11-yl)methanone

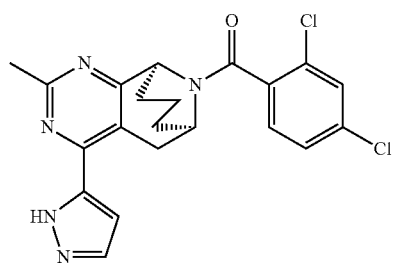 [SMILES: Cc1nc(-c2ccn[nH]2)c2c(n1)[C@@H]1CCC[C@H](C2)N1C(=O)c1ccc(Cl)cc1Cl]

Example 5 was made in a manner analogous to Example 3 substituting 2,4-dichlorobenzoic acid for 2-chloro-3-(trifluoromethyl)benzoic acid (66 mg, 62%). MS (ESI): mass calculated for $C_{21}H_{19}Cl_2ON_5$, 428.3; m/z found 428.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.109 min at 254 nm.

Example 6. (2-methyl-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone

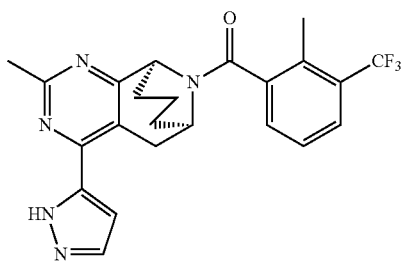

Example 6 was made in a manner analogous to Example 3 substituting 2-methyl-3-(trifluoromethyl)benzoic acid for 2-chloro-3-(trifluoromethyl)benzoic acid (59 mg, 53%). MS (ESI): mass calculated for $C_{23}H_{22}F_3ON_5$, 441.4; m/z found 442.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.222 min at 254 nm.

Example 7. (3-chloro-2-(trifluoromethyl)pyridin-4-yl)((6R,10S)-2-methyl-4-(1H-pyrazol-5-yl)-5,6,7,8,9,10-hexahydro-6,10-epiminocycloocta[d]pyrimidin-11-yl)methanone

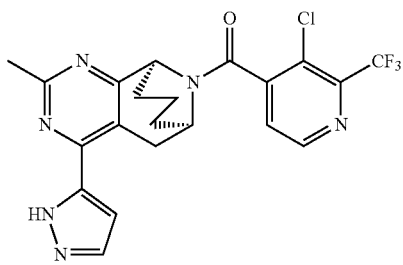 [SMILES: Cc1nc(-c2ccn[nH]2)c2c(n1)[C@@H]1CCC[C@H](C2)N1C(=O)c1cccc(C(F)(F)F)c1C]

Example 7 was made in a manner analogous to Example 3 substituting 3-chloro-2-(trifluoromethyl)isonicotinic acid for 2-chloro-3-(trifluoromethyl)benzoic acid (17 mg, 14%). MS (ESI): mass calculated for $C_{21}H_{18}ClF_3ON_6$, 462.8; m/z found 463.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.166 min at 254 nm.

Example 8. (2-fluoro-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone

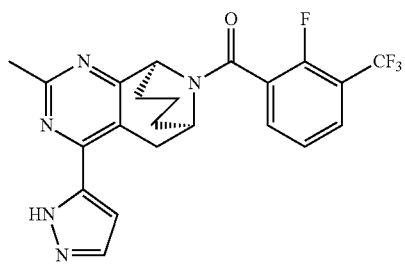 [SMILES: Cc1nc(-c2ccn[nH]2)c2c(n1)[C@@H]1CCC[C@H](C2)N1C(=O)c1cccc(C(F)(F)F)c1F]

Example 8 was made in a manner analogous to Example 3 substituting 2-fluoro-3-(trifluoromethyl)benzoic acid for 2-chloro-3-(trifluoromethyl)benzoic acid (54 mg, 49%). MS (ESI): mass calculated for $C_{22}H_{19}F_4ON_5$, 445.4; m/z found 446.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.198 min at 254 nm.

Example 9. (2-chloro-4-fluorophenyl)((6R,10S)-2-methyl-4-(1H-pyrazol-5-yl)-5,6,7,8,9,10-hexahydro-6,10-epiminocycloocta[d]pyrimidin-11-yl)methanone

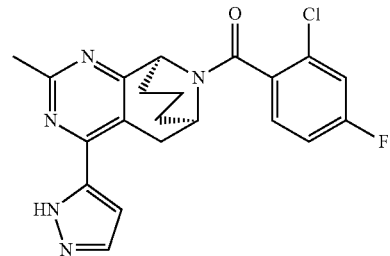 [SMILES: Cc1nc(-c2ccn[nH]2)c2c(n1)[C@@H]1CCC[C@H](C2)N1C(=O)c1ccc(F)cc1Cl]

Example 9 was made in a manner analogous to Example 3 substituting 2-chloro-4-fluorobenzoic acid for 2-chloro-3-(trifluoromethyl)benzoic acid (58 mg, 56%). MS (ESI): mass calculated for $C_{21}H_{19}ClFON_5$, 411.8; m/z found 412.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.109 min at 254 nm.

Example 10. (2,4-dichloro-3-fluorophenyl)((6R,10S)-2-methyl-4-(1H-pyrazol-5-yl)-5,6,7,8,9,10-hexahydro-6,10-epiminocycloocta[d]pyrimidin-11-yl)methanone

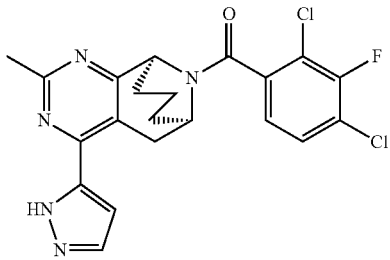 [SMILES: Cc1nc(-c2ccn[nH]2)c2c(n1)[C@@H]1CCC[C@H](C2)N1C(=O)c1ccc(Cl)c(F)c1Cl]

Example 10 was made in a manner analogous to Example 3 substituting 2,4-dichloro-3-fluorobenzoic acid for 2-chloro-3-(trifluoromethyl)benzoic acid (51 mg, 46%). MS (ESI): mass calculated for $C_{21}H_{18}Cl_2FON_5$, 446.3; m/z found 448.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.227 min at 254 nm.

Example 11. (2,3-dichlorophenyl)((6R,10S)-2-methyl-4-(1H-pyrazol-5-yl)-5,6,7,8,9,10-hexahydro-6,10-epiminocycloocta[d]pyrimidin-11-yl)methanone

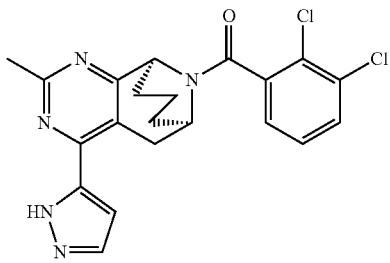 [SMILES: Cc1nc(-c2ccn[nH]2)c2c(n1)[C@@H]1CCC[C@H](C2)N1C(=O)c1cccc(Cl)c1Cl]

Example 11 was made in a manner analogous to Example 3 substituting 2,3-dichlorobenzoic acid for 2-chloro-3-(trifluoromethyl)benzoic acid (58 mg, 54%). MS (ESI): mass calculated for $C_{21}H_{19}Cl_2ON_5$, 428.3; m/z; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.170 min at 254 nm.

Example 12. (4-chloro-2-fluorophenyl)((6R,10S)-2-methyl-4-(1H-pyrazol-5-yl)-5,6,7,8,9,10-hexahydro-6,10-epiminocycloocta[d]pyrimidin-11-yl)methanone

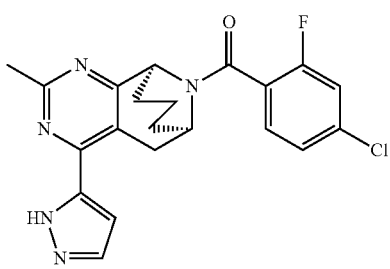

Example 12 was made in a manner analogous to Example 3 substituting 2-fluoro-4-chlorobenzoic acid for 2-chloro-3-(trifluoromethyl)benzoic acid (72 mg, 70%). MS (ESI): mass calculated for $C_{21}H_{19}ClFON_5$, 411.8; m/z found 412.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.160 min at 254 nm.

Example 13. (2-chloro-3-(trifluoromethyl)phenyl)((6R,10S)-4-(4-fluorophenyl)-2-methyl-5,6,7,8,9,10-hexahydro-6,10-epiminocycloocta[d]pyrimidin-11-yl)methanone

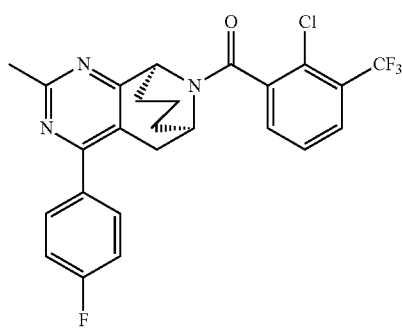 [SMILES: Cc1nc(-c2ccc(F)cc2)c2c(n1)[C@@H]1CCC[C@H](C2)N1C(=O)c1cccc(C(F)(F)F)c1Cl]

Example 13 was made in a manner analogous to Example 3 wherein (6R,10S)-4-(4-fluorophenyl)-2-methyl-5,6,7,8,9,10-hexahydro-6,10-epiminocycloocta[d]pyrimidine was used in place of (6R,10S)-2-methyl-4-(1H-pyrazol-5-yl)-5,6,7,8,9,10-hexahydro-6,10-epiminocycloocta[d]pyrimidine (47 mg, 53%). MS (ESI): mass calculated for $C_{25}H_{20}ClF_4ON_3$, 489.9; m/z found 490.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.1448 min at 254 nm.

Example 14. ((6R,10S)-4-(4-fluorophenyl)-2-methyl-5,6,7,8,9,10-hexahydro-6,10-epiminocycloocta[d]pyrimidin-11-yl)(2-methyl-3-(trifluoromethyl)phenyl)methanone

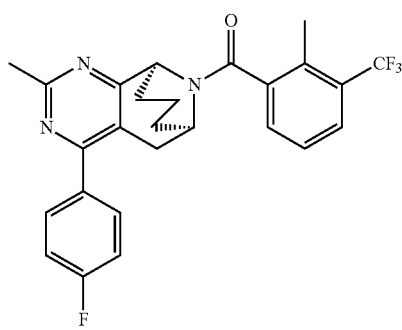 [SMILES: Cc1nc(-c2ccc(F)cc2)c2c(n1)[C@@H]1CCC[C@H](C2)N1C(=O)c1cccc(C(F)(F)F)c1C]

Example 14 was made in a manner analogous to Example 3 substituting 2-methyl-3-(trifluromethyl)benzoic acid for 2-chloro-3-(trifluoromethyl)benzoic acid (27 mg, 31%). MS (ESI): mass calculated for $C_{26}H_{23}F_4ON_3$, 469.4; m/z found 470.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.459 min at 254 nm.

Example 15. (2,4-dichlorophenyl)((6R,10S)-4-(4-fluorophenyl)-2-methyl-5,6,7,8,9,10-hexahydro-6,10-epiminocycloocta[d]pyrimidin-11-yl)methanone

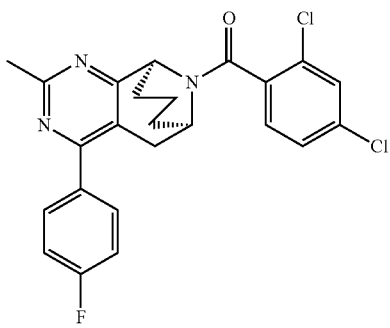 [SMILES: Cc1nc(-c2ccc(F)cc2)c2c(n1)[C@@H]1CCC[C@H](C2)N1C(=O)c1ccc(Cl)cc1Cl]

Example 15 was made in a manner analogous to Example 14 substituting 2,4-dichlorobenzoic acid for 2-chloro-3-(trifluoromethyl)benzoic acid (42 mg, 51%). MS (ESI): mass calculated for $C_{24}H_{20}Cl_2FON_3$, 456.3; m/z found 458.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.434 min at 254 nm.

Example 16. (2-chloro-4-fluorophenyl)((6R,10S)-4-(4-fluorophenyl)-2-methyl-5,6,7,8,9,10-hexahydro-6,10-epiminocycloocta[d]pyrimidin-11-yl)methanone

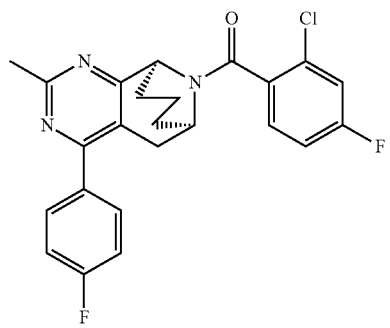 [SMILES: Cc1nc(-c2ccc(F)cc2)c2c(n1)[C@@H]1CCC[C@H](C2)N1C(=O)c1ccc(F)cc1Cl]

Example 16 was made in a manner analogous to Example 14 substituting 2-chloro-4-fluorobenzoic acid for 2-chloro-3-(trifluoromethyl)benzoic acid (28 mg, 36%). MS (ESI): mass calculated for $C_{24}H_{20}ClF_2ON_3$, 439.9; m/z found 440.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.351 min at 254 nm.

Example 17. (2,3-dichloro-4-fluorophenyl)((6R,10S)-4-(4-fluorophenyl)-2-methyl-5,6,7,8,9,10-hexahydro-6,10-epiminocycloocta[d]pyrimidin-11-yl)methanone

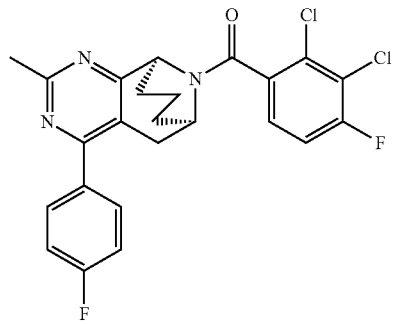 [SMILES: Cc1nc(-c2ccc(F)cc2)c2c(n1)[C@@H]1CCC[C@H](C2)N1C(=O)c1ccc(F)c(Cl)c1Cl]

Example 17 was made in a manner analogous to Example 14 substituting 2,4-dichloro-3-fluorobenzoic acid for 2-chloro-3-(trifluoromethyl)benzoic acid (36 mg, 42%). MS (ESI): mass calculated for $C_{24}H_{19}Cl_2F_2ON_3$, 474.3; m/z found 474.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.443 min at 254 nm.

Example 18. (3-chloro-2-(trifluoromethyl)pyridin-4-yl)((6R,10S)-4-(4-fluorophenyl)-2-methyl-5,6,7,8,9,10-hexahydro-6,10-epiminocycloocta[d]pyrimidin-11-yl)methanone

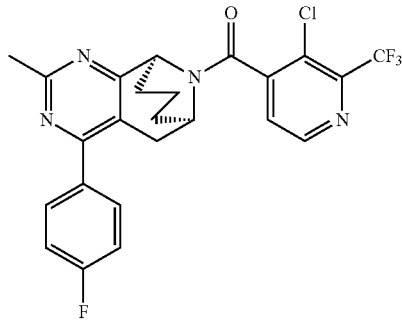 [SMILES: Cc1nc(-c2ccc(F)cc2)c2c(n1)[C@@H]1CCC[C@H](C2)N1C(=O)c1ccnc(C(F)(F)F)c1Cl]

Example 18 was made in a manner analogous to Example 14 substituting 3-chloro-2-(trifluoromethyl)isonicotinic acid for 2-chloro-3-(trifluoromethyl)benzoic acid (37 mg, 42%). MS (ESI): mass calculated for $C_{24}H_{19}ClF_4ON_4$, 490.8; m/z found 491.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.359 min at 254 nm.

Example 19. (2-chloro-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone

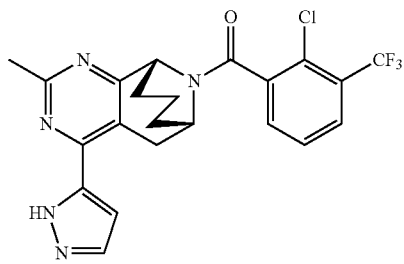 [SMILES: Cc1nc(-c2ccn[nH]2)c2c(n1)[C@H]1CCC[C@@H](C2)N1C(=O)c1cccc(C(F)(F)F)c1Cl]

Example 19 was made in a manner analogous to Example 3 where in (6S,10R)-2-methyl-4-(1H-pyrazol-5-yl)-5, 6,7,8,9,10-hexahydro-6,10-epiminocycloocta[d]pyrimidine was used in place of (6R,10S)-2-methyl-4-(1H-pyrazol-5-yl)-5,6,7,8,9,10-hexahydro-6,10-epiminocycloocta[d]pyrimidine (11 mg, 8.6%). MS (ESI): mass calculated for $C_{22}H_{19}ClF_3ON_5$, 461.8; m/z found 462.1 [M+H]$^+$; Analytical HPLC was obtained on a Agilent 1100 Series LCMS, using an Inertsil ODS-3 column (3 μM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_t$=1.150 min at 254 nm.

Example 20. (2,4-dichlorophenyl)((6S,10R)-2-methyl-4-(1H-pyrazol-5-yl)-5,6,7,8,9,10-hexahydro-6,10-epiminocycloocta[d]pyrimidin-11-yl)methanone

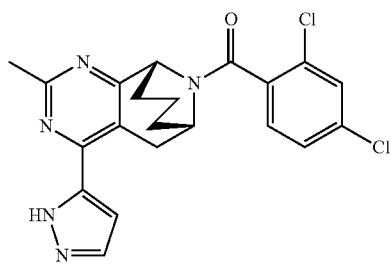 [SMILES: Cc1nc(-c2ccn[nH]2)c2c(n1)[C@H]1CCC[C@@H](C2)N1C(=O)c1ccc(Cl)cc1Cl]

Example 20 was made in a manner analogous to Example 19 substituting 2,4-dichlorobenzoic acid for 2-chloro-3-(trifluoromethyl)benzoic acid (33 mg, 27%). MS (ESI): mass calculated for $C_{21}H_{19}Cl_2ON_5$, 428.3; m/z found 428.1 [M+H]$^+$; Analytical HPLC was obtained on a Agilent 1100 Series LCMS, using an Inertsil ODS-3 column (3 μM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_t$=1.138 min at 254 nm.

Example 21. (2-methyl-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone

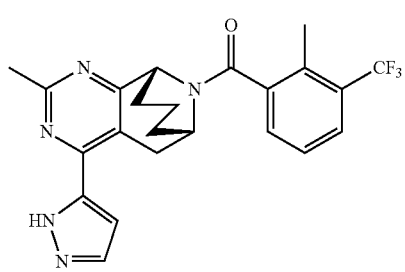 [SMILES: Cc1nc(-c2ccn[nH]2)c2c(n1)[C@H]1CCC[C@@H](C2)N1C(=O)c1cccc(C(F)(F)F)c1C]

Example 21 was made in a manner analogous to Example 19 substituting 2-methyl-3-(trifluoromethyl)benzoic acid for 2-chloro-3-(trifluoromethyl)benzoic acid (25 mg, 20%). MS (ESI): mass calculated for $C_{23}H_{22}F_3ON_5$, 441.4; m/z found 442.2 [M+H]$^+$; Analytical HPLC was obtained on a Agilent 1100 Series LCMS, using an Inertsil ODS-3 column (3 μM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_t$=1.158 min at 254 nm.

Example 22. (2-chloro-4-fluorophenyl)((6S,10R)-2-methyl-4-(1H-pyrazol-5-yl)-5,6,7,8,9,10-hexahydro-6,10-epiminocycloocta[d]pyrimidin-11-yl)methanone

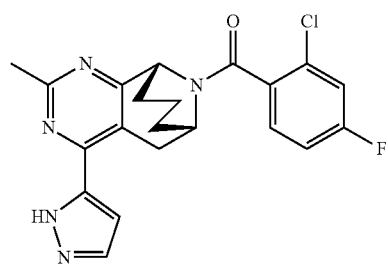 [SMILES: Cc1nc(-c2ccn[nH]2)c2c(n1)[C@H]1CCC[C@@H](C2)N1C(=O)c1ccc(F)cc1Cl]

Example 22 was made in a manner analogous to Example 19 substituting 2-chloro-4-fluorobenzoic acid for 2-chloro-3-(trifluoromethyl)benzoic acid (32 mg, 27%). MS (ESI): mass calculated for $C_{21}H_{19}FClON_5$, 411.8; m/z found 412.1 [M+H]$^+$; Analytical HPLC was obtained on a Agilent 1100 Series LCMS, using an Inertsil ODS-3 column (3 μM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_t$=1.054 min at 254 nm.

Example 23. (2,4-dichloro-3-fluorophenyl)((6S,10R)-2-methyl-4-(1H-pyrazol-5-yl)-5,6,7,8,9,10-hexahydro-6,10-epiminocycloocta[d]pyrimidin-11-yl)methanone

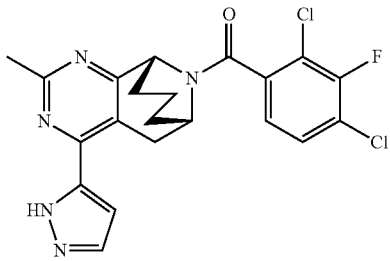 [SMILES: Cc1nc(-c2ccn[nH]2)c2c(n1)[C@H]1CCC[C@@H](C2)N1C(=O)c1ccc(Cl)c(F)c1Cl]

Example 23 was made in a manner analogous to Example 19 substituting 2,4-dichloro-3-fluorobenzoic acid for 2-chloro-3-(trifluoromethyl)benzoic acid (33 mg, 27%). MS (ESI): mass calculated for $C_{21}H_{18}FCl_2ON_5$, 446.3; m/z found 446.1 [M+H]$^+$; Analytical HPLC was obtained on a Agilent 1100 Series LCMS, using an Inertsil ODS-3 column (3 µM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_t$=1.164 min at 254 nm.

Example 24. (3-chloro-2-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone

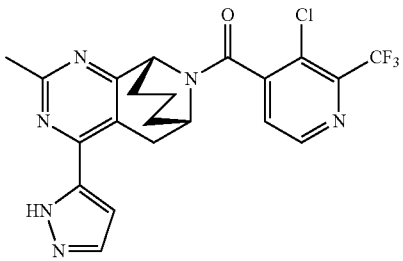 [SMILES: Cc1nc(-c2ccn[nH]2)c2c(n1)[C@H]1CCC[C@@H](C2)N1C(=O)c1ccnc(C(F)(F)F)c1Cl]

Example 24 was made in a manner analogous to Example 19 substituting 3-chloro-2-(trifluoromethyl)isonicotinic acid for 2-chloro-3-(trifluoromethyl)benzoic acid (25 mg, 19%). MS (ESI): mass calculated for $C_{21}H_{18}ClF_3ON_6$, 462.8; m/z found 463.1 [M+H]$^+$; Analytical HPLC was obtained on a Agilent 1100 Series LCMS, using an Inertsil ODS-3 column (3 µM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_t$=1.102 min at 254 nm.

Example 25. (2,3-dichloro-4-fluorophenyl)((6S,10R)-2-methyl-4-(1H-pyrazol-5-yl)-5,6,7,8,9,10-hexahydro-6,10-epiminocycloocta[d]pyrimidin-11-yl)methanone

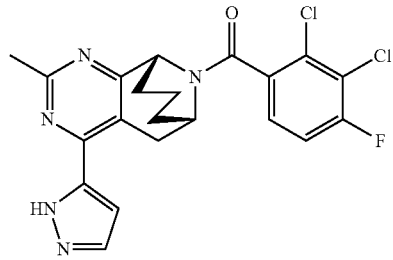 [SMILES: Cc1nc(-c2ccn[nH]2)c2c(n1)[C@H]1CCC[C@@H](C2)N1C(=O)c1ccc(F)c(Cl)c1Cl]

Example 25 was made in a manner analogous to Example 19 substituting 2,3-dichloro-4-fluorobenzoic acid for 2-chloro-3-(trifluoromethyl)benzoic acid (27 mg, 21%). MS (ESI): mass calculated for $C_{21}H_{18}Cl_2FON_5$, 446.3; m/z found 446.1 [M+H]$^+$; Analytical HPLC was obtained on a Agilent 1100 Series LCMS, using an Inertsil ODS-3 column (3 µM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_t$=1.144 min at 254 nm.

Example 26. (2-fluoro-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone

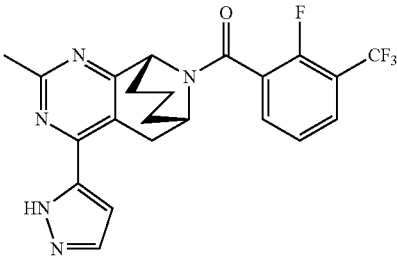 [SMILES: Cc1nc(-c2ccn[nH]2)c2c(n1)[C@H]1CCC[C@@H](C2)N1C(=O)c1cccc(C(F)(F)F)c1F]

Example 26 was made in a manner analogous to Example 19 substituting 2-fluoro-3-(trifluoromethyl)benzoic acid for 2-chloro-3-(trifluoromethyl)benzoic acid (30 mg, 24%). MS (ESI): mass calculated for $C_{22}H_{19}F_4ON_5$, 445.4; m/z found 446.1 [M+H]$^+$; Analytical HPLC was obtained on a Agilent 1100 Series LCMS, using an Inertsil ODS-3 column (3 µM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_t$=1.138 min at 254 nm.

Example 27. (3-fluoro-2-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone

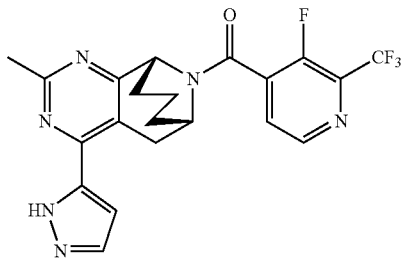

Example 27 was made in a manner analogous to Example 19 substituting 3-fluoro-2-(trifluoromethyl)isonicotinc acid for 2-chloro-3-(trifluoromethyl)benzoic acid (18 mg, 14%). MS (ESI): mass calculated for $C_{21}H_{18}F_4ON_6$, 446.4; m/z found 447.2 $[M+H]^+$; Analytical HPLC was obtained on a Agilent 1100 Series LCMS, using an Inertsil ODS-3 column (3 μM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_f$=1.088 min at 254 nm.

Example 28. (4-chloro-2-fluorophenyl)((6S,10R)-2-methyl-4-(1H-pyrazol-5-yl)-5,6,7,8,9,10-hexahydro-6,10-epiminocycloocta[d]pyrimidin-11-yl)methanone

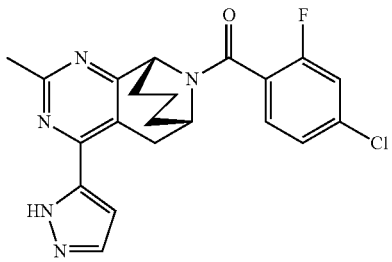

Example 28 was made in a manner analogous to Example 19 substituting 4-chloro-2-fluorobenzoic acid for 2-chloro-3-(trifluoromethyl)benzoic acid (35 mg, 30%). MS (ESI): mass calculated for $C_{21}H_{19}ClFON_5$, 411.8; m/z found 412.1 $[M+H]^+$; Analytical HPLC was obtained on a Agilent 1100 Series LCMS, using an Inertsil ODS-3 column (3 μM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_f$=1.102 min at 254 nm.

Example 29. (2,3-dichlorophenyl)((6S,10R)-2-methyl-4-(1H-pyrazol-5-yl)-5,6,7,8,9,10-hexahydro-6,10-epiminocycloocta[d]pyrimidin-11-yl)methanone

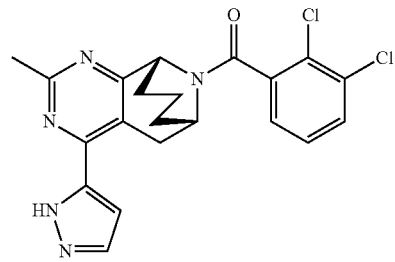 [SMILES: Cc1nc(-c2ccn[nH]2)c2c(n1)[C@H]1CCC[C@@H](C2)N1C(=O)c1cccc(Cl)c1Cl]

Example 29 was made in a manner analogous to Example 19 substituting 2,4-dichlorobenzoic acid for 2-chloro-3-(trifluoromethyl)benzoic acid (21 mg, 17%). MS (ESI): mass calculated for $C_{21}H_{19}Cl_2ON_5$, 428.3; m/z found 430.1 $[M+H]^+$; Analytical HPLC was obtained on a Agilent 1100 Series LCMS, using an Inertsil ODS-3 column (3 μM, 50×3 mM), mobile phase of 5-100% ACN in 0.05% TFA over 1.5 min and then hold at 100% ACN for 0.5 min, at a flow rate of 2.5 mL/min (Temperature=50° C.). An Agilent G1956B ESI-SQD was used for mass detection in positive mode with a scan range of 110-750 amu. $R_f$=1.112 min at 254 nm.

Example 30. (2-chloro-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone

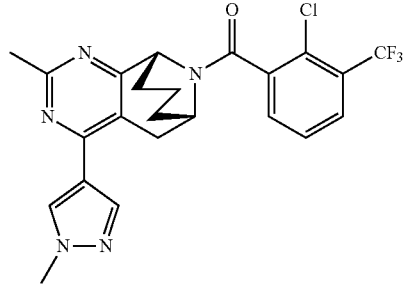 [SMILES: Cc1nc(-c2cnn(C)c2)c2c(n1)[C@H]1CCC[C@@H](C2)N1C(=O)c1cccc(C(F)(F)F)c1Cl]

Example 23 was made in a manner analogous to Example 3 where in (6S,10R)-2-methyl-4-(1-methyl-1H-pyrazol-4-yl)-5,6,7,8,9,10-hexahydro-6,10-epiminocycloocta[d]pyrimidine was used in place of (6R,10S)-2-methyl-4-(1H-pyrazol-5-yl)-5,6,7,8,9,10-hexahydro-6,10-epiminocycloocta[d]pyrimidine (63 mg, 54%). MS (ESI): mass calculated for $C_{23}H_{21}ClF_3ON_5$, 475.9; m/z found 476.1 $[M+H]^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_f$=1.137 min at 254 nm.

Example 31. (2,3-dichlorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone

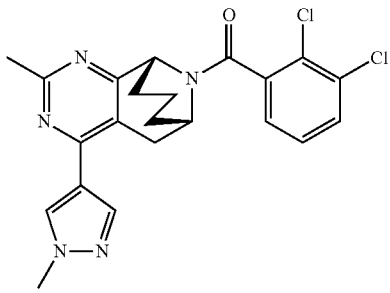 [SMILES: Cc1nc(-c2cnn(C)c2)c2c(n1)[C@H]1CCC[C@@H](C2)N1C(=O)c1cccc(Cl)c1Cl]

Example 31 was made in a manner analogous to Example 30 substituting 2,4-dichlorobenzoic acid for 2-chloro-3-(trifluoromethyl)benzoic acid (65 mg, 60%). MS (ESI): mass calculated for $C_{22}H_{21}Cl_2ON_5$, 442.3; m/z found 443.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.121 min at 254 nm.

Example 32. (3-chloro-2-(trifluoromethyl)pyridin-4-yl)((6S,10R)-2-methyl-4-(1-methyl-1H-pyrazol-4-yl)-5,6,7,8,9,10-hexahydro-6,10-epiminocycloocta[d]pyrimidin-11-yl)methanone

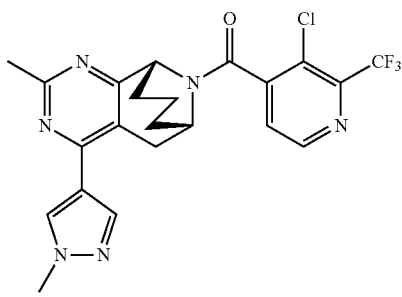

Example 32 was made in a manner analogous to Example 30 substituting 3-chloro-2-(trifluoromethyl)isonicotinic acid for 2-chloro-3-(trifluoromethyl)benzoic acid (68 mg, 58%). MS (ESI): mass calculated for $C_{22}H_{20}ClF_3ON_6$, 476.8; m/z found 477.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.126 min at 254 nm.

Example 33. (2,3-dichloro-4-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone

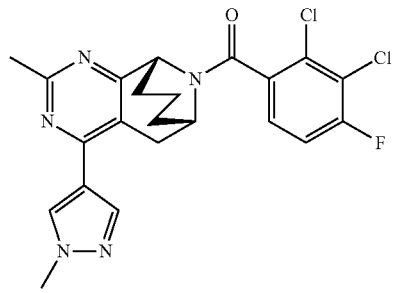 [SMILES: Cc1nc(-c2cnn(C)c2)c2c(n1)[C@H]1CCC[C@@H](C2)N1C(=O)c1ccc(F)c(Cl)c1Cl]

Example 33 was made in a manner analogous to Example 30 substituting 2,3-dichloro-4-fluorobenzoic acid for 2-chloro-3-(trifluoromethyl)benzoic acid (84 mg, 74%). MS (ESI): mass calculated for $C_{22}H_{20}Cl_2FON_5$, 460.3; m/z found 461.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.179 min at 254 nm.

Example 34. (2-fluoro-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone

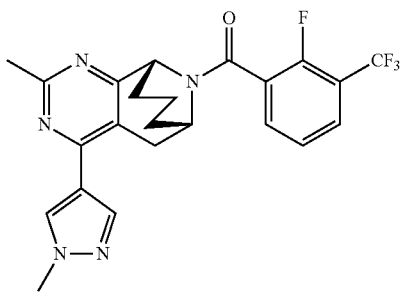

Example 34 was made in a manner analogous to Example 30 substituting 2-fluoro-3-(trifluoromethyl)benzoic acid for 2-chloro-3-(trifluoromethyl)benzoic acid (102 mg, 91%). MS (ESI): mass calculated for $C_{23}H_{21}F_4ON_5$, 459.4; m/z found 460.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.173 min at 254 nm.

Example 35. (2,4-dichloro-3-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone

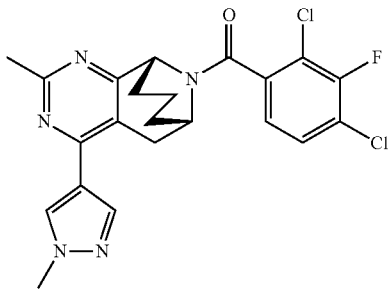 [SMILES: Cc1nc(-c2cnn(C)c2)c2c(n1)[C@H]1CCC[C@@H](C2)N1C(=O)c1ccc(Cl)c(F)c1Cl]

Example 35 was made in a manner analogous to Example 30 substituting 2,4-dichloro-3-fluorobenzoic acid for 2-chloro-3-(trifluoromethyl)benzoic acid (89 mg, 79%). MS (ESI): mass calculated for $C_{22}H_{20}Cl_2FON_5$, 460.3; m/z found 461.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.201 min at 254 nm.

Example 36. (2-chloro-4-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone

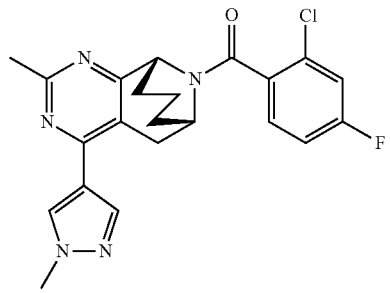 [SMILES: Cc1nc(-c2cnn(C)c2)c2c(n1)[C@H]1CCC[C@@H](C2)N1C(=O)c1ccc(F)cc1Cl]

Example 36 was made in a manner analogous to Example 30 substituting 2-chloro-4-fluorobenzoic acid for 2-chloro-3-(trifluoromethyl)benzoic acid (79 mg, 76%). MS (ESI): mass calculated for $C_{22}H_{21}ClFON_5$, 425.9; m/z found 426.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.083 min at 254 nm.

Example 37. (3-fluoro-2-(trifluoromethyl)pyridin-4-yl)((6S,10R)-2-methyl-4-(1-methyl-1H-pyrazol-4-yl)-5,6,7,8,9,10-hexahydro-6,10-epiminocycloocta[d]pyrimidin-11-yl)methanone

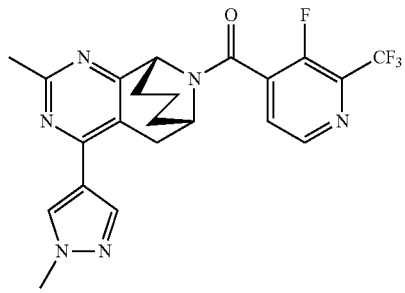

Example 37 was made in a manner analogous to Example 30 substituting 3-fluoro-2-(trifluoromethyl)isonicotinic acid for 2-chloro-3-(trifluoromethyl)benzoic acid (73 mg, 65%). MS (ESI): mass calculated for $C_{22}H_{20}F_4ON_6$, 460.4; m/z found 461.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.130 min at 254 nm.

Example 38. (4-chloro-2-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone

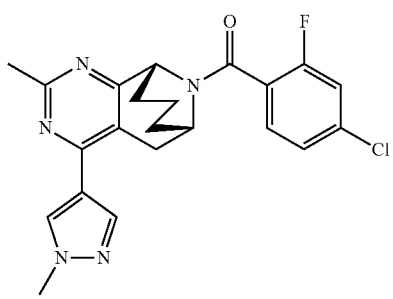 [SMILES: Cc1nc(-c2cnn(C)c2)c2c(n1)[C@H]1CCC[C@@H](C2)N1C(=O)c1ccc(Cl)cc1F]

Example 38 was made in a manner analogous to Example 30 substituting 4-chloro-2-fluorobenzoic acid for 2-chloro-3-(trifluoromethyl)benzoic acid (84 mg, 81%). MS (ESI): mass calculated for $C_{22}H_{21}ClFON_5$, 425.8; m/z found 426.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.2 mL/min (Temperature=50° C.). $R_t$=1.198 min at 254 nm.

Example 39. (2-methyl-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone

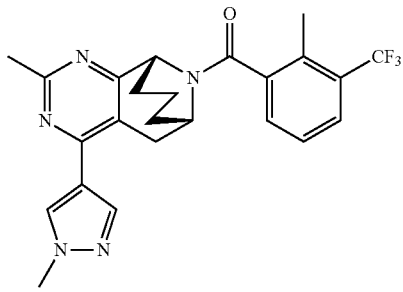

Example 39 was made in a manner analogous to Example 30 substituting 2-methyl-3-(trifluoromethyl)benzoic acid for 2-chloro-3-(trifluoromethyl)benzoic acid (83 mg, 74%). MS (ESI): mass calculated for $C_{24}H_{24}F_3ON_5$, 455.4; m/z found 456.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.2 mL/min (Temperature=50° C.). R$_t$=1.1257 min at 254 nm.

Example 40. (2,4-dichlorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone

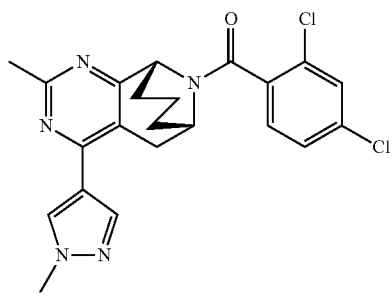 [SMILES: Cc1nc(-c2cnn(C)c2)c2c(n1)[C@H]1CCC[C@@H](C2)N1C(=O)c1ccc(Cl)cc1Cl]

Example 40 was made in a manner analogous to Example 30 substituting 2,4-dichlorobenzoic acid for 2-chloro-3-(trifluoromethyl)benzoic acid (73 mg, 67%). MS (ESI): mass calculated for $C_{22}H_{21}Cl_2ON_5$, 442.3; m/z found 442.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.2 mL/min (Temperature=50° C.). R$_t$=1.236 min at 254 nm.

Example 41. (2-chloro-3-(trifluoromethyl)phenyl)((6S,10R)-2-methyl-4-(pyrimidin-2-yl)-5,6,7,8,9,10-hexahydro-6,10-epiminocycloocta[d]pyrimidin-11-yl)methanone

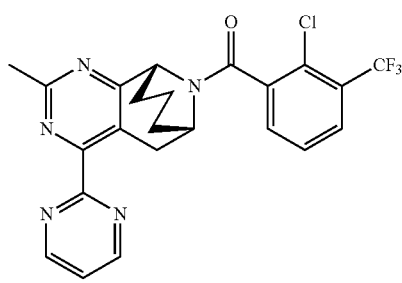

Example 41 was made in a manner analogous to Example 3 wherein (6S,10R)-2-methyl-4-(pyrimidin-2-yl)-5,6,7,8,9,10-hexahydro-6,10-epiminocycloocta[d]pyrimidine was used in place of (6R,10S)-2-methyl-4-(1H-pyrazol-5-yl)-5,6,7,8,9,10-hexahydro-6,10-epiminocycloocta[d]pyrimidine (66 mg, 77%). MS (ESI): mass calculated for $C_{23}H_{19}ClF_3ON_5$, 473.8; m/z found 473.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.183 min at 254 nm.

Example 42. (3-chloro-2-(trifluoromethyl)pyridin-4-yl)((6S,10R)-2-methyl-4-(pyrimidin-2-yl)-5,6,7,8,9,10-hexahydro-6,10-epiminocycloocta[d]pyrimidin-11-yl)methanone

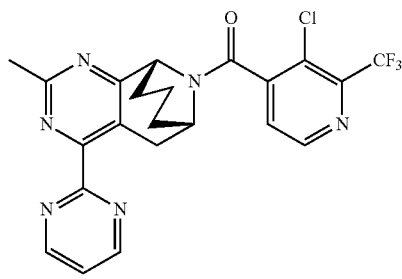 [SMILES: Cc1nc(-c2ncccn2)c2c(n1)[C@H]1CCC[C@@H](C2)N1C(=O)c1ccnc(C(F)(F)F)c1Cl]

Example 23 was made in a manner analogous to Example 41 substituting 3-chloro-2-(trifluoromethyl)isonicotinic acid for 2-chloro-3-(trifluoromethyl)benzoic acid (58 mg, 68%). MS (ESI): mass calculated for $C_{22}H_{18}ClF_3ON_6$, 474.8; m/z found 475.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.123 min at 254 nm.

Example 43. (2-methyl-3-(trifluoromethyl)phenyl)((6S,10R)-2-methyl-4-(pyrimidin-2-yl)-5,6,7,8,9,10-hexahydro-6,10-epiminocycloocta[d]pyrimidin-11-yl)methanone

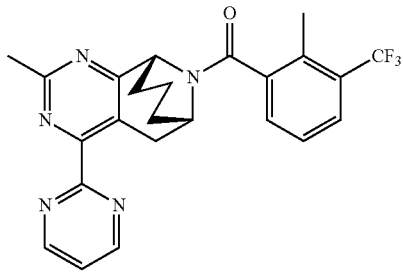

Example 43 was made in a manner analogous to Example 41 substituting 2-methyl-3-(trifluoromethyl)benzoic acid for 2-chloro-3-(trifluoromethyl)benzoic acid (65 mg, 80%). MS (ESI): mass calculated for $C_{24}H_{22}F_3ON_5$, 453.4; m/z found 454.2 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.2 mL/min (Temperature=50° C.). $R_t$=1.254 min at 254 nm.

Example 44. (2,4-dichloro-3-fluorophenyl)((6S,10R)-2-methyl-4-(pyrimidin-2-yl)-5,6,7,8,9,10-hexahydro-6,10-epiminocycloocta[d]pyrimidin-11-yl)methanone

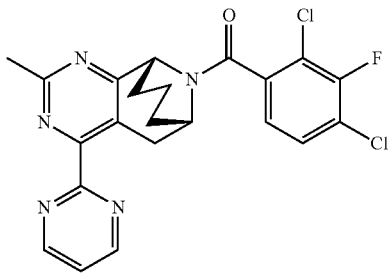

Example 44 was made in a manner analogous to Example 41 substituting 2,4-dichloro-3-fluorobenzoic acid for 2-chloro-3-(trifluoromethyl)benzoic acid (75 mg, 91%). MS (ESI): mass calculated for $C_{22}H_{18}Cl_2FON_5$, 458.3; m/z found 459.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.206 min at 254 nm.

Example 45. (2,3-dichlorophenyl)((6S,10R)-2-methyl-4-(pyrimidin-2-yl)-5,6,7,8,9,10-hexahydro-6,10-epiminocycloocta[d]pyrimidin-11-yl)methanone

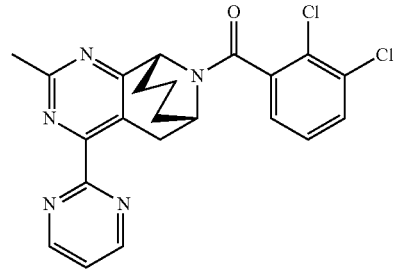 [SMILES: Cc1nc(-c2ncccn2)c2c(n1)[C@H]1CCC[C@@H](C2)N1C(=O)c1cccc(Cl)c1Cl]

Example 45 was made in a manner analogous to Example 41 substituting 2,3-dichlorobenzoic acid for 2-chloro-3-(trifluoromethyl)benzoic acid (44 mg, 56%). MS (ESI): mass calculated for $C_{22}H_{19}Cl_2ON_5$, 440.3; m/z found 440.1 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.153 min at 254 nm.

Example 46. (2-chloro-3-(trifluoromethyl)phenyl)((6S,10R)-2-methyl-4-(pyrazin-2-yl)-5,6,7,8,9,10-hexahydro-6,10-epiminocycloocta[d]pyrimidin-11-yl)methanone

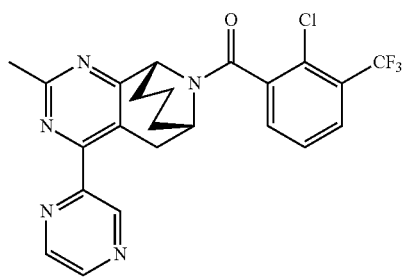 [SMILES: Cc1nc(-c2cnccn2)c2c(n1)[C@H]1CCC[C@@H](C2)N1C(=O)c1cccc(C(F)(F)F)c1Cl]

Example 46 was made in a manner analogous to Example 3 where in (6S,10R)-2-methyl-4-(pyrazin-2-yl)-5,6,7,8,9,10-hexahydro-6,10-epiminocycloocta[d]pyrimidine was used in place of (6R,10S)-2-methyl-4-(1H-pyrazol-5-yl)-5,6,7,8,9,10-hexahydro-6,10-epiminocycloocta[d]pyrimidine (52 mg, 68%). MS (ESI): mass calculated for $C_{23}H_{19}ClF_3ON_5$, 473.8; m/z found 473.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.292 min at 254 nm.

Example 47. (2,4-dichloro-3-fluorophenyl)((6S,10R)-2-methyl-4-(pyrazin-2-yl)-5,6,7,8,9,10-hexahydro-6,10-epiminocycloocta[d]pyrimidin-11-yl)methanone

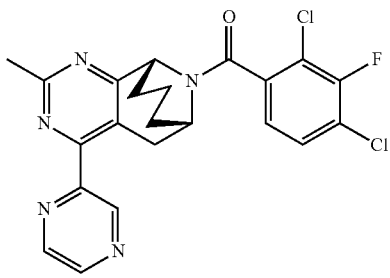 [SMILES: Cc1nc(-c2cnccn2)c2c(n1)[C@H]1CCC[C@@H](C2)N1C(=O)c1ccc(Cl)c(F)c1Cl]

Example 47 was made in a manner analogous to Example 46 substituting 2,4-dichloro-3-fluorobenzoic acid for 2-chloro-3-(trifluoromethyl)benzoic acid (73 mg, 99%). MS (ESI): mass calculated for $C_{22}H_{18}Cl_2FON_5$, 458.3; m/z found 457.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.348 min at 254 nm.

Example 48. (2,3-dichlorophenyl)((6S,10R)-2-methyl-4-(pyrazin-2-yl)-5,6,7,8,9,10-hexahydro-6,10-epiminocycloocta[d]pyrimidin-11-yl)methanone

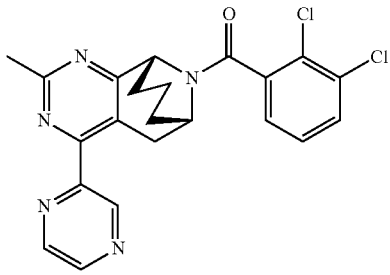 [SMILES: Cc1nc(-c2cnccn2)c2c(n1)[C@H]1CCC[C@@H](C2)N1C(=O)c1cccc(Cl)c1Cl]

Example 48 was made in a manner analogous to Example 46 substituting 2,3-dichlorobenzoic acid for 2-chloro-3-(trifluoromethyl)benzoic acid (70 mg, 98%). MS (ESI): mass calculated for $C_{22}H_{19}Cl_2ON_5$, 440.3; m/z found 439.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.292 min at 254 nm.

Example 49. (3-chloro-2-(trifluoromethyl)pyridin-4-yl)((6S,10R)-2-methyl-4-(pyrazin-2-yl)-5,6,7,8,9,10-hexahydro-6,10-epiminocycloocta[d]pyrimidin-11-yl)methanone

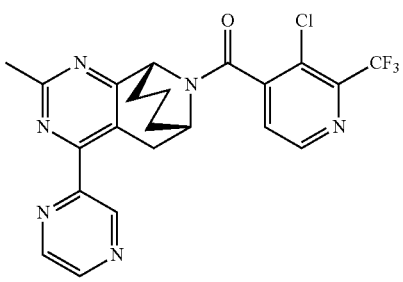

Example 49 was made in a manner analogous to Example 46 substituting 3-chloro-2-(trifluoromethyl)isonicotinic acid for 2-chloro-3-(trifluoromethyl)benzoic acid (73 mg, 95%). MS (ESI): mass calculated for $C_{22}H_{18}ClF_3ON_6$, 474.8; m/z found 475.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.226 min at 254 nm.

Example 50. (2-methyl-3-(trifluoromethyl)phenyl)((6S,10R)-2-methyl-4-(pyrazin-2-yl)-5,6,7,8,9,10-hexahydro-6,10-epiminocycloocta[d]pyrimidin-11-yl)methanone

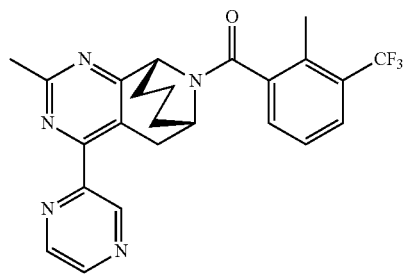 [SMILES: Cc1nc(-c2cnccn2)c2c(n1)[C@H]1CCC[C@@H](C2)N1C(=O)c1cccc(C(F)(F)F)c1C]

Example 50 was made in a manner analogous to Example 46 substituting 2-methyl-3-(trifluoromethyl)benzoic acid for 2-chloro-3-(trifluoromethyl)benzoic acid (85 mg, 73%). MS (ESI): mass calculated for $C_{24}H_{22}F_3ON_5$, 453.4; m/z found 454.0 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.319 min at 254 nm.

Example 51. (2-chloro-3-(trifluoromethyl)phenyl)((6S,10R)-4-(4-fluorophenyl)-2-methyl-5,6,7,8,9,10-hexahydro-6,10-epiminocycloocta[d]pyrimidin-11-yl)methanone

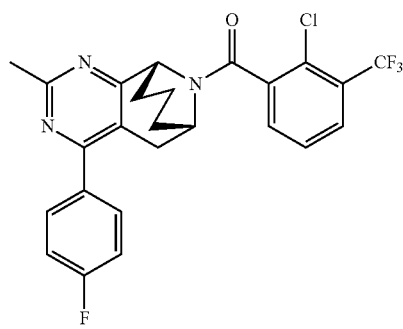 [SMILES: Cc1nc(-c2ccc(F)cc2)c2c(n1)[C@H]1CCC[C@@H](C2)N1C(=O)c1cccc(C(F)(F)F)c1Cl]

Example 51 was made in a manner analogous to that described for Example 3 where in (6S,10R)-4-(4-fluorophenyl)-2-methyl-5,6,7,8,9,10-hexahydro-6,10-epiminocycloocta[d]pyrimidine was used in place of (6R,10S)-2-methyl-4-(1H-pyrazol-5-yl)-5,6,7,8,9,10-hexahydro-6,10-epiminocycloocta[d]pyrimidine (23 mg, 47%). MS (ESI):

mass calculated for $C_{25}H_{20}ClF_4ON_3$, 489.9; m/z found 489.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.433 min at 254 nm.

Example 52. (3-chloro-2-(trifluoromethyl)pyridin-4-yl)((6S,10R)-4-(4-fluorophenyl)-2-methyl-5,6,7,8,9,10-hexahydro-6,10-epiminocycloocta[d]pyrimidin-11-yl)methanone

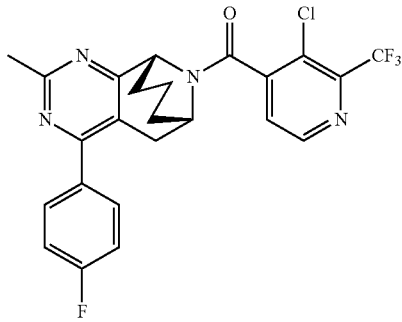

Example 52 was made in a manner analogous to Example 51 substituting 3-chloro-2-(trifluoromethyl)isonicotinic acid for 2-chloro-3-(trifluoromethyl)benzoic acid (17 mg, 35%). MS (ESI): mass calculated for $C_{24}H_{19}ClF_4ON_4$, 490.9; m/z found 489.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.382 min at 254 nm.

Example 53. ((6S,10R)-4-(4-fluorophenyl)-2-methyl-5,6,7,8,9,10-hexahydro-6,10-epiminocycloocta[d]pyrimidin-11-yl)(2-methyl-3-(trifluoromethyl)phenyl)methanone

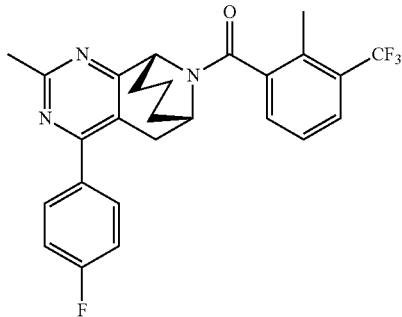 [SMILES: Cc1nc(-c2ccc(F)cc2)c2c(n1)[C@H]1CCC[C@@H](C2)N1C(=O)c1cccc(C(F)(F)F)c1C]

Example 53 was made in a manner analogous to Example 51 substituting 2-methyl-3-(trifluoromethyl)benzoic acid for 2-chloro-3-(trifluoromethyl)benzoic acid (22 mg, 47%). MS (ESI): mass calculated for $C_{26}H_{23}F_4ON_3$, 469.4; m/z found 470.0 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.455 min at 254 nm.

Example 54. (2,4-dichloro-3-fluorophenyl)((6S,10R)-4-(4-fluorophenyl)-2-methyl-5,6,7,8,9,10-hexahydro-6,10-epiminocycloocta[d]pyrimidin-11-yl)methanone

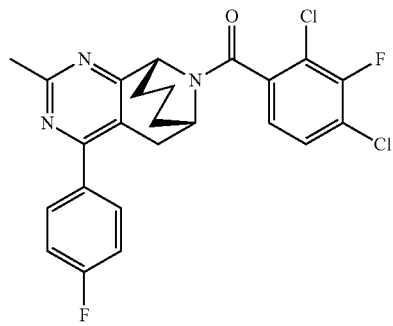 [SMILES: Cc1nc(-c2ccc(F)cc2)c2c(n1)[C@H]1CCC[C@@H](C2)N1C(=O)c1ccc(Cl)c(F)c1Cl]

Example 54 was made in a manner analogous to Example 51 substituting 2,4-dichloro-3-fluorobenzoic acid for 2-chloro-3-(trifluoromethyl)benzoic acid (19 mg, 41%). MS (ESI): mass calculated for $C_{24}H_{19}Cl_2F_2ON_3$, 474.3; m/z found 473.8 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.477 min at 254 nm.

Example 55. (2,3-dichlorophenyl)((6S,10R)-4-(4-fluorophenyl)-2-methyl-5,6,7,8,9,10-hexahydro-6,10-epiminocycloocta[d]pyrimidin-11-yl)methanone

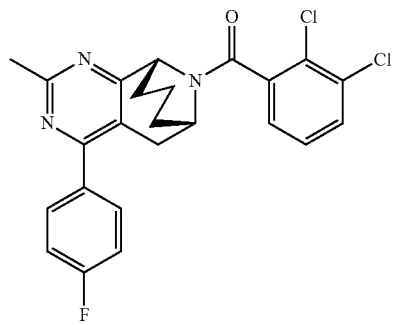 [SMILES: Cc1nc(-c2ccc(F)cc2)c2c(n1)[C@H]1CCC[C@@H](C2)N1C(=O)c1cccc(Cl)c1Cl]

Example 55 was made in a manner analogous to Example 51 substituting 2,3-dichlorobenzoic acid for 2-chloro-3-(trifluoromethyl)benzoic acid (24 mg, 54%). MS (ESI): mass calculated for $C_{24}H_{20}Cl_2FON_3$, 456.3; m/z found 457.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). R$_t$=1.429 min at 254 nm.

Example 56. (2-chloro-3-(trifluoromethyl)phenyl) ((6S,10R)-2-methyl-4-(1-methyl-1H-pyrazol-5-yl)-5, 6,7,8,9,10-hexahydro-6,10-epiminocycloocta[d]pyrimidin-11-yl)methanone

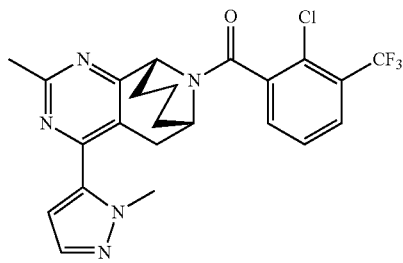 [SMILES: Cc1nc(-c2ccnn2C)c2c(n1)[C@H]1CCC[C@@H](C2)N1C(=O)c1cccc(C(F)(F)F)c1Cl]

Example 56 was made in a manner analogous to Example 3 where in (6S,10R)-2-methyl-4-(1-methyl-1H-pyrazol-5-yl)-5,6,7,8,9,10-hexahydro-6,10-epiminocycloocta[d]pyrimidine was used in place of (6R,10S)-2-methyl-4-(1H-pyrazol-5-yl)-5,6,7,8,9,10-hexahydro-6,10-epiminocycloocta[d]pyrimidine (9.2 mg, 17%). MS (ESI): mass calculated for $C_{23}H_{21}ClF_3ON_5$, 475.9; m/z found 475.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.284 min at 254 nm.

Example 57. (2-methyl-3-(trifluoromethyl)phenyl) ((6S,10R)-2-methyl-4-(1-methyl-1H-pyrazol-5-yl)-5, 6,7,8,9,10-hexahydro-6,10-epiminocycloocta[d]pyrimidin-11-yl)methanone

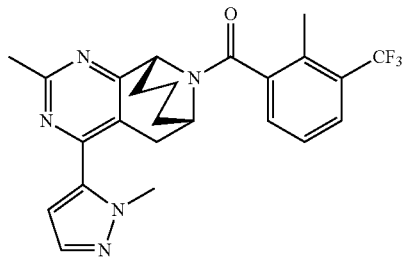

Example 57 was made in a manner analogous to Example 56 substituting 2-methyl-3-(trifluoromethyl)benzoic acid for 2-chloro-3-(trifluoromethyl)benzoic acid (23 mg, 46%). MS (ESI): mass calculated for $C_{24}H_{24}F_3ON_5$, 455.5; m/z found 456.0 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.303 min at 254 nm.

Example 58. (2,4-dichloro-3-fluorophenyl)((6S, 10R)-2-methyl-4-(1-methyl-1H-pyrazol-5-yl)-5,6,7, 8,9,10-hexahydro-6,10-epiminocycloocta[d]pyrimidin-11-yl)methanone

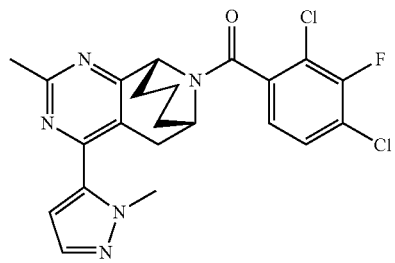 [SMILES: Cc1nc(-c2ccnn2C)c2c(n1)[C@H]1CCC[C@@H](C2)N1C(=O)c1ccc(Cl)c(F)c1Cl]

Example 58 was made in a manner analogous to Example 56 substituting 2,4-dichloro-3-fluorobenzoic acid for 2-chloro-3-(trifluoromethyl)benzoic acid (20 mg, 39%). MS (ESI): mass calculated for $C_{22}H_{20}Cl_2FON_5$, 460.3; m/z found 461.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.2 mL/min (Temperature=50° C.). $R_t$=1.356 min at 254 nm.

Example 59. (2,3-dichlorophenyl)((6S,10R)-2-methyl-4-(1-methyl-1H-pyrazol-5-yl)-5,6,7,8,9,10-hexahydro-6,10-epiminocycloocta[d]pyrimidin-11-yl)methanone Example 59 was made in a manner analogous to Example 56 substituting 2,3-dichlorobenzoic acid for 2-chloro-3-(trifluoromethyl)benzoic acid (14 mg, 29%). MS (ESI): mass calculated for $C_{22}H_{21}Cl_2ON_5$, 442.3; m/z found 443.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.242 min at 254 nm.

Example 60. (3-chloro-2-(trifluoromethyl)pyridin-4-yl)((6S,10R)-2-methyl-4-(1-methyl-1H-pyrazol-5-yl)-5,6,7,8,9,10-hexahydro-6,10-epiminocycloocta[d]pyrimidin-11-yl)methanone

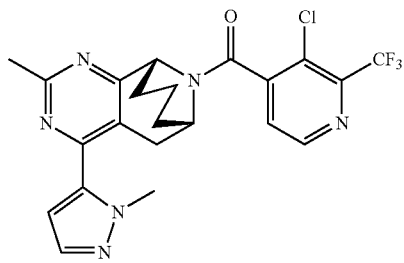 [SMILES: Cc1nc(-c2ccnn2C)c2c(n1)[C@H]1CCC[C@@H](C2)N1C(=O)c1ccnc(C(F)(F)F)c1Cl]

Example 60 was made in a manner analogous to Example 56 substituting 3-chloro-2-(trifluoromethyl)isonicotinic acid for 2-chloro-3-(trifluoromethyl)benzoic acid (16 mg, 29%). MS (ESI): mass calculated for $C_{22}H_{20}ClF_3ON_6$, 476.9; m/z found 476.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.231 min at 254 nm.

Example 61. (3-chloro-2-(trifluoromethyl)pyridin-4-yl)((6S,10R)-2-methyl-4-(pyridin-2-yl)-5,6,7,8,9,10-hexahydro-6,10-epiminocycloocta[d]pyrimidin-11-yl)methanone

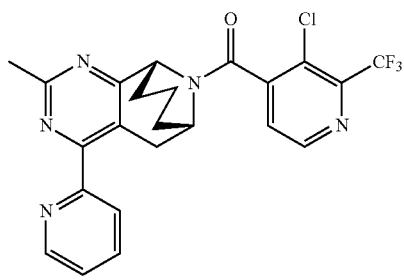 [SMILES: Cc1nc(-c2ccccn2)c2c(n1)[C@H]1CCC[C@@H](C2)N1C(=O)c1ccnc(C(F)(F)F)c1Cl]

Example 61 was made in a manner analogous to Example 3 wherein (6S,10R)-2-methyl-4-(pyridin-2-yl)-5,6,7,8,9,10-hexahydro-6,10-epiminocycloocta[d]pyrimidine was used in place of (6R,10S)-2-methyl-4-(1H-pyrazol-5-yl)-5,6,7,8,9,10-hexahydro-6,10-epiminocycloocta[d]pyrimidine and 3-chloro-2-(trifluoromethyl)isonicotinic acid was used in place of 2-chloro-3-(trifluoromethyl)benzoic acid (28 mg, 47%). MS (ESI): mass calculated for $C_{23}H_{19}ClF_3ON_5$, 473.9; m/z found 473.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=1.302 min at 254 nm.

Example 62. (2-methyl-3-(trifluoromethyl)phenyl)((6S,10R)-2-methyl-4-(pyridin-2-yl)-5,6,7,8,9,10-hexahydro-6,10-epiminocycloocta[d]pyrimidin-11-yl)methanone

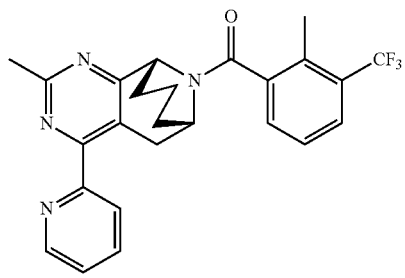 [SMILES: Cc1nc(-c2ccccn2)c2c(n1)[C@H]1CCC[C@@H](C2)N1C(=O)c1cccc(C(F)(F)F)c1C]

Example 62 was made in a manner analogous to Example 61 substituting 2-methyl-3-(trifluoromethyl)benzoic acid for 3-chloro-2-(trifluoromethyl)isonicotinic acid (37 mg, 65%). MS (ESI): mass calculated for $C_{25}H_{23}F_3ON_4$, 452.5; m/z found 454.0 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.2 mL/min (Temperature=50° C.). $R_t$=1.370 min at 254 nm.

Example 63. (2-chloro-3-(trifluoromethyl)phenyl)((6S,10R)-2-methyl-4-(pyridin-2-yl)-5,6,7,8,9,10-hexahydro-6,10-epiminocycloocta[d]pyrimidin-11-yl)methanone

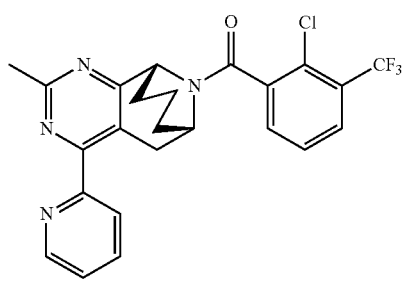 [SMILES: Cc1nc(-c2ccccn2)c2c(n1)[C@H]1CCC[C@@H](C2)N1C(=O)c1cccc(C(F)(F)F)c1Cl]

Example 63 was made in a manner analogous to Example 61 wherein 2-chloro-3-trifluoromethylbenzoic acid was used in place of 3-chloro-2-(trifluoromethyl)isonicotinic acid (24 mg, 41%). MS (ESI): mass calculated for $C_{24}H_{20}ClF_3ON_4$, 472.9; m/z found 473.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.2 mL/min (Temperature=50° C.). $R_t$=1.368 min at 254 nm.

Example 64. (2,4-dichloro-3-fluorophenyl)((6S,10R)-2-methyl-4-(pyridin-2-yl)-5,6,7,8,9,10-hexahydro-6,10-epiminocycloocta[d]pyrimidin-11-yl)methanone

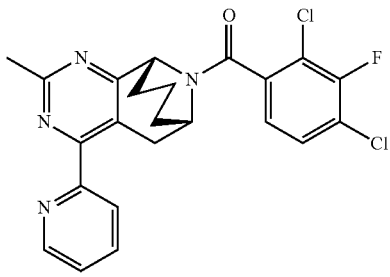 [SMILES: Cc1nc(-c2ccccn2)c2c(n1)[C@H]1CCC[C@@H](C2)N1C(=O)c1ccc(Cl)c(F)c1Cl]

Example 64 was made in a manner analogous to Example 61 substituting 2,4-dichloro-3-fluorobenzoic acid for 3-chloro-2-(trifluoromethyl)isonicotinic acid (40 mg, 70%). MS (ESI): mass calculated for $C_{23}H_{19}Cl_2FON_4$, 457.3; m/z found 457.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=0.768 min at 254 nm.

Example 65. (2,3-dichlorophenyl)((6S,10R)-2-methyl-4-(pyridin-2-yl)-5,6,7,8,9,10-hexahydro-6,10-epiminocycloocta[d]pyrimidin-11-yl)methanone

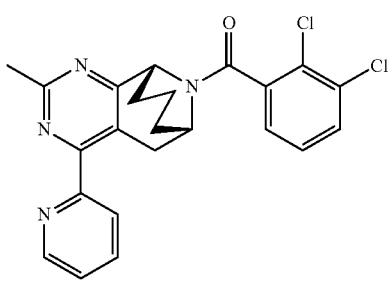 [SMILES: Cc1nc(-c2ccccn2)c2c(n1)[C@H]1CCC[C@@H](C2)N1C(=O)c1cccc(Cl)c1Cl]

Example 65 was made in a manner analogous to Example 61 substituting 2,3-dichlorobenzoic acid for 3-chloro-2-(trifluoromethyl)isonicotinic acid (22 mg, 40%). MS (ESI): mass calculated for $C_{23}H_{20}Cl_2ON_4$, 439.3; m/z found 438.9 [M+H]$^+$; Analytical HPLC was obtained on a Agilent 1100 Series using an Inertsil ODS-3 column (3 μM, 50×3 mM), mobile phase of 5-99% ACN in 0.05% TFA over 1.6 min and then hold at 99% ACN for 0.4 min, at a flow rate of 2.5 mL/min (Temperature=50° C.). $R_t$=0.726 min at 254 nm.

Examples 66-92 can be made according to the above examples, substituting the appropriate starting materials.

Example 66. (2-amino-4-(1H-pyrazol-3-yl)-5,6,7,8,9,10-hexahydro-6,10-epiminocycloocta[d]pyrimidin-11-yl)(2-chloro-3-(trifluoromethyl)phenyl)methanone

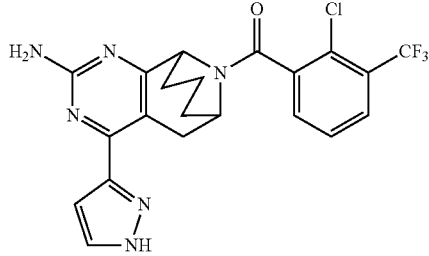 [SMILES: Nc1nc(-c2cc[nH]n2)c2c(n1)C1CCCC(C2)N1C(=O)c1cccc(C(F)(F)F)c1Cl]

Example 67. (4-(1H-pyrazol-3-yl)-5,6,7,8,9,10-hexahydro-6,10-epiminocycloocta[d]pyrimidin-11-yl)(2-chloro-3-(trifluoromethyl)phenyl)methanone

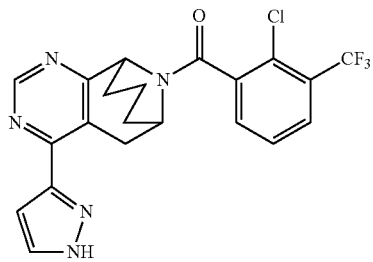 [SMILES: O=C(c1cccc(C(F)(F)F)c1Cl)N1C2CCCC1c1ncnc(-c3cc[nH]n3)c1C2]

Example 68. (2-chloro-3-(trifluoromethyl)phenyl)(2-isopropyl-4-(1H-pyrazol-3-yl)-5,6,7,8,9,10-hexahydro-6,10-epiminocycloocta[d]pyrimidin-11-yl)methanone

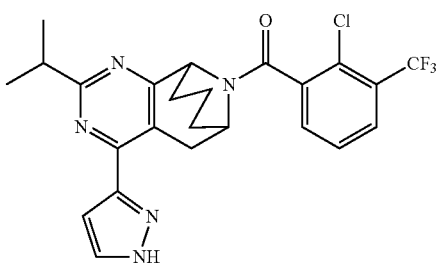 [SMILES: CC(C)c1nc(-c2cc[nH]n2)c2c(n1)C1CCCC(C2)N1C(=O)c1cccc(C(F)(F)F)c1Cl]

Example 69. (2-chloro-3-(trifluoromethyl)phenyl)(2-ethyl-4-(1H-pyrazol-3-yl)-5,6,7,8,9,10-hexahydro-6,10-epiminocycloocta[d]pyrimidin-11-yl)methanone

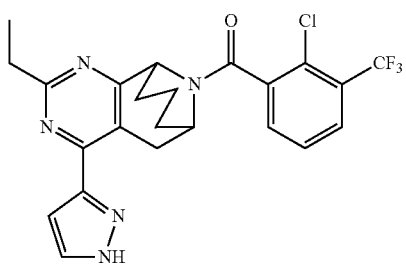 [SMILES: CCc1nc(-c2cc[nH]n2)c2c(n1)C1CCCC(C2)N1C(=O)c1cccc(C(F)(F)F)c1Cl]

Example 70. (2-chloro-3-(trifluoromethyl)phenyl)(2-methyl-4-(2H-1,2,3-triazol-2-yl)-5,6,7,8,9,10-hexahydro-6,10-epiminocycloocta[d]pyrimidin-11-yl)methanone

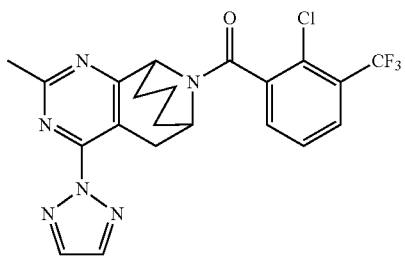 [SMILES: Cc1nc2c(c(-n3nccn3)n1)CC1CCCC2N1C(=O)c1cccc(C(F)(F)F)c1Cl]

Example 71. (2-chloro-3-(trifluoromethyl)phenyl)(4-(4-fluoro-1H-pyrazol-3-yl)-2-methyl-5,6,7,8,9,10-hexahydro-6,10-epiminocycloocta[d]pyrimidin-11-yl)methanone

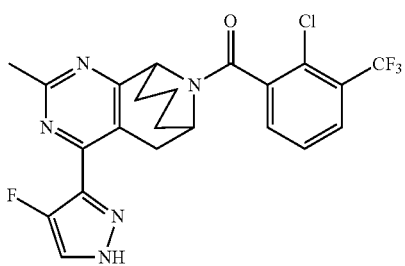

Example 72. (2-chloro-3-(trifluoromethyl)phenyl)(2-methyl-4-(4-(trifluoromethyl)-1H-pyrazol-3-yl)-5,6,7,8,9,10-hexahydro-6,10-epiminocycloocta[d]pyrimidin-11-yl)methanone

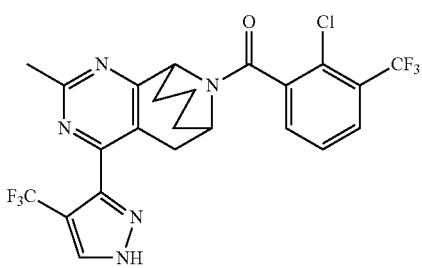 [SMILES: Cc1nc(-c2n[nH]cc2C(F)(F)F)c2c(n1)C1CCCC(C2)N1C(=O)c1cccc(C(F)(F)F)c1Cl]

Example 73. (2-chloro-3-(trifluoromethyl)phenyl)(4-(3,5-dimethylisoxazol-4-yl)-2-methyl-5,6,7,8,9,10-hexahydro-6,10-epiminocycloocta[d]pyrimidin-11-yl)methanone

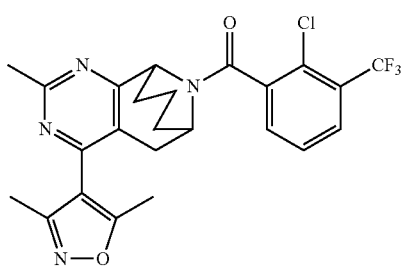 [SMILES: Cc1nc(-c2c(C)noc2C)c2c(n1)C1CCCC(C2)N1C(=O)c1cccc(C(F)(F)F)c1Cl]

Example 74. (4-(1H-imidazol-2-yl)-2-methyl-5,6,7,8,9,10-hexahydro-6,10-epiminocycloocta[d]pyrimidin-11-yl)(2-chloro-3-(trifluoromethyl)phenyl)methanone

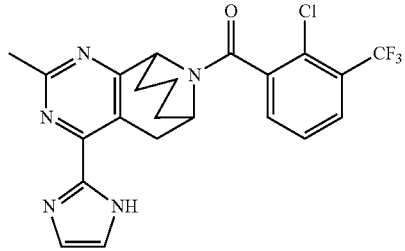 [SMILES: Cc1nc(-c2ncc[nH]2)c2c(n1)C1CCCC(C2)N1C(=O)c1cccc(C(F)(F)F)c1Cl]

Example 75. (2-chloro-3-(trifluoromethyl)phenyl)(2-methyl-4-(thiazol-2-yl)-5,6,7,8,9,10-hexahydro-6,10-epiminocycloocta[d]pyrimidin-11-yl)methanone

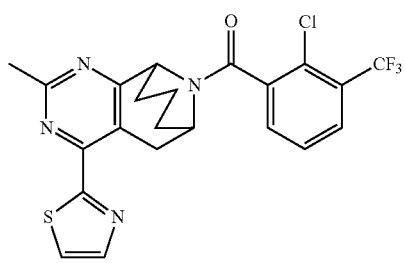 [SMILES: Cc1nc(-c2nccs2)c2c(n1)C1CCCC(C2)N1C(=O)c1cccc(C(F)(F)F)c1Cl]

Example 76. (2-chloro-3-(trifluoromethyl)phenyl)(2-methyl-4-(1H-pyrrol-2-yl)-5,6,7,8,9,10-hexahydro-6,10-epiminocycloocta[d]pyrimidin-11-yl)methanone

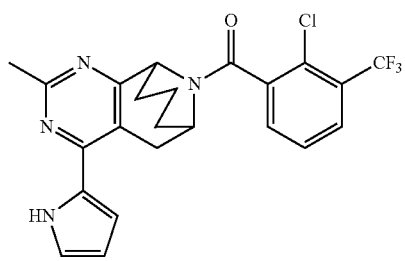 [SMILES: Cc1nc(-c2ccc[nH]2)c2c(n1)C1CCCC(C2)N1C(=O)c1cccc(C(F)(F)F)c1Cl]

Example 77. (2-chloro-3-(trifluoromethyl)phenyl)(2-methyl-4-(thiazol-4-yl)-5,6,7,8,9,10-hexahydro-6,10-epiminocycloocta[d]pyrimidin-11-yl)methanone

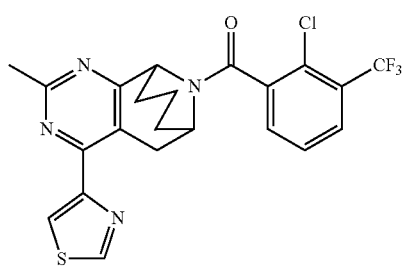 [SMILES: Cc1nc(-c2cscn2)c2c(n1)C1CCCC(C2)N1C(=O)c1cccc(C(F)(F)F)c1Cl]

Example 78. (2-chloro-3-(trifluoromethyl)phenyl) (4-(isoxazol-4-yl)-2-methyl-5,6,7,8,9,10-hexahydro-6,10-epiminocycloocta[d]pyrimidin-11-yl)methanone

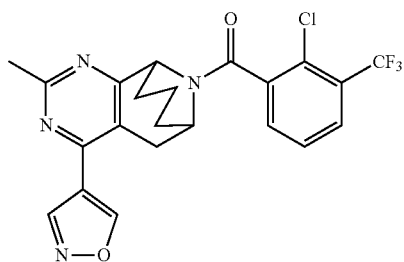 [SMILES: Cc1nc(-c2cnoc2)c2c(n1)C1CCCC(C2)N1C(=O)c1cccc(C(F)(F)F)c1Cl]

Example 79. (2-chloro-3-(trifluoromethyl)phenyl) (2-methyl-4-(thiophen-3-yl)-5,6,7,8,9,10-hexahydro-6,10-epiminocycloocta[d]pyrimidin-11-yl)methanone

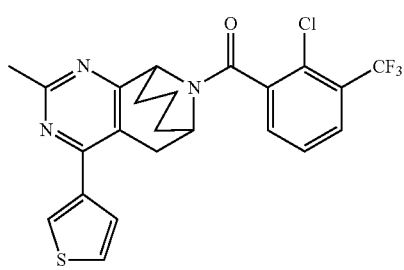 [SMILES: Cc1nc(-c2ccsc2)c2c(n1)C1CCCC(C2)N1C(=O)c1cccc(C(F)(F)F)c1Cl]

Example 80. (2-chloro-3-(trifluoromethyl)phenyl) (2-methyl-4-(4H-1,2,4-triazol-4-yl)-5,6,7,8,9,10-hexahydro-6,10-epiminocycloocta[d]pyrimidin-11-yl)methanone

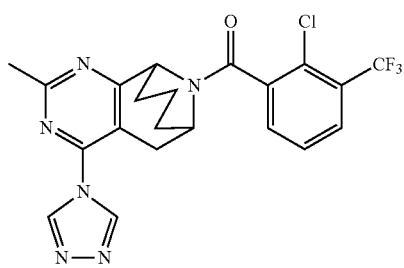 [SMILES: Cc1nc2c(c(-n3cnnc3)n1)CC1CCCC2N1C(=O)c1cccc(C(F)(F)F)c1Cl]

Example 81. (2-chloro-3-(trifluoromethyl)phenyl) (4-(5-hydroxypyrimidin-2-yl)-2-methyl-5,6,7,8,9,10-hexahydro-6,10-epiminocycloocta[d]pyrimidin-11-yl)methanone

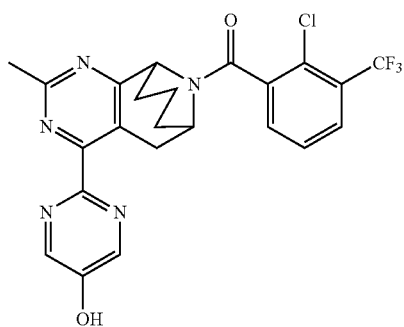 [SMILES: Cc1nc(-c2ncc(O)cn2)c2c(n1)C1CCCC(C2)N1C(=O)c1cccc(C(F)(F)F)c1Cl]

Example 82. (2-chloro-3-(trifluoromethyl)phenyl) (4-(5-fluoropyrimidin-2-yl)-2-methyl-5,6,7,8,9,10-hexahydro-6,10-epiminocycloocta[d]pyrimidin-11-yl)methanone

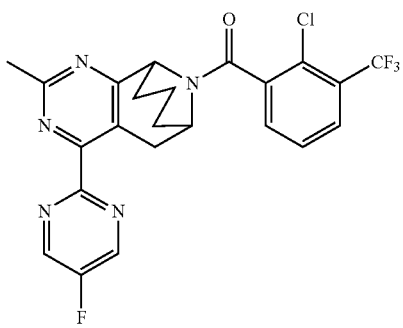 [SMILES: Cc1nc(-c2ncc(F)cn2)c2c(n1)C1CCCC(C2)N1C(=O)c1cccc(C(F)(F)F)c1Cl]

Example 83. (2-chloro-3-(trifluoromethyl)phenyl) (2-methyl-4-(4-methylpyrimidin-2-yl)-5,6,7,8,9,10-hexahydro-6,10-epiminocycloocta[d]pyrimidin-11-yl)methanone

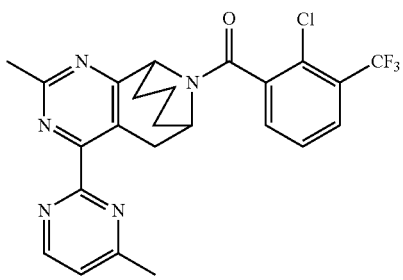 [SMILES: Cc1ccnc(-c2nc(C)nc3c2CC2CCCC3N2C(=O)c2cccc(C(F)(F)F)c2Cl)n1]

Example 84. (2-chloro-3-(trifluoromethyl)phenyl) (2-methyl-4-(5-methylpyridin-2-yl)-5,6,7,8,9,10-hexahydro-6,10-epiminocycloocta[d]pyrimidin-11-yl)methanone

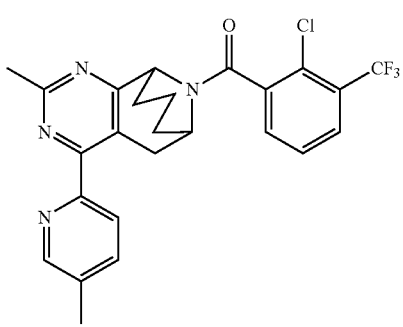 [SMILES: Cc1ccc(-c2nc(C)nc3c2CC2CCCC3N2C(=O)c2cccc(C(F)(F)F)c2Cl)nc1]

Example 85. (2-chloro-3-(trifluoromethyl)phenyl)(2-methyl-4-phenyl-5,6,7,8,9,10-hexahydro-6,10-epiminocycloocta[d]pyrimidin-11-yl)methanone

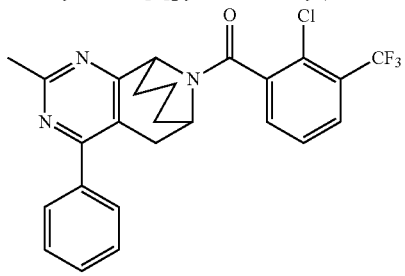

Example 86. (2-chloro-3-methylphenyl)(2-methyl-4-(1H-pyrazol-5-yl)-5,6,7,8,9,10-hexahydro-6,10-epiminocycloocta[d]pyrimidin-11-yl)methanone

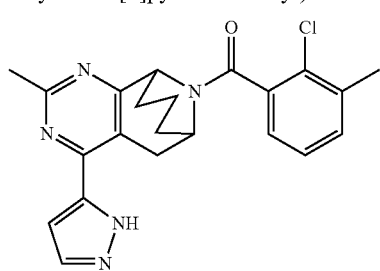

Example 87. (2-chloro-4-fluoro-3-(trifluoromethyl)phenyl)(2-methyl-4-(1H-pyrazol-5-yl)-5,6,7,8,9,10-hexahydro-6,10-epiminocycloocta[d]pyrimidin-11-yl)methanone

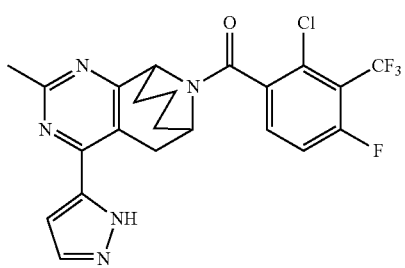 [SMILES: Cc1nc(-c2ccn[nH]2)c2c(n1)C1CCCC(C2)N1C(=O)c1ccc(F)c(C(F)(F)F)c1Cl]

Example 88. (3-methyl-2-(trifluoromethyl)pyridin-4-yl)(2-methyl-4-(1H-pyrazol-5-yl)-5,6,7,8,9,10-hexahydro-6,10-epiminocycloocta[d]pyrimidin-11-yl)methanone

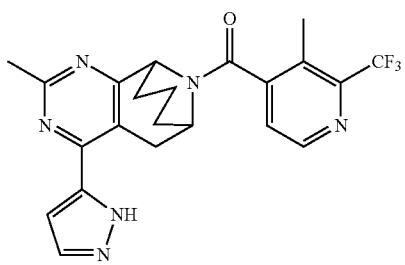 [SMILES: Cc1nc(-c2ccn[nH]2)c2c(n1)C1CCCC(C2)N1C(=O)c1ccnc(C(F)(F)F)c1C]

Example 89. (2,3-dimethylpyridin-4-yl)((6S,10R)-2-methyl-4-(1H-pyrazol-5-yl)-5,6,7,8,9,10-hexahydro-6,10-epiminocycloocta[d]pyrimidin-11-yl)methanone

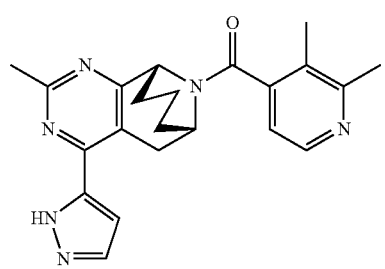

Example 90. (2-methyl-3-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone

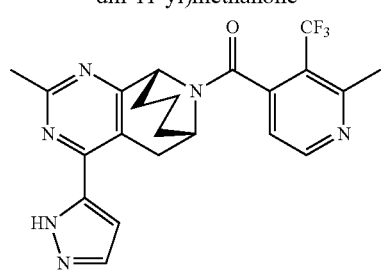

Example 91. (2,3-dimethylpyridin-4-yl)((6S,10R)-2-methyl-4-(1H-pyrazol-5-yl)-5,6,7,8,9,10-hexahydro-6,10-epiminocycloocta[d]pyrimidin-11-yl)methanone

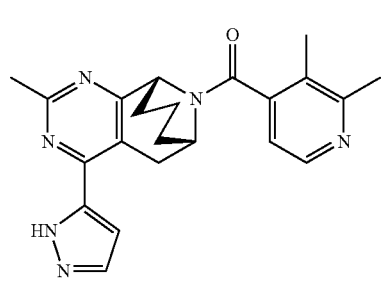

Example 92. (2-methyl-3-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone

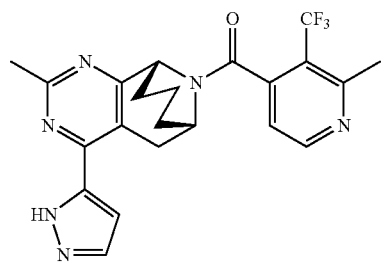

Pharmacological Examples

The in vitro affinity of the compounds of the invention for the rat and human P2X7 receptor was determined using a human peripheral blood mononuclear cells (PBMCs), a human whole blood assay, a $Ca^{2+}$ flux and radioligand binding assay in recombinant human P2X7 cells and recombinant rat P2X7 cells. In Tables 2, when the data cell has been left blank, it is intended to mean that the compound was not tested in that assay. The data represented in Tables 2 may represent a value from a single determination or when the experiment was run more than once, the data represents the average from between 2-12 runs.

P2X7 Antagonism in Human Peripheral Blood Mononuclear Cells (PBMCs) and Human Whole Blood.

Human blood was collected using a blood donor program. PBMCs were isolated from blood using a Ficoll density gradient technique. Briefly, blood was laid on Ficoll solution and centrifuged at ROOM TEMPERATURE for 20 minutes at 2000 rpm. The buffy layer (between red blood cells and plasma) was carefully collected by aspiration, washed with PBS and centrifuged again at 1500 rpm for 15 minutes. The resulting cell pellet was washed and plated on 96 well-plates for experiments. For the Human Whole Blood experiments, 150 µl of human blood was plated on 96 well-plates. Lipopolysaccharide (LPS) (30 ng/ml) was added to each well and incubated for 1 hour. Test compounds were then added and incubated for 30 minutes. The P2X7 agonist, 2'(3')-O-(4-benzoylbenzoyl) adenosine 5'-triphosphate (Bz-ATP) was then added at a final concentration of 0.5 mM (PBMC) or 1 mM (blood). Cells were incubated for an additional 1.5 hours. At that point, supernatant was collected and stored for IL-1β assay using manufacturer's protocol for enzyme-linked immunosorbant assay (ELISA). Data was expressed as percent control, where control is defined as the difference in IL-1β release in LPS+Bz-ATP samples and LPS only samples. Data was plotted as response (% control) versus concentration to generate $IC_{50}$ values. In Table 2, this data is represented by PBMC 10 µM (% control) and human whole blood $IC_{50}$ (µM). Data are analyzed and graphed on Graphpad Prism 5. For analysis, each concentration point is averaged from triplicate values and the averaged values are plotted on Graphpad Prism. The $IC_{50}$ for each compound is then uploaded into 3DX.

P2X7 Antagonism in Recombinant Human P2X7 Cells or Recombinant Rat P2X7 Cells:

Radioligand Binding:

human or rat P2X7-1321N1 cells were collected and frozen @ −80° C. On the day of the experiment, cell membrane preparations were made according to standard published methods. The total assay volume was 100 µl: 10 µl compound (10×)+(b) 40 µl tracer (2.5×)+50 µl membrane (2×). The tracer used for the assay was tritiated A-804598. The compound can be prepared as described in the literature. (Donnelly-Roberts, D. *Neuropharmacology* 2008, 56 (1), 223-229.) Compounds, tracer and membranes were incubated for 1 hour @ 4° C. The assay was terminated by filtration (GF/B filters pre-soaked with 0.3% PEI) and washed with washing buffer (Tris-HCl 50 mM). The $IC_{50}$ generated in the binding assay was corrected for tracer concentration and affinity of the tracer to derive at the affinity ($K_i$) of the test compounds. The data are presented in Table 2 under the headings: P2X7 human $K_i$ (µM) and P2X7 rat $K_i$ (µM). Data are analyzed and graphed on Graphpad Prism 5. For analysis, each concentration point is averaged from triplicate values and the averaged values are plotted on Graphpad Prism.

TABLE 2*

P2X7 activity of the compounds of Formula (I) in a panel of in-vitro assays

| Example # | PBMC @10 µM (% control) | P2X7 Human $K_i$ (µM) | P2X7 Rat $IC_{50}$ (µM) | Human Whole Blood $IC_{50}$ (µM) |
|---|---|---|---|---|
| 1 | 3.3 | 0.0316 | 0.1009 | 0.027 |
| 2 | 1.1 | 0.0224 | nt | nt |
| 3 | 22.0 | nt | 0.8110 | 1.114 |
| 4 | 25.4 | nt | 0.9484 | 1.361 |
| 5 | 76.5 | nt | >10 | 1.995 |
| 6 | 18.1 | nt | 0.9705 | 1.125 |
| 7 | 20.5 | nt | 0.9205 | 2.350 |
| 8 | 31.9 | nt | 0.6012 | 1.556 |
| 9 | 91.3 | nt | >10 | 2.965 |
| 10 | 22.4 | 0.6310 | 6.6069 | 0.459 |
| 11 | 24.4 | 0.5012 | 0.9441 | 0.302 |
| 12 | 92.6 | nt | >10 | 6.124 |
| 13 | 22.2 | nt | 0.0889 | 5.082 |
| 15 | 38.7 | nt | 0.0982 | 5.047 |
| 15 | 95.1 | nt | 35.9750 | 13.305 |
| 16 | 84.8 | nt | >10 | 7.379 |
| 17 | 13.3 | nt | 1.7906 | 2.018 |
| 18 | 28.9 | nt | >10 | 12.078 |
| 19 | −3.0 | 0.0331 | 0.0122 | 0.055 |
| 20 | −9.9 | 0.1202 | 11.0154 | 0.221 |
| 21 | −26.4 | 0.0316 | 0.0332 | 0.026 |
| 22 | 26.8 | 0.3162 | >10 | 0.286 |
| 23 | −24.7 | 0.0316 | 0.4842 | 0.018 |
| 24 | 2.4 | 0.1259 | 0.0192 | 0.038 |
| 25 | −10.2 | 0.0200 | 0.0187 | 0.025 |
| 26 | −3.8 | 0.0631 | 0.0414 | 0.030 |
| 27 | −10.2 | 0.1514 | 0.1318 | 0.172 |
| 28 | −25.1 | 0.1259 | 7.9433 | 0.423 |
| 29 | −22.9 | 0.0200 | 0.2065 | 0.008 |
| 30 | −3.7 | 0.2512 | >10 | 0.485 |
| 31 | −0.9 | nt | >10 | 2.667 |
| 32 | 4.8 | nt | >10 | 1.581 |
| 33 | 1.2 | nt | >10 | 1.343 |
| 34 | 3.3 | nt | >10 | 8.590 |
| 35 | 9.1 | nt | >10 | 2.296 |
| 36 | 73.8 | nt | nt | nt |
| 37 | 13.3 | nt | >10 | 20.893 |
| 38 | 46.8 | nt | >10 | >10 |
| 39 | 1.0 | nt | >10 | 1.094 |
| 40 | 76.2 | nt | nt | nt |
| 41 | −5.6 | 0.0295 | 0.0158 | 0.021 |
| 42 | −16.1 | 0.1259 | 0.1574 | 0.107 |
| 43 | 15.0 | 0.1259 | 0.0417 | 0.098 |
| 44 | −11.6 | 0.0501 | 0.2506 | 0.156 |
| 45 | −14.2 | 0.0251 | 0.1279 | 0.064 |
| 46 | −4.2 | 0.0316 | 0.0141 | 0.088 |
| 47 | −3.4 | 0.0398 | 0.2449 | 0.040 |
| 48 | −4.3 | 0.0251 | 0.0543 | 0.015 |
| 49 | −1.9 | 0.1995 | 0.1390 | 1.000 |
| 50 | −2.2 | 0.0933 | 0.0678 | 0.158 |
| 51 | −3.0 | 0.0447 | 0.0166 | 0.043 |
| 52 | −1.2 | 0.0603 | 0.0818 | 0.433 |
| 53 | 0.0 | 0.0316 | 0.1910 | 0.131 |
| 54 | 9.3 | 0.0724 | 0.3715 | 0.054 |
| 55 | −1.6 | 0.1047 | 0.2168 | 0.037 |
| 56 | −2.9 | 0.1000 | 0.0116 | 0.048 |
| 57 | −0.3 | 0.1905 | 0.5970 | 0.191 |
| 58 | −3.3 | 0.0933 | 0.8054 | 0.130 |
| 59 | −1.8 | 0.1349 | 1.0914 | 0.372 |
| 60 | 21.4 | nt | 0.7980 | 1.977 |
| 61 | 0.4 | 0.0933 | 0.0460 | 0.179 |
| 62 | −1.4 | 0.0631 | 0.0513 | 0.058 |
| 63 | −0.9 | 0.0398 | 0.0331 | 0.068 |
| 64 | −2.8 | 0.0200 | 0.3763 | 0.037 |
| 65 | 0.1 | 0.0490 | 0.1841 | 0.042 |

*Indicates not tested

What is claimed:

1. A compound of Formula (I)

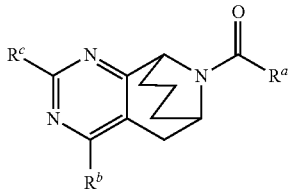 (I)

or enantiomers or diastereomers thereof;
or pharmaceutically acceptable salts thereof;
wherein:
$R^a$ is

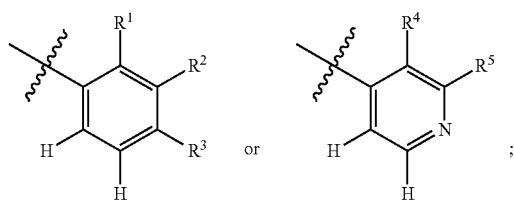;

$R^1$, $R^2$, $R^3$, and $R^4$ are each independently selected from the group consisting of: H, halo, $C_1$-$C_3$alkyl and $C_1$-$C_3$perhaloalkyl;
$R^5$ is $C_1$-$C_3$perhaloalkyl or $C_1$-$C_3$alkyl;
$R^b$ is selected from the group consisting of:

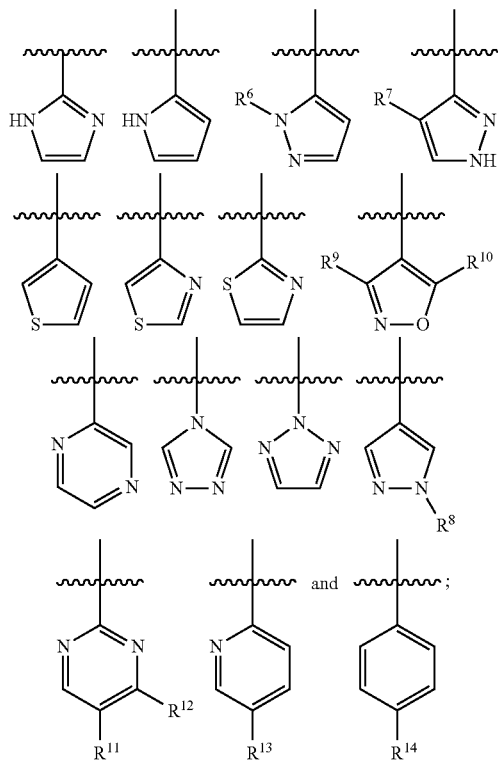

Wherein:
$R^6$, $R^8$, $R^9$, $R^{10}$, $R^{12}$, $R^{13}$ are independently H or $C_1$-$C_3$alkyl,
$R^7$ is H, halo or $C_1$-$C_3$perhaloalkyl,
$R^{11}$ is H, halo or OH;
$R^{14}$ is H or halo; and
$R^c$ is selected from the group consisting of: H, $NH_2$, $C_1$-$C_4$alkyl.

2. A compound as in claim 1 wherein, $R^a$ is

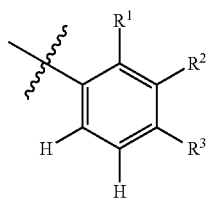

and $R^1$ is halo or $C_1$-$C_3$perhaloalkyl.

3. A compound as in claim 1 wherein, $R^a$ is

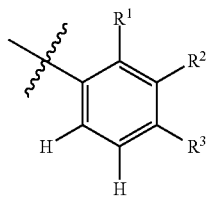

and $R^1$ is halo.

4. A compound as in claim 1 wherein wherein is $R^a$ is

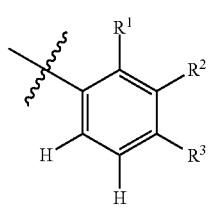

and $R^2$ is $C_1$-$C_3$perhaloalkyl.

5. A compound as in claim 1 wherein, $R^a$ is

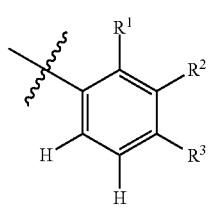

and $R^3$ is halo.

6. A compound as in claim 1 wherein, $R^a$ is

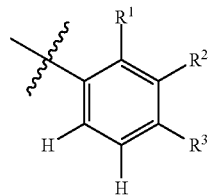

and $R^1$ is independently selected from the group consisting of: halo, $C_1$-$C_3$alkyl and $C_1$-$C_3$perhaloalkyl, $R^2$ is independently selected from the group consisting of: halo, $C_1$-$C_3$alkyl and $C_1$-$C_3$perhaloalkyl and $R^3$ is H or halo.

7. A compound as in claim 1 wherein, $R^a$ is

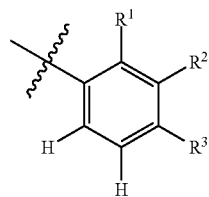

and $R^1$ is independently selected from the group consisting of: halo and $C_1$-$C_3$perhaloalkyl and $R^2$ is independently selected from the group consisting of: halo and $C_1$-$C_3$perhaloalkyl, and $R^3$ is H.

8. A compound as in claim 1 wherein, $R^a$ is

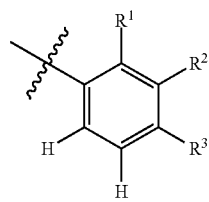

and $R^1$ is halo and $R^2$ is $C_1$-$C_3$perhaloalkyl.

9. A compound as in claim 1 wherein, $R^a$ is

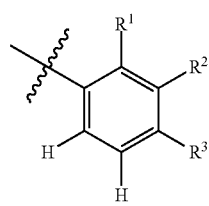

and $R^1$ and $R^2$ are halo and $R^3$ is H.

10. A compound as in claim 1 wherein, $R^a$ is

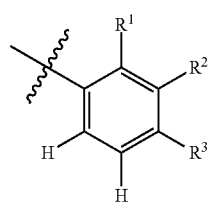

and $R^1$, $R^2$ and $R^3$ are halo.

11. A compound as in claim 1 wherein, $R^a$ is

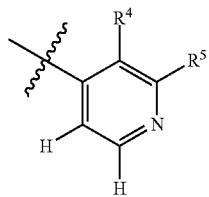

and $R^4$ is independently selected from the group consisting of: halo, $C_1$-$C_3$alkyl and $C_1$-$C_3$perhaloalkyl.

12. A compound as in claim 1 wherein, $R^a$ is

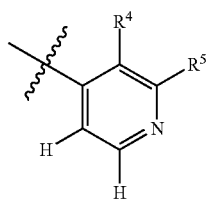

and $R^4$ is halo or $C_1$-$C_3$perhaloalkyl.

13. A compound as in claim 1 wherein, $R^a$ is

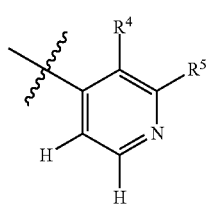

and $R^4$ is halo.

14. A compound as in claim 1 wherein, $R^a$ is

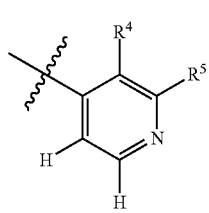

and $R^5$ is $C_1$-$C_3$alkyl or $C_1$-$C_3$perhaloalkyl.

15. A compound as in claim 1 wherein, $R^a$ is

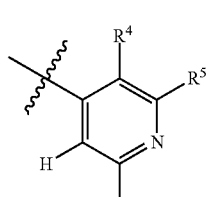

and $R^5$ is $C_1$-$C_3$perhaloalkyl.

16. A compound as in claim 1 wherein, $R^a$ is

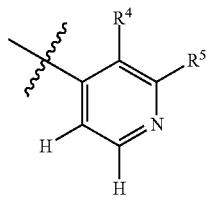

and $R^4$ is independently selected from the group consisting of: halo, $C_1$-$C_3$alkyl and $C_1$-$C_3$perhaloalkyl and $R^5$ is $C_1$-$C_3$alkyl or $C_1$-$C_3$perhaloalkyl.

17. A compound as in claim 1 wherein, $R^a$ is

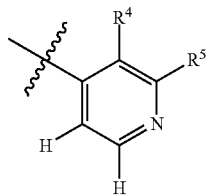

and $R^4$ is independently selected from the group consisting of: halo and $C_1$-$C_3$perhaloalkyl and $R^5$ is $C_1$-$C_3$perhaloalkyl.

18. A compound as in claim 1 wherein, $R^a$ is

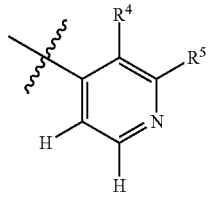

and $R^4$ is halo and $R^5$ is $C_1$-$C_3$perhaloalkyl.

19. A compound as in claim 1 wherein, $R^b$ is selected from the group consisting of:

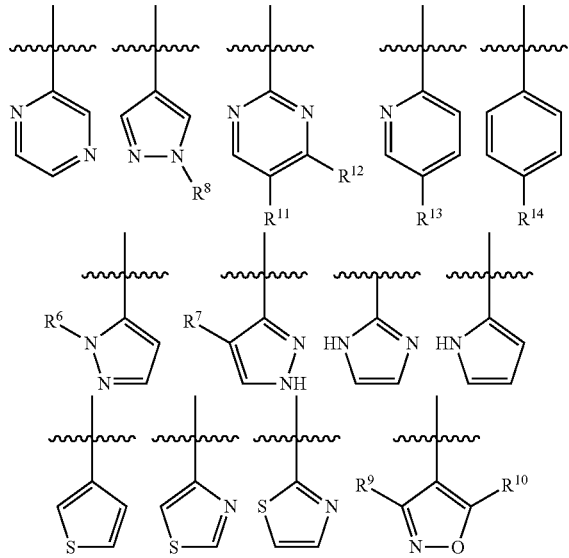

-continued

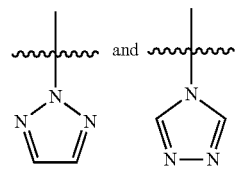

20. A compound as in claim 1 wherein, $R^b$ is selected from the group consisting of:

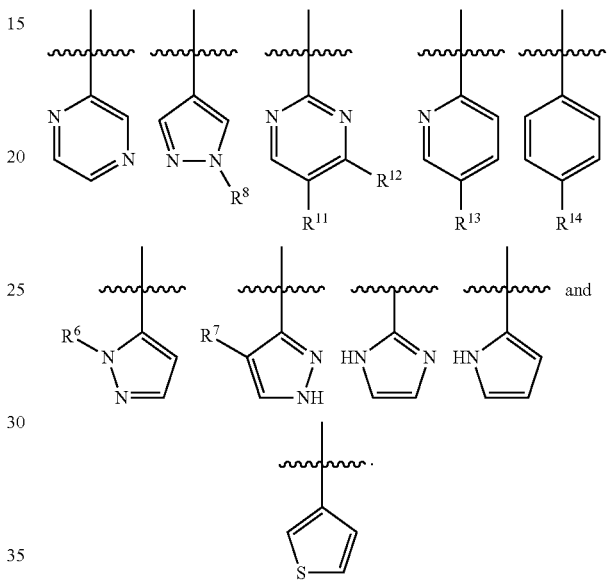

21. A compound as in claim 1 wherein, $R^b$ is selected from the group consisting of:

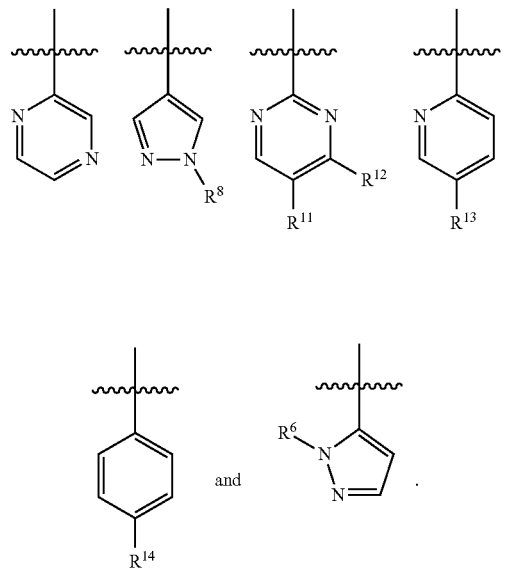

22. A compound as in claim 1 wherein, $R^b$ is selected from the group consisting of:

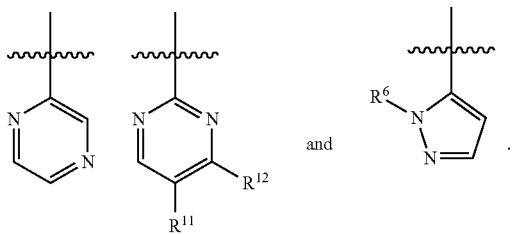 and 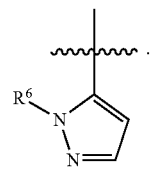

23. A compound as in claim 1 wherein, $R^b$ is

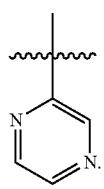

24. A compound as in claim 1 wherein, $R^b$ is

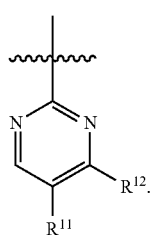

25. A compound as in claim 1 wherein, $R^b$ is

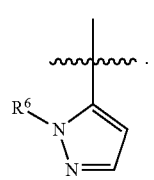

26. A compound as in claim 1 wherein $R^c$ is selected from the group consisting of: H, $NH_2$, and 01-$C_4$alkyl.

27. A compound as in claim 1 wherein $R^c$ is H or $C_1$-$C_4$alkyl.

28. A compound as in claim 1 wherein $R^c$ is $C_1$-$C_4$alkyl.

29. A compound as in claim 1 wherein $R^a$ is

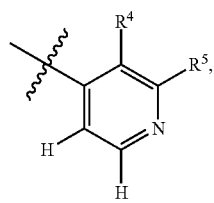

$R^4$ is halo, $R^5$ is $C_1$-$C_3$perhaloalkyl, $R^c$ is $C_1$-$C_4$alkyl, $R^6$ is H, and $R^b$ is 30. A compound as in claim 1 wherein, $R^a$ is

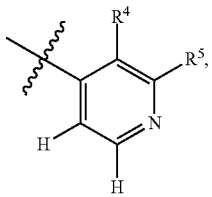

$R^4$ is halo, $R^5$ is $C_1$-$C_3$perhaloalkyl, $R^c$ is $C_1$-$C_4$alkyl, $R^6$ is $CH_3$, $R^b$ is

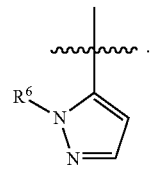

31. A compound as in claim 1 wherein, is $R^a$ is

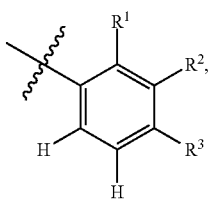

$R^1$ is halo, $R^2$ is $C_1$-$C_3$perhaloalkyl, $R^3$ is H, $R^c$ is $C_1$-$C_4$alkyl, $R^6$ is H, $R^b$ is

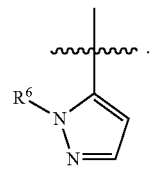

32. A compound as in claim 1 wherein, is $R^a$ is

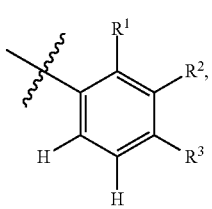

$R^1$ is halo, $R^2$ is $C_1$-$C_3$perhaloalkyl, $R^3$ is H, $R^c$ is $C_1$-$C_4$alkyl, $R^{11}$ and $R^{12}$ are H, $R^b$ is

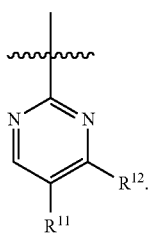

33. A compound as in claim 1 wherein, $R^a$ is

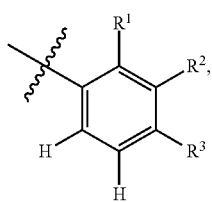

$R^1$ is halo, $R^2$ is $C_1$-$C_3$perhaloalkyl, $R^3$ is H, $R^c$ is $C_1$-$C_4$alkyl, and $R^b$ is

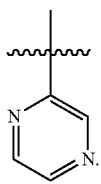

34. A compound independently selected from the group consisting of:
 (2,3-dichlorophenyl)(2-methyl-4-(1H-pyrazol-5-yl)-5,6,7,8,9,10-hexahydro-6,10-epiminocycloocta[d]pyrimidin-11-yl)methanone,
 (2-chloro-3-(trifluoromethyl)phenyl)(2-methyl-4-(1H-pyrazol-5-yl)-5,6,7,8,9,10-hexahydro-6,10-epiminocycloocta[d]pyrimidin-11-yl)methanone,
 (2-chloro-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone,
 (2,3-dichloro-4-fluorophenyl)((6R,10S)-2-methyl-4-(1H-pyrazol-5-yl)-5,6,7,8,9,10-hexahydro-6,10-epiminocycloocta[d]pyrimidin-11-yl)methanone,
 (2,4-dichlorophenyl)((6R,10S)-2-methyl-4-(1H-pyrazol-5-yl)-5,6,7,8,9,10-hexahydro-6,10-epiminocycloocta[d]pyrimidin-11-yl)methanone,
 (2-methyl-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone,
 (3-chloro-2-(trifluoromethyl)pyridin-4-yl)((6R,10S)-2-methyl-4-(1H-pyrazol-5-yl)-5,6,7,8,9,10-hexahydro-6,10-epiminocycloocta[d]pyrimidin-11-yl)methanone,
 (2-fluoro-3-(trifluoromethyl)phenyl)((6R,10S)-2-methyl-4-(1H-pyrazol-5-yl)-5,6,7,8,9,10-hexahydro-6,10-epiminocycloocta[d]pyrimidin-11-yl)methanone,
 (2-chloro-4-fluorophenyl)((6R,10S)-2-methyl-4-(1H-pyrazol-5-yl)-5,6,7,8,9,10-hexahydro-6,10-epiminocycloocta[d]pyrimidin-11-yl)methanone,
 (2,4-dichloro-3-fluorophenyl)((6R,10S)-2-methyl-4-(1H-pyrazol-5-yl)-5,6,7,8,9,10-hexahydro-6,10-epiminocycloocta[d]pyrimidin-11-yl)methanone,
 (2,3-dichlorophenyl)((6R,10S)-2-methyl-4-(1H-pyrazol-5-yl)-5,6,7,8,9,10-hexahydro-6,10-epiminocycloocta[d]pyrimidin-11-yl)methanone,
 (4-chloro-2-fluorophenyl)((6R,10S)-2-methyl-4-(1H-pyrazol-5-yl)-5,6,7,8,9,10-hexahydro-6,10-epiminocycloocta[d]pyrimidin-11-yl)methanone,
 (2-chloro-3-(trifluoromethyl)phenyl)((6R,10S)-4-(4-fluorophenyl)-2-methyl-5,6,7,8,9,10-hexahydro-6,10-epiminocycloocta[d]pyrimidin-11-yl)methanone,
 ((6R,10S)-4-(4-fluorophenyl)-2-methyl-5,6,7,8,9,10-hexahydro-6,10-epiminocycloocta[d]pyrimidin-11-yl)(2-methyl-3-(trifluoromethyl)phenyl)methanone,
 (2,4-dichlorophenyl)((6R,10S)-4-(4-fluorophenyl)-2-methyl-5,6,7,8,9,10-hexahydro-6,10-epiminocycloocta[d]pyrimidin-11-yl)methanone,
 (2-chloro-4-fluorophenyl)((6R,10S)-4-(4-fluorophenyl)-2-methyl-5,6,7,8,9,10-hexahydro-6,10-epiminocycloocta[d]pyrimidin-11-yl)methanone,
 (2,3-dichloro-4-fluorophenyl)((6R,10S)-4-(4-fluorophenyl)-2-methyl-5,6,7,8,9,10-hexahydro-6,10-epiminocycloocta[d]pyrimidin-11-yl)methanone,
 (3-chloro-2-(trifluoromethyl)pyridin-4-yl)((6R,10S)-4-(4-fluorophenyl)-2-methyl-5,6,7,8,9,10-hexahydro-6,10-epiminocycloocta[d]pyrimidin-11-yl)methanone,
 (2-chloro-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone,
 (2,4-dichlorophenyl)((6S,10R)-2-methyl-4-(1H-pyrazol-5-yl)-5,6,7,8,9,10-hexahydro-6,10-epiminocycloocta[d]pyrimidin-11-yl)methanone,
 (2-methyl-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone,
 (2-chloro-4-fluorophenyl)((6S,10R)-2-methyl-4-(1H-pyrazol-5-yl)-5,6,7,8,9,10-hexahydro-6,10-epiminocycloocta[d]pyrimidin-11-yl)methanone,
 (2,4-dichloro-3-fluorophenyl)((6S,10R)-2-methyl-4-(1H-pyrazol-5-yl)-5,6,7,8,9,10-hexahydro-6,10-epiminocycloocta[d]pyrimidin-11-yl)methanone,
 (3-chloro-2-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone,
 (2,3-dichloro-4-fluorophenyl)((6S,10R)-2-methyl-4-(1H-pyrazol-5-yl)-5,6,7,8,9,10-hexahydro-6,10-epiminocycloocta[d]pyrimidin-11-yl)methanone,
 (2-fluoro-3-(trifluoromethyl)phenyl)((6S,10R)-2-methyl-4-(1H-pyrazol-5-yl)-5,6,7,8,9,10-hexahydro-6,10-epiminocycloocta[d]pyrimidin-11-yl)methanone,
 (3-fluoro-2-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone,
 (4-chloro-2-fluorophenyl)((6S,10R)-2-methyl-4-(1H-pyrazol-5-yl)-5,6,7,8,9,10-hexahydro-6,10-epiminocycloocta[d]pyrimidin-11-yl)methanone,
 (2,3-dichlorophenyl)((6S,10R)-2-methyl-4-(1H-pyrazol-5-yl)-5,6,7,8,9,10-hexahydro-6,10-epiminocycloocta[d]pyrimidin-11-yl)methanone,
 (2-chloro-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
 (2,3-dichlorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
 (3-chloro-2-(trifluoromethyl)pyridin-4-yl)((6S,10R)-2-methyl-4-(1-methyl-1H-pyrazol-4-yl)-5,6,7,8,9,10-hexahydro-6,10-epiminocycloocta[d]pyrimidin-11-yl)methanone, (2,3-dichloro-4-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
(2-fluoro-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
(2,4-dichloro-3-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
(2-chloro-4-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
(3-fluoro-2-(trifluoromethyl)pyridin-4-yl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
(4-chloro-2-fluorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
(2-methyl-3-(trifluoromethyl)phenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
(2,4-dichlorophenyl)((6S,10R)-2-methyl-4-(1-methyl-1H-pyrazol-4-yl)-5,6,7,8,9,10-hexahydro-6,10-epiminocycloocta[d]pyrimidin-11-yl)methanone,
(2-chloro-3-(trifluoromethyl)phenyl)((6S,10R)-2-methyl-4-(pyrimidin-2-yl)-5,6,7,8,9,10-hexahydro-6,10-epiminocycloocta[d]pyrimidin-11-yl)methanone,
(3-chloro-2-(trifluoromethyl)pyridin-4-yl)((6S,10R)-2-methyl-4-(pyrimidin-2-yl)-5,6,7,8,9,10-hexahydro-6,10-epiminocycloocta[d]pyrimidin-11-yl)methanone,
(2-methyl-3-(trifluoromethyl)phenyl)((6S,10R)-2-methyl-4-(pyrimidin-2-yl)-5,6,7,8,9,10-hexahydro-6,10-epiminocycloocta[d]pyrimidin-11-yl)methanone,
(2,4-dichloro-3-fluorophenyl)((6S,10R)-2-methyl-4-(pyrimidin-2-yl)-5,6,7,8,9,10-hexahydro-6,10-epiminocycloocta[d]pyrimidin-11-yl)methanone,
(2,3-dichlorophenyl)((6S,10R)-2-methyl-4-(pyrimidin-2-yl)-5,6,7,8,9,10-hexahydro-6,10-epiminocycloocta[d]pyrimidin-11-yl)methanone,
(2-chloro-3-(trifluoromethyl)phenyl)((6S,10R)-2-methyl-4-(pyrazin-2-yl)-5,6,7,8,9,10-hexahydro-6,10-epiminocycloocta[d]pyrimidin-11-yl)methanone,
(2,4-dichloro-3-fluorophenyl)((6S,10R)-2-methyl-4-(pyrazin-2-yl)-5,6,7,8,9,10-hexahydro-6,10-epiminocycloocta[d]pyrimidin-11-yl)methanone,
(2,3-dichlorophenyl)((6S,10R)-2-methyl-4-(pyrazin-2-yl)-5,6,7,8,9,10-hexahydro-6,10-epiminocycloocta[d]pyrimidin-11-yl)methanone,
(3-chloro-2-(trifluoromethyl)pyridin-4-yl)((6S,10R)-2-methyl-4-(pyrazin-2-yl)-5,6,7,8,9,10-hexahydro-6,10-epiminocycloocta[d]pyrimidin-11-yl)methanone,
(2-methyl-3-(trifluoromethyl)phenyl)((6S,10R)-2-methyl-4-(pyrazin-2-yl)-5,6,7,8,9,10-hexahydro-6,10-epiminocycloocta[d]pyrimidin-11-yl)methanone,
(2-chloro-3-(trifluoromethyl)phenyl)((6S,10R)-4-(4-fluorophenyl)-2-methyl-5,6,7,8,9,10-hexahydro-6,10-epiminocycloocta[d]pyrimidin-11-yl)methanone,
(3-chloro-2-(trifluoromethyl)pyridin-4-yl)((6S,10R)-4-(4-fluorophenyl)-2-methyl-5,6,7,8,9,10-hexahydro-6,10-epiminocycloocta[d]pyrimidin-11-yl)methanone,
((6S,10R)-4-(4-fluorophenyl)-2-methyl-5,6,7,8,9,10-hexahydro-6,10-epiminocycloocta[d]pyrimidin-11-yl)(2-methyl-3-(trifluoromethyl)phenyl)methanone,
(2,4-dichloro-3-fluorophenyl)((6S,10R)-4-(4-fluorophenyl)-2-methyl-5,6,7,8,9,10-hexahydro-6,10-epiminocycloocta[d]pyrimidin-11-yl)methanone,
(2,3-dichlorophenyl)((6S,10R)-4-(4-fluorophenyl)-2-methyl-5,6,7,8,9,10-hexahydro-6,10-epiminocycloocta[d]pyrimidin-11-yl)methanone,
(2-chloro-3-(trifluoromethyl)phenyl)((6S,10R)-2-methyl-4-(1-methyl-1H-pyrazol-5-yl)-5,6,7,8,9,10-hexahydro-6,10-epiminocycloocta[d]pyrimidin-11-yl)methanone,
(2-methyl-3-(trifluoromethyl)phenyl)((6S,10R)-2-methyl-4-(1-methyl-1H-pyrazol-5-yl)-5,6,7,8,9,10-hexahydro-6,10-epiminocycloocta[d]pyrimidin-11-yl)methanone,
(2,4-dichloro-3-fluorophenyl)((6S,10R)-2-methyl-4-(1-methyl-1H-pyrazol-5-yl)-5,6,7,8,9,10-hexahydro-6,10-epiminocycloocta[d]pyrimidin-11-yl)methanone,
(2,3-dichlorophenyl)((6S,10R)-2-methyl-4-(1-methyl-1H-pyrazol-5-yl)-5,6,7,8,9,10-hexahydro-6,10-epiminocycloocta[d]pyrimidin-11-yl)methanone,
(3-chloro-2-(trifluoromethyl)pyridin-4-yl)((6S,10R)-2-methyl-4-(1-methyl-1H-pyrazol-5-yl)-5,6,7,8,9,10-hexahydro-6,10-epiminocycloocta[d]pyrimidin-11-yl)methanone,
(3-chloro-2-(trifluoromethyl)pyridin-4-yl)((6S,10R)-2-methyl-4-(pyridin-2-yl)-5,6,7,8,9,10-hexahydro-6,10-epiminocycloocta[d]pyrimidin-11-yl)methanone,
(2-methyl-3-(trifluoromethyl)phenyl)((6S,10R)-2-methyl-4-(pyridin-2-yl)-5,6,7,8,9,10-hexahydro-6,10-epiminocycloocta[d]pyrimidin-11-yl)methanone,
(2-chloro-3-(trifluoromethyl)phenyl)((6S,10R)-2-methyl-4-(pyridin-2-yl)-5,6,7,8,9,10-hexahydro-6,10-epiminocycloocta[d]pyrimidin-11-yl)methanone,
(2,4-dichloro-3-fluorophenyl)((6S,10R)-2-methyl-4-(pyridin-2-yl)-5,6,7,8,9,10-hexahydro-6,10-epiminocycloocta[d]pyrimidin-11-yl)methanone,
(2,3-dichlorophenyl)((6S,10R)-2-methyl-4-(pyridin-2-yl)-5,6,7,8,9,10-hexahydro-6,10-epiminocycloocta[d]pyrimidin-11-yl)methanone,
(2-amino-4-(1H-pyrazol-3-yl)-5,6,7,8,9,10-hexahydro-6,10-epiminocycloocta[d]pyrimidin-11-yl)(2-chloro-3-(trifluoromethyl)phenyl)methanone,
(4-(1H-pyrazol-3-yl)-5,6,7,8,9,10-hexahydro-6,10-epiminocycloocta[d]pyrimidin-11-yl)(2-chloro-3-(trifluoromethyl)phenyl)methanone,
(2-chloro-3-(trifluoromethyl)phenyl)(2-isopropyl-4-(1H-pyrazol-3-yl)-5,6,7,8,9,10-hexahydro-6,10-epiminocycloocta[d]pyrimidin-11-yl)methanone,
(2-chloro-3-(trifluoromethyl)phenyl)(2-ethyl-4-(1H-pyrazol-3-yl)-5,6,7,8,9,10-hexahydro-6,10-epiminocycloocta[d]pyrimidin-11-yl)methanone,
(2-chloro-3-(trifluoromethyl)phenyl)(2-methyl-4-(2H-1,2,3-triazol-2-yl)-5,6,7,8,9,10-hexahydro-6,10-epiminocycloocta[d]pyrimidin-11-yl)methanone,
(2-chloro-3-(trifluoromethyl)phenyl)(4-(4-fluoro-1H-pyrazol-3-yl)-2-methyl-5,6,7,8,9,10-hexahydro-6,10-epiminocycloocta[d]pyrimidin-11-yl)methanone,
(2-chloro-3-(trifluoromethyl)phenyl)(2-methyl-4-(4-(trifluoromethyl)-1H-pyrazol-3-yl)-5,6,7,8,9,10-hexahydro-6,10-epiminocycloocta[d]pyrimidin-11-yl)methanone,
(2-chloro-3-(trifluoromethyl)phenyl)(4-(3, 5-dim ethyl-isoxazol-4-yl)-2-methyl-5,6,7,8,9,10-hexahydro-6,10-epiminocycloocta[d]pyrimidin-11-yl)methanone,
(4-(1H-imidazol-2-yl)-2-methyl-5,6,7,8,9,10-hexahydro-6,10-epiminocycloocta[d]pyrimidin-11-yl)(2-chloro-3-(trifluoromethyl)phenyl)methanone, (2-chloro-3-(trifluoromethyl)phenyl)(2-methyl-4-(thiazol-2-yl)-5,6,7,8,9,10-hexahydro-6,10-epiminocycloocta[d]pyrimidin-11-yl)methanone, (2-chloro-3-(trifluoromethyl)phenyl)(2-methyl-4-(1H-pyrrol-2-yl)-5,6,7,8,9,10-hexahydro-6,10-epiminocycloocta[d]pyrimidin-11-yl)methanone, (2-chloro-3-(trifluoromethyl)phenyl)(2-methyl-4-(thiazol-4-yl)-5,6,7,8,9,10-hexahydro-6,10-epiminocycloocta[d]pyrimidin-11-yl)methanone, (2-chloro-3-(trifluoromethyl)phenyl)(4-(isoxazol-4-yl)-2-methyl-5,6,7,8,9,10-hexahydro-6,10-epiminocycloocta[d]pyrimidin-11-yl)methanone, (2-chloro-3-(trifluoromethyl)phenyl)(2-methyl-4-(thiophen-3-yl)-5,6,7,8,9,10-hexahydro-6,10-epiminocycloocta[d]pyrimidin-11-yl)methanone, (2-chloro-3-(trifluoromethyl)phenyl)(2-methyl-4-(4H-1,2,4-triazol-4-yl)-5,6,7,8,9,10-hexahydro-6,10-epiminocycloocta[d]pyrimidin-11-yl)methanone, (2-chloro-3-(trifluoromethyl)phenyl)(4-(5-hydroxypyrimidin-2-yl)-2-methyl-5,6,7,8,9,10-hexahydro-6,10-epiminocycloocta[d]pyrimidin-11-yl)methanone, (2-chloro-3-(trifluoromethyl)phenyl)(4-(5-fluoropyrimidin-2-yl)-2-methyl-5,6,7,8,9,10-hexahydro-6,10-epiminocycloocta[d]pyrimidin-11-yl)methanone, (2-chloro-3-(trifluoromethyl)phenyl)(2-methyl-4-(4-methylpyrimidin-2-yl)-5,6,7,8,9,10-hexahydro-6,10-epiminocycloocta[d]pyrimidin-11-yl)methanone, (2-chloro-3-(trifluoromethyl)phenyl)(2-methyl-4-(5-methylpyridin-2-yl)-5,6,7,8,9,10-hexahydro-6,10-epiminocycloocta[d]pyrimidin-11-yl)methanone, (2-chloro-3-(trifluoromethyl)phenyl)(2-methyl-4-phenyl-5,6,7,8,9,10-hexahydro-6,10-epiminocycloocta[d]pyrimidin-11-yl)methanone, (2-chloro-3-methylphenyl)(2-methyl-4-(1H-pyrazol-5-yl)-5,6,7,8,9,10-hexahydro-6,10-epiminocycloocta[d]pyrimidin-11-yl)methanone, (2-chloro-4-fluoro-3-(trifluoromethyl)phenyl)(2-methyl-4-(1H-pyrazol-5-yl)-5,6,7,8,9,10-hexahydro-6,10-epiminocycloocta[d]pyrimidin-11-yl)methanone, (3-methyl-2-(trifluoromethyl)pyridin-4-yl)(2-methyl-4-(1H-pyrazol-5-yl)-5,6,7,8,9,10-hexahydro-6,10-epiminocycloocta[d]pyrimidin-11-yl)methanone, (2,3-dimethylpyridin-4-yl)((6S,10R)-2-methyl-4-(1H-pyrazol-5-yl)-5,6,7,8,9,10-hexahydro-6,10-epiminocycloocta[d]pyrimidin-11-yl)methanone, (2-methyl-3-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone, (2,3-dimethylpyridin-4-yl)((6S,10R)-2-methyl-4-(1H-pyrazol-5-yl)-5,6,7,8,9,10-hexahydro-6,10-epiminocycloocta[d]pyrimidin-11-yl)methanone, (2-methyl-3-(trifluoromethyl)pyridin-4-yl)((6S,10R)-2-methyl-4-(1H-pyrazol-5-yl)-5,6,7,8,9,10-hexahydro-6,10-epiminocycloocta[d]pyrimidin-11-yl)methanone, and pharmaceutically acceptable salts thereof.

35. A pharmaceutical composition, comprising:

(a) a therapeutically effective amount of a compound independently selected from compounds of Formula (I):

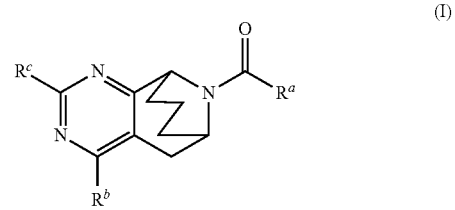

or enantiomers or diastereomers thereof;
or pharmaceutically acceptable salts thereof;
wherein:
$R^a$ is

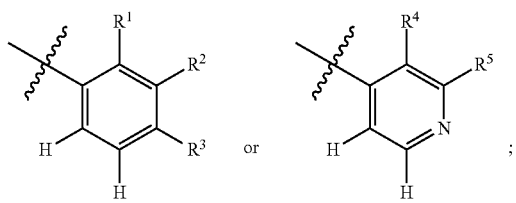

$R^1$, $R^2$, $R^3$, and $R^4$ are each independently selected from the group consisting of: H, halo, $C_1$-$C_3$alkyl and $C_1$-$C_3$perhaloalkyl;

$R^5$ is $C_1$-$C_3$perhaloalkyl or $C_1$-$C_3$alkyl;

$R^b$ is selected from the group consisting of:

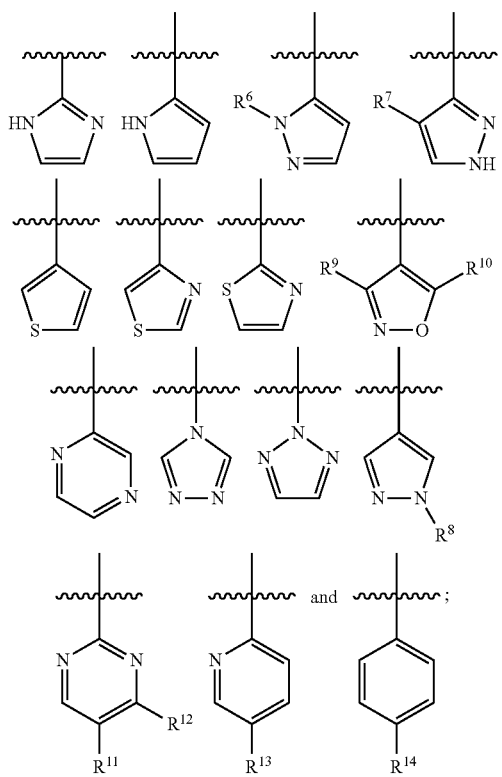

Wherein:
  $R^6$, $R^8$, $R^9$, $R^{10}$, $R^{12}$, $R^{13}$ are independently H or $C_1$-$C_3$alkyl;
  $R^7$ is H, halo or $C_1$-$C_3$perhaloalkyl;
  $R^{11}$ is H, halo or OH;
  $R^{14}$ is H or halo; and
  $R^c$ is selected from the group consisting of: H, $NH_2$, $C_1$-$C_4$alkyl; and
(b) at least one pharmaceutically acceptable excipient.

36. A pharmaceutical composition comprising a therapeutically effective amount of a compound of claim 34 and at least one pharmaceutically acceptable excipient.

* * * * *